(12) United States Patent
Gibson et al.

(10) Patent No.: US 11,884,916 B2
(45) Date of Patent: Jan. 30, 2024

(54) MATERIALS AND METHODS FOR THE SYNTHESIS OF ERROR-MINIMIZED NUCLEIC ACID MOLECULES

(71) Applicant: Codex DNA, Inc., San Diego, CA (US)

(72) Inventors: Daniel G Gibson, Carlsbad, CA (US); Nicky Caiazza, Rancho Santa Fe, CA (US); Toby H. Richardson, San Diego, CA (US)

(73) Assignee: Telesis Bio Inc., La Jolla, CA (US)

( * ) Notice: Subject to any disclaimer, the term of this patent is extended or adjusted under 35 U.S.C. 154(b) by 558 days.

(21) Appl. No.: 16/920,204

(22) Filed: Jul. 2, 2020

(65) Prior Publication Data

US 2020/0332286 A1 Oct. 22, 2020

Related U.S. Application Data

(60) Continuation of application No. 15/667,515, filed on Aug. 2, 2017, now Pat. No. 10,704,041, which is a division of application No. 13/757,633, filed on Feb. 1, 2013, now Pat. No. 9,771,576.

(60) Provisional application No. 61/593,813, filed on Feb. 1, 2012.

(51) Int. Cl.
| | |
|---|---|
| *C12N 15/10* | (2006.01) |
| *C12N 9/22* | (2006.01) |
| *C12Q 1/6844* | (2018.01) |
| *C12P 19/34* | (2006.01) |

(52) U.S. Cl.
CPC .......... *C12N 15/1093* (2013.01); *C12N 9/22* (2013.01); *C12P 19/34* (2013.01); *C12Q 1/6844* (2013.01); *C12Y 301/11* (2013.01); *C12Y 301/21* (2013.01); *C07K 2319/00* (2013.01); *C07K 2319/02* (2013.01); *C07K 2319/036* (2013.01)

(58) Field of Classification Search
CPC ....... C12N 15/1093; C12N 9/22; C12P 19/34; C12Q 1/6844; C12Y 301/11; C12Y 301/21; C07K 2319/00; C07K 2319/036; C07K 2319/21

See application file for complete search history.

(56) References Cited

U.S. PATENT DOCUMENTS

| | | | |
|---|---|---|---|
| 5,869,245 A | 2/1999 | Yeung | |
| 6,391,557 B1 | 5/2002 | Yeung | |
| 6,699,980 B1 | 3/2004 | Yeung | |
| 7,056,740 B2 | 6/2006 | Padgett et al. | |
| 7,078,211 B2 | 7/2006 | Padgett et al. | |
| 7,129,075 B2 | 10/2006 | Gerard et al. | |
| 7,273,739 B2 | 9/2007 | Padgett | |
| 7,560,261 B2 | 7/2009 | Shandilya et al. | |
| 7,838,219 B2 | 11/2010 | Padgett et al. | |
| 2003/0148315 A1 | 8/2003 | Padgett et al. | |
| 2003/0157495 A1 | 8/2003 | Padgett et al. | |
| 2004/0166510 A1 | 8/2004 | Gerard et al. | |
| 2004/0180352 A1* | 9/2004 | Padgett | C12N 15/1027 435/6.12 |
| 2007/0231904 A1* | 10/2007 | Shandilya | C12N 9/22 536/23.1 |
| 2007/0269870 A1 | 11/2007 | Church et al. | |
| 2008/0145913 A1 | 6/2008 | Padgett et al. | |
| 2010/0035768 A1 | 2/2010 | Gibson et al. | |
| 2013/0109596 A1 | 5/2013 | Peterson | |

FOREIGN PATENT DOCUMENTS

| | | |
|---|---|---|
| WO | WO 1997/046701 | 12/1997 |
| WO | WO 2002/079468 A2 | 10/2002 |
| WO | WO 2003/066809 A2 | 8/2003 |
| WO | WO 2004/035771 A1 | 4/2004 |
| WO | WO 2008/112683 A2 | 9/2008 |
| WO | WO 2011/102802 A1 | 8/2011 |

OTHER PUBLICATIONS

Doetsch, Paul W. et al.: "*Nuclease SP: a novel enzyme from spinach that incises damaged duplex DNA preferentially at sites of adenine*" Nucleic Acids Research, vol. 16, No. 14, 1988, pp. 6935-6952.
International Search Report (ISR) from PCT/US2013/24496.
JP Office Action dated Nov. 10, 2016, regarding JP 2014-555797.
Kadyrov, Farid A. et al.: "*Endonucleolytic Function of MutLlalpha] in Human Mismatch Repair*"; Cell, vol. 126, No. 2, Jul. 1, 2006, pp. 297-308.
NEB Datasheet for T7 Exonuclease; Dec. 17, 2012 (indicated as document disclosure date by document properties) [online]. [Retrieved on Apr. 4, 2013]. Retrieved from the internet: <URL: https://www.neb.comNmedia/Catalog/All- Products/ 284FE8DF86F44894A7A72B88AC920A86/Datacards% 20orY020Manuals/M0263Datasheet-Lot0031212.pdf> Provided to document directionality of T7 exonuclease activity.
NEB Datasheet for Exonuclease III; Dec. 17, 2012 (indicated as document disclosure date by document properties) [online]. [Retrieved on Apr. 4, 2013]. Retrieved from the internet: <URL: https://www.neb.com/-/media/Catalog/All-Products/ ADC760721372D4E01815F8A7E466F4F4C/Datacards%20or% 20Manuals/M0206. Datasheet-Lot0321207> Provided to document directionality of Exo III exonuclease activity.

(Continued)

*Primary Examiner* — David C Thomas
(74) *Attorney, Agent, or Firm* — DLA Piper LLP (US)

(57) ABSTRACT

The present invention provides materials and methods useful for error correction of nucleic acid molecules. In one embodiment of the invention, a first plurality of double-stranded nucleic acid molecules having a nucleotide mismatch are fragmented by exposure to a molecule having unidirectional mismatch endonuclease activity. The nucleic acid molecules are cut at the mismatch site or near the mismatch site, leaving a double-stranded nucleic acid molecule having a mismatch at the end or near end of the molecule. The nucleic acid molecule is then exposed to a molecule having unidirectional exonuclease activity to remove the mismatched nucleotide. The missing nucleotides can then be filled in by the action of, e.g., a molecule having DNA polymerase activity. The result is double-stranded nucleic acid molecules with a decreased frequency of nucleotide mismatches. Also provided are novel nucleic acid sequences encoding mismatch endonucleases, polypeptides encoded thereby, as well as nucleic acid constructs, transgenic cells, and various compositions thereof.

12 Claims, 7 Drawing Sheets

Specification includes a Sequence Listing.

(56) References Cited

OTHER PUBLICATIONS

NEB Datasheet for T4 DNA Polymerase; Dec. 17, 2012 (indicated as document disclosure date by document properties) [online]. (Retrieved on Apr. 4, 2013]. Retrieved from the internet: <URL: https://www.neb.com/-/media/Catalog/All-Products/97620738CFC74BB899614AA9FE4E5BCA/Datacards%20or%20Manuals/M0203Datasheet-Lot0401206> Provided to document presence and direction of exonuclease activity associated with T4 polymerase.
Pimkinl, Maxim et al.: "*Recombinant nucleases CEL I from celery and SP I from spinach for mutation detection*"; BMC Biotechnology, 2007, 7:29, 8 pages.
Qiu, Peter et al.: "*Mutation detection using Surveyor nuclease*"; BioTechniques, vol. 36, No. 4 (2004), pp. 702-706.
Saaem et al.: "*Error correction of microchip synthesized genes using Surveyor nuclease*": Nucleic Acids Research, vol. 40, No. 3, Nov. 29, 2011, pp. e23-e23.
Supplementary European Search Report dated Oct. 23, 2015, regarding EP 13 74 3710.9.
Yang Bing et al.: "*Purification, Cloning, and Characterization of the CEL I Nuclease*"; Cell Bio Chem, 2000, 9 pgs.
Yao, Min et al.: "*Strand-specific Cleavage of Mismatch-containing DNA by Deoxyinosine 3'Endonuclease from Escherichia coli*"; J Bio Chem, vol. 269, No. 50, Dec. 16, 1994, pp. 31390-21396.
Lucas, S et al.: "*CBPG5929.b1 CBPG Mimulus guttatus IM62 roots, seedlings, fruits, callus (L) Mimulus guttatus cDNA clone CBPG5929 5', mRNA sequence.*"; May 31, 2009, retrieved from EBI accession No. EM_EST:GR177842, Database accession No. GR177842, XP-002795764.
Lucas, S. et al.: "*CCIC7557.b1 CCIC Mimulus guttatus IM62 roots (H) Mimulus guttatus CDNA clone CCIC7557 5', mRNA sequence.*"; May 28, 2009, retrieved from EBI accession No. Em EST:GRO18143, Database accession No. GR018143. XP-002795765.
Larsen, Knud: "*Molecular cloning and characterization of a cDNA encoding endonuclease from potato (Solanum tuberosum)*"; Journal of Plant Physiology, Nov. 15, 2005, vol. 162, No. 11, pp. 1263-1269, XP027800309.
Larsen, K. and Bendixen, C.: "*Solanum tuberosum endonuclease mRNA, complete cds.*", Aug. 1, 2004, retrieved from EBI accession No. EM_STD:AY676603, Database accession No. AY676603.
Partial European Search Report dated Jan. 2, 2020, regarding EP 19 193 201.1.
Israeli Office Action dated Mar. 27, 2019, regarding IL 233687.

* cited by examiner

Section 5

```
                                        285         290         300         310         320         334
CEL1_US6391557_SEQIDNO_04   (285)  GGITRISMILNRVILGSS---------ADHSLA------------------------------
CEL1_US7078211_SEQIDNO_02   (275)  GGVRIASILNRIFGGAK---------SNRSISRSSM----------------------------
CEL2_US7560261_SEQIDNO_06   (270)  AGVRLAATLNRIFTSNPSDLTRLNMHNGGHRSISNNIEIV-------------------------
CEL2_US7560261_SEQIDNO_08   (272)  AGVRLAATLNRIFTSNPSDLTRLNMHNGGHRSISNNIEIV-------------------------
SEQIDNO_10_CEL1_Mimulus     (252)  GGVRLAMILNRVFGDS----------KEDSLIAT------------------------------
SEQIDNO_13_CEL1_Solanum     (283)  GGITRLAMILNNVFGVSQ--------QEDSVAAT------------------------------
SEQIDNO_16_CELII_Vitis      (278)  SGITRLAATLNRIFASIQ--------GKRAKA--------------------------------
SEQIDNO_23_CELII_Vitis      (255)  GGIRLAATLNRIFASIQP---K-ISLKHEDKRVEKTTPVDYIEWSPLQQFS
SEQIDNO_25_CELII_Solanum    (278)  GGVRLAEVLNRIFTKKP---------SDAAQ---------------------------------
SEQIDNO_27_CELII_Medicago   (275)  GGVRLAAILNRIFTPKT---------RIAQA---------------------------------
Consensus                   (273)  GGVRLAAILNRIFGS           RS
                            (285)
```

FIG. 4-3

MATERIALS AND METHODS FOR THE SYNTHESIS OF ERROR-MINIMIZED NUCLEIC ACID MOLECULES

CROSS-REFERENCE TO RELATED APPLICATIONS

This application is a continuation application of U.S. application Ser. No. 15/667,515 filed Aug. 2, 2017, now issued as U.S. Pat. No. 10,704,041; which is a divisional application of U.S. application Ser. No. 13/757,633 filed Feb. 1, 2013, now issued as U.S. Pat. No. 9,771,576; which claims the benefit under 35 USC § 119(e) to U.S. Application Ser. No. 61/593,813 filed Feb. 1, 2012, now expired. The disclosure of each of the prior applications is considered part of and is incorporated by reference in the disclosure of this application.

INCORPORATION OF SEQUENCE LISTING

The material in the accompanying Sequence Listing is hereby incorporated by reference into this application. The accompanying sequence listing text file, named CODEX1550-3_ST25.txt, was created on Jul. 2, 2020 and is 64 KB in size. The file can be accessed using Microsoft Word on a computer that uses Windows OS.

BACKGROUND OF THE INVENTION

Field of the Invention

The present invention relates generally to molecular biology and genetics, and to the synthesis of genes and other nucleic acid molecules.

Background Information

In modern molecular biology and genetic engineering, many molecular techniques that involve the use of molecules of nucleic acid often require the generation of a supply of nucleic acid molecules by synthetic methods. For example, to test hypotheses in the field of metabolic engineering or genomics, and to synthesize designed proteins and organisms with tailored genomes, cost-effective methods for synthesizing nucleic acid molecules with a high degree of fidelity to an intended nucleotide sequence are often required. Common methods of nucleic acid synthesis, e.g., synthesis of double-stranded DNA, include polymerase chain reaction methods and ligation chain reaction methods. Often, ensuring that a synthetic DNA molecule contains the correct nucleotide sequence is important, if not essential, for the success of the molecular technique in which the synthesized DNA is to be used. For example, the synthesis of a DNA coding sequence for use in gene expression of functional polypeptides requires a precise DNA sequence; because even one nucleotide substitution, insertion or deletion can have significant consequences for the polypeptide that is ultimately produced. Thus, the process of minimizing DNA molecules having incorrect DNA sequences from a synthetic DNA population is widely considered to be essential in providing error-free synthetic DNA produced by a de novo gene synthesis method.

Recently, efforts to synthesize nucleic acid molecules accurately while controlling costs have yielded methods including microchip-based gene synthesis and PCR-based gene assembly technologies. While these conventional technologies provide the capability to synthesize multiple genes, reducing errors introduced into the desired gene-sequence remains challenging. To avoid the problems with sequence errors inherent in gene synthesis, some have focused on purifying the oligonucleotides that are used at the early stages of the synthesis process. However, these oligonucleotide purification approaches are costly, and sequence errors persist and propagate through the subsequent steps of the synthesis process.

Thus, there exists a need for alternative methods for reducing sequence errors within a population of DNA molecules. What is desired is a way to synthesize genes and other nucleic acid molecules with a greater yield of molecules having a desired nucleotide sequence. An approach that can correct sequence errors at a much later step in the synthesis process makes the desired increase in nucleotide sequence accuracy possible, while allowing the process to be cost-effective.

SUMMARY OF THE INVENTION

The present invention provides methods and materials for error correction in the replication and amplification of nucleic acid molecules. In one embodiment of the invention a first plurality of double-stranded nucleic acid molecules having a nucleotide mismatch are fragmented by exposure to a unidirectional mismatch endonuclease. The nucleic acid molecules are cut at or near the mismatch site with an endonuclease, leaving a double-stranded nucleic acid molecule having a mismatch at or near the end of the molecule. In one embodiment the nucleic acid molecule is then exposed to an exonuclease having a unidirectional activity in the 5' to 3' or 3' to 5' direction, which therefore removes the mismatched nucleotide. A second plurality of double-stranded nucleic acid molecules is assembled from the nucleic acids with the mismatched nucleotides removed. The missing nucleotides can then be filled in by the action of, e.g., a DNA polymerase either directly or at a subsequent amplification step, and these steps can be repeated as many times as necessary. The result is double-stranded nucleic acid molecules with a decreased frequency of nucleotide mismatches versus the first plurality of nucleic acid molecules.

Thus, in one aspect the present invention provides a method for error correction of nucleic acid molecules. The method involves (a) obtaining a first plurality of double-stranded nucleic acid molecules having at least one nucleotide mismatch; (b) fragmenting the plurality of double-stranded nucleic acid molecules having a mismatch by reacting the nucleic acid molecules having a mismatch with at least one molecule having a unidirectional mismatch endonuclease activity; (c) removing the nucleotide mismatch by reacting the fragmented double-stranded nucleic acid molecules having a mismatch of (b) with at least one molecule having unidirectional exonuclease activity of the same directionality as the unidirectional mismatch endonuclease activity of (b) to provide a fragmented error-free double-stranded nucleic acid molecule; and (d) assembling a second plurality of double-stranded nucleic acid molecules having the fragmented error-free double-stranded nucleic acid molecule of (c). The second plurality of double-stranded nucleic acid molecules has a decreased frequency of nucleotide mismatches as compared to the first plurality of double-stranded nucleic acid molecules.

In one embodiment, the first plurality of nucleotide acid molecules can contain one or more synthetic nucleotide sequences. The first plurality of nucleotide acid molecules can contain a mixture of one or more naturally occurring gene sequences and one or more synthetic nucleotide sequences. The first plurality of nucleic acid molecules can be obtained by synthesizing the nucleic acid molecules in one embodiment, or by assembling the nucleic acid molecules from subsets and/or oligonucleotides in another embodiment.

In one embodiment of the method, steps (b) and (c) recited above are performed as separate reactions, but in another embodiment steps (b) and (c) are performed as a simultaneous or one-step reaction. In one embodiment of the method, the unidirectional mismatch endonuclease activity cuts 5' to the mismatch and the unidirectional exonuclease activity removes the nucleotide mismatch from the 5' end of the fragmented nucleic acid molecule. But in another embodiment the unidirectional mismatch endonuclease activity cuts 3' to the mismatch and the unidirectional exonuclease activity removes the nucleotide mismatch from the 3' end of the fragmented nucleic acid molecule. Examples of the molecule having unidirectional mismatch endonuclease activity include, but are not limited to, RES I, CEL I, CEL II, an SP endonuclease, SP I endonuclease, T7 endonuclease, T4 endonuclease, endonuclease V, a Mut protein, a variant of any thereof, and a combination of any two or more thereof. In a preferred embodiment, CEL I, CEL II, or a combination of CEL I and CEL II is utilized. In another preferred embodiment, the molecule having a unidirectional mismatch endonuclease activity is encoded by a nucleic acid molecule comprising a nucleotide sequence which hybridizes under low, moderate, or high stringency conditions to a nucleic acid sequence selected from the group consisting of a) a nucleic acid sequence hybridizing under low, moderate, or high stringency conditions to a nucleic acid sequence selected from the group consisting of SEQ ID NO: 01, SEQ ID NO: 03, SEQ ID NO: 05, SEQ ID NO: 07, SEQ ID NO: 09, SEQ ID NO: 12, SEQ ID NO: 15, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, a complement of any, and a fragment of any; b) a nucleic acid sequence exhibiting 70% or greater identity to a nucleic acid sequence selected from the group consisting of SEQ ID NO: 01, SEQ ID NO: 03, SEQ ID NO: 05, SEQ ID NO: 07, SEQ ID NO: 09, SEQ ID NO: 12, SEQ ID NO: 15, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, a complement of any, and a fragment of any; and c) a nucleic acid sequence encoding a polypeptide exhibiting 60% or greater identity to an amino acid sequence selected from the group consisting of SEQ ID NO: 02, SEQ ID NO: 04, SEQ ID NO: 06, SEQ ID NO: 08, SEQ ID NO: 10, SEQ ID NO: 11, SEQ ID NO: 13, SEQ ID NO: 14, SEQ ID NO: 16, SEQ ID NO: 17, SEQ ID NO: 19, SEQ ID NO: 21, SEQ ID NO: 23, SEQ ID NO: 25, SEQ ID NO: 27, SEQ ID NO: 28, and SEQ ID NO: 29.

Examples of the molecule having unidirectional exonuclease activity include, but are not limited to, exonuclease III, a DNA polymerase, lambda exonuclease, T7 exonuclease, and T5 exonuclease, and variants thereof. In one embodiment the molecule having unidirectional exonuclease activity is a DNA polymerase with proofreading activity (e.g., 3' exonuclease proofreading activity). Examples of polymerases with proofreading activity include, but are not limited to, T4 polymerase, T7 polymerase, and phi29 polymerase.

In a specific embodiment of the methods of the present invention, the at least one molecule having unidirectional mismatch endonuclease activity is selected from: CEL I, CEL II, variants of any thereof, and a combination of any two or more thereof; and the at least one molecule having unidirectional exonuclease activity selected from the group consisting of exonuclease III, a variant thereof, and a combination of any two or more thereof.

In one aspect of the invention, the present disclosure provides isolated nucleic acid molecules comprising nucleic acid sequences hybridizing under low, moderate, or high stringency conditions: a) a nucleic acid sequence hybridizing under low, moderate, or high stringency conditions to a nucleic acid sequence selected from the group consisting of SEQ ID NO: 09, SEQ ID NO: 12, SEQ ID NO: 15, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, a complement thereof or a fragment of either; or b) a nucleic acid sequence exhibiting 70% or greater identity to a nucleic acid sequence selected from the group consisting of SEQ ID NO: 09, SEQ ID NO: 12, SEQ ID NO: 15, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, a complement thereof or a fragment of either; or c) a nucleic acid sequence encoding a polypeptide exhibiting 50% or greater identity to an amino acid sequence selected from the group consisting of SEQ ID NO: 10, SEQ ID NO: 11, SEQ ID NO: 13, SEQ ID NO: 14, SEQ ID NO: 16, SEQ ID NO: 17, SEQ ID NO: 19, SEQ ID NO: 21, SEQ ID NO: 23, SEQ ID NO: 25, SEQ ID NO: 27, SEQ ID NO: 28, and SEQ ID NO: 29.

In another aspect of the invention, the present disclosure provides recombinant nucleic acid constructs, such as recombinant nucleic acid vectors, which include a nucleic acid molecule of the invention as recited herein that is operably linked to a heterologous nucleic acid. In some embodiments the heterologous nucleic acid is a heterologous transcription control element. In some preferred embodiments, any of the above recombinant nucleic acid constructs can comprise a heterologous nucleic acid encoding a polypeptide sequence. The polypeptide sequence may include a secretion signal or an epitope tag. In particular embodiments the nucleic acid constructs can comprise SEQ ID NO: 31 or SEQ ID NO: 33, or complements or variants thereof or comprise sequences that hybridize under low, medium, or high stringency conditions to either of SEQ ID NO: 31 or 33 or their complements or variants thereof.

In yet another aspect of the invention, the invention provides a recombinant host cell that includes a nucleic acid construct of the invention as disclosed herein. The recombinant host cell can be an insect cell, a mammalian cell, a microbial cell, or a plant cell. In some other embodiments, the disclosure also provides biological samples, biomass, and progeny derived from a host organism as described above. In yet other embodiments, the disclosure further provides biomaterials derived from a host organism as described above.

In another aspect of the present invention, the invention further provides isolated polypeptides. In some embodiments, such isolated polypeptides are expressed by a nucleic acid molecule of the invention as disclosed herein. The nucleic acid molecule expressing the polypeptides can be introduced into a host cell. In some embodiments the amino acid sequence of the polypeptide can comprise an amino acid sequence selected from the group consisting of SEQ ID NO: 11, amino acid residues 1 to 297 of SEQ ID NO: 11, amino acid residues 22 to 308 of SEQ ID NO: 11, SEQ ID NO: 17, amino acid residues 1 to 320 of SEQ ID NO: 17, and amino acid residues 22 to 331 of SEQ ID NO: 17.

In another aspect, the present invention discloses compositions comprising: (i) a molecule having a unidirectional mismatch endonuclease activity; and (ii) a molecule having unidirectional exonuclease activity of the same directionality as the unidirectional mismatch endonuclease activity in (i). In various embodiments the molecule of (i) is selected from the group consisting of RES I, CEL I, CEL II, T7 endonuclease, T4 endonuclease, endonuclease V, a Mut protein, a variant of any thereof, and a combination of any two or more thereof; and the molecule of (ii) is selected from the group consisting of exonuclease III, a DNA polymerase, a variant of any thereof, and a combination of any two or more thereof.

In yet another aspect, the present disclosure further provides a kit comprising (i) a molecule having a unidirectional mismatch endonuclease activity; and (ii) a molecule having unidirectional exonuclease activity of the same directionality as the unidirectional mismatch endonuclease activity in (i). In other embodiments the kit can also have instructions for conducting a method for error correction as described herein and/or provide a link to a website that provides information on a method of error correction as described herein.

These and other objects, aspects, and features of the invention will become more fully apparent to those of ordinary skill in the art upon review of the following detailed description of the invention and the claims in conjunction with the accompanying figures.

BRIEF DESCRIPTION OF THE DRAWINGS

FIGS. 4-1, 4-2 and 4-3 are alignments of a *Selaginella lepidophlla* CEL I endonuclease (SEQ ID NO: 02), a celery CEL I endonuclease (SEQ ID NO: 04), an *Apium* sp. CEL II endonuclease (SEQ ID NO: 06), another *Apium* sp. CEL II endonuclease (SEQ ID NO: 08), *Mimulus guttatus* CEL I endonuclease (SEQ ID NO: 10), a *Solanum tuberosum* CEL I endonuclease (SEQ ID NO: 13), a *Vitis vinifera* CEL II endonuclease (SEQ ID NO: 16), a *Solanum tuberosum* CEL II endonuclease (SEQ ID NO: 25), a *Medicago* sp. CEL II endonuclease (SEQ ID NO: 27). The sequence alignments of FIGS. 4-1, 4-2 and 4-3 were generated using the program AlignX of the Vector NTI Advance™ 11.5 package (Invitrogen, Carlsbad, Calif.) with default settings. As discussed in detail elsewhere herein, several polypeptide domains and motifs with high degree of conservation have been identified from this sequence comparison analysis. In the alignment figure shown herein, a dash in an aligned sequence represents a gap, i.e., a lack of an amino acid at that position. Black boxes and gray boxes identify identical amino acids and conserved amino acids, respectively, among aligned sequences.

DETAILED DESCRIPTION OF THE INVENTION

Figure 1:
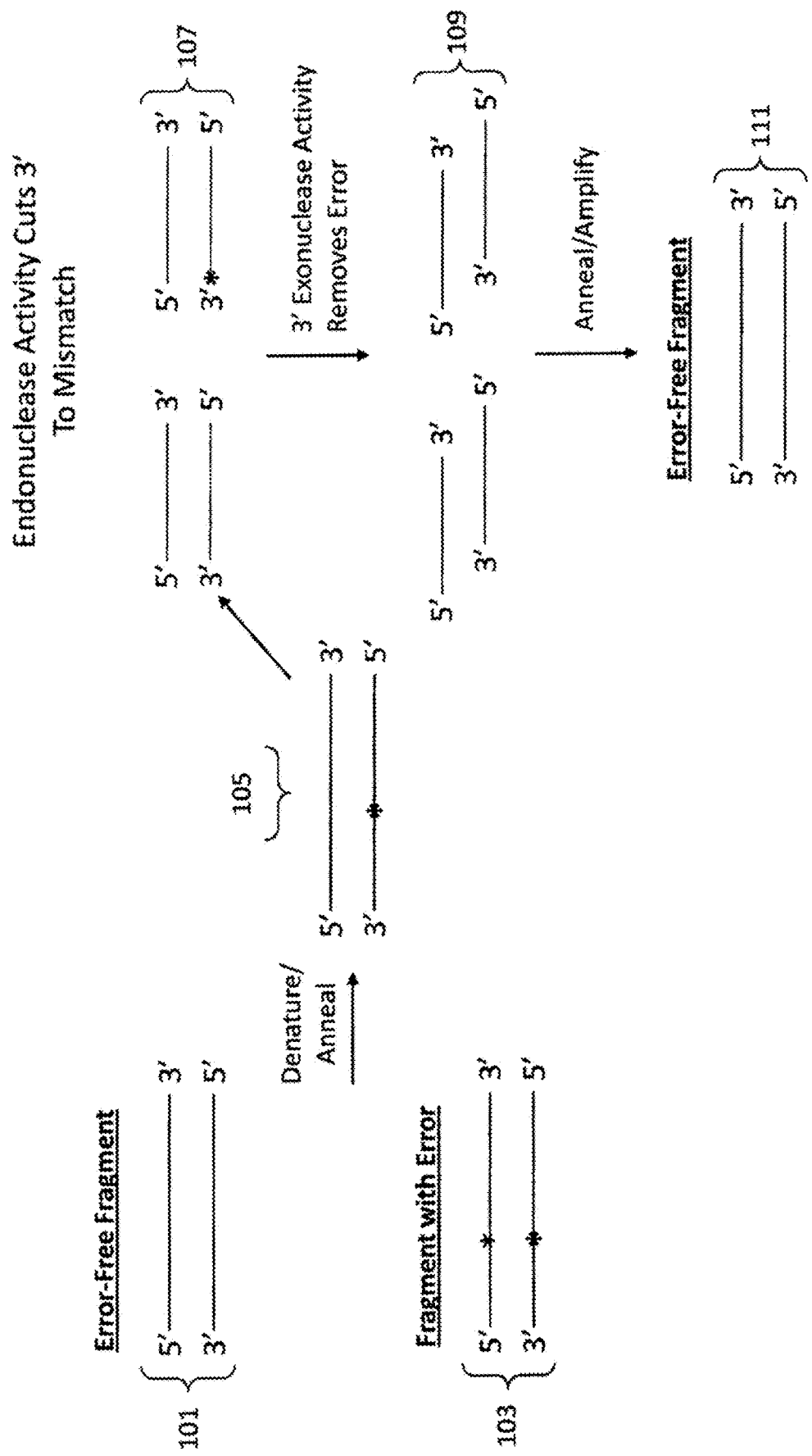
FIG. 1 provides schematic illustration of an embodiment of the methods of the present invention.

The present application relates to compositions, methods and related materials useful for the production of error-minimized nucleic acid molecules.

In one aspect, the present disclosure provides materials and methods that can be used to reduce mismatch errors in a population of nucleic acid molecules. For example, nucleic acid molecules that encode mismatch endonucleases are disclosed as well as methods for using such nucleic acid molecules and polypeptides encoded thereby to reduce nucleotide mismatches in a nucleic acid population. The disclosure also provides recombinant nucleic acid molecules, and recombinant cells as well as recombinant organisms comprising such nucleic acid molecules and methods for using the same.

The singular form "a", "an", and "the" include plural references unless the context clearly dictates otherwise. For example, the term "a cell" includes one or more cells, including mixtures thereof.

Domain: "Domains" are groups of substantially contiguous amino acids in a polypeptide that can be used to characterize protein families and/or parts of proteins. Such domains typically have a "fingerprint", "motif", or "signature" that can comprise conserved primary sequence, secondary structure, and/or three-dimensional conformation. Generally, domains are correlated with specific in vitro and/or in vivo activities. A domain can have a length of from 4 amino acids to 400 amino acids, e.g., 4 to 50 amino acids, or 4 to 20 amino acids, or 4 to 10 amino acids, or 4 to 8 amino acids, or 25 to 100 amino acids, or 35 to 65 amino acids, or 35 to 55 amino acids, or 45 to 60 amino acids, or 200 to 300 amino acids, or 300 to 400 amino acids.

Expression: As used herein, "expression" refers to the process of converting genetic information of a polynucleotide into RNA through transcription, which is typically catalyzed by an enzyme, RNA polymerase, and into protein, through translation of mRNA on ribosomes.

The term "epitope", "tag", "tag sequence", or "protein tag" as used herein refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., FLAG epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The Polynucleotides of the Invention and Polypeptides Encoded Thereby

In one aspect of the present invention, the disclosure provides novel isolated nucleic acid molecules, nucleic acid molecules that hybridize to these nucleic acid molecules (e.g., complements), and nucleic acid molecules that encode the same protein due to the degeneracy of the DNA code. Additional embodiments of the present application further include the polypeptides encoded by the nucleic acid molecules of the present invention.

The polynucleotides and polypeptides of the present invention disclosed in the sequence listing or otherwise disclosed herein (and their fragments or variants) are "biologically active" with respect to either a structural attribute, such as the capacity of a nucleic acid to hybridize to another nucleic acid molecule, or the ability of a polypeptide to be bound by an antibody (or to compete with another molecule for such binding). Alternatively, such an attribute may be catalytic and thus involve the capacity of the molecule to mediate a chemical reaction or response.

In some embodiments the polynucleotides and polypeptides of the present invention are recombinant. A recombinant polynucleotide or polypeptide is one derived from human manipulation of the polynucleotide or polypeptide and an organism using laboratory methods resulting in nucleic acid sequences (or polypeptides) that would not otherwise be found in (or produced by) the manipulated organism.

Nucleic acid molecules or fragments thereof of the present invention are capable of specifically hybridizing to other nucleic acid molecules under certain circumstances. "Specifically hybridize" refers to a process whereby complementary nucleic acid strands anneal to each other under appropriately stringent conditions. Nucleic acid molecules are said to exhibit "complete complementarity" if every nucleotide of one of the molecules is complementary to a nucleotide of the other and the nucleotide pairs form Watson-Crick base pairs. Two nucleic acid molecules are said to be "minimally complementary" if they can anneal to one another with sufficient stability to remain annealed under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al. in Molecular Cloning, *A Laboratory Manual*, $2^{nd}$ Edition, Cold Spring Harbor Press, Cold Spring Harbor, NY (1989), and by Haymes et al. In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations employed.

Appropriate stringency conditions which promote DNA hybridization include, for example, 6.0× sodium chloride/sodium citrate (SSC) at about 45° C., followed by a wash of 2.0×SSC at about 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These conditions are known to those skilled in the art, or can be found in *Current Protocols in Molecular Biology*, John Wiley & Sons, N.Y. (1989), 6.3.1-6.3.6. For example, low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). High stringency conditions typically involve nucleic acid hybridization in about 2×SSC to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL fish sperm DNA, and 0.1% (w/v) SDS, with incubation at 55×C for several hours. Hybridization is generally followed by several wash steps. The wash compositions generally comprise 0.5×SSC to about 10×SSC, and 0.01% (w/v) to about 0.5% (w/v) SDS with a 15-min incubation at about 20° C. to about 70° C. Preferably, the nucleic acid segments remain hybridized after washing at least one time in 0.1×SSC at 65° C.

In one embodiment, a subset of the nucleic acid molecules of this invention includes fragments of the disclosed polynucleotides consisting of oligonucleotides of at least 12, at least 15, at least 16, at least 17, at least 18, at least 19, and at least 20 consecutive nucleotides of the disclosed polynucleotide. Such oligonucleotides are fragments of the larger polynucleotide molecules disclosed in the sequence listings or otherwise described herein and find use, for example, as interfering molecules, probes and primers for detection of the polynucleotides of the present invention.

Nucleic acid molecules of the invention can include a sequence sufficient to encode a biologically active fragment of a domain of a mismatch endonuclease, an entire mismatch endonuclease, or several domains within an open reading frame encoding a mismatch endonuclease.

In another embodiment, the present disclosure specifically provides nucleotide sequences comprising regions that encode polypeptides. The encoded polypeptides may be the complete polypeptide encoded by the gene represented by the protein or polynucleotide, or may be fragments of the encoded protein. Preferably, polynucleotides provided herein encode polypeptides constituting a substantial portion of the complete protein, and more preferentially, constituting a sufficient portion of the complete protein to provide the relevant biological activity, e.g., mismatch endonuclease activity.

Of particular interest are polynucleotides of the present invention that encode a mismatch endonuclease. Such polynucleotides may be expressed in recombinant cells or recombinant organisms to produce molecules having mismatch endonuclease activity. In some embodiments, nucleic acid molecules that are fragments of these mismatch endonuclease-encoding nucleotide sequences are also encompassed by the present invention. A "mismatch endonuclease fragment", as used herein, is intended to be a fragment of a nucleotide sequence that encodes a mismatch endonuclease. A fragment of a nucleotide sequence may encode a biologically active portion of a mismatch endonuclease, or it may be a fragment that can be used as a hybridization probe or PCR primer using methods disclosed herein. Fragments of nucleic acid molecules or polypeptides comprise at least 10, 25, 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides or amino acids, or up to the number of nucleotides or amino acids present in a full-length nucleotide sequence or polypeptide sequence disclosed herein. Fragments of the nucleotide sequences of the present invention include those that encode protein fragments that retain the biological activity of a mismatch endonuclease. By "retains activity" is intended that the fragment will have at least 30%, at least 50%, at least 70%, at least 80%, at least 90%, or at least 95% of the endonuclease activity of the full-length mismatch endonuclease protein. Methods for measuring endonuclease, including mismatch endonuclease activity are well known in the art. See, for example, U.S. Pat. Nos. 6,391,557; 7,129,075. Mismatch endonuclease activity refers to an activity of sufficient level to perform the step of fragmenting the dsDNA molecules (or removing the nucleotide mismatch) in the method within a convenient time period for conducting the assay. In different embodiments the activity is sufficient to perform the fragmenting or removal within 2 hours or within 4 hours or within 6 hours, or within 10 hours or within 12 hours or within 24 hours.

In different embodiments a fragment of a mismatch endonuclease-encoding nucleotide sequence that encodes a biologically active portion of a polypeptide of the invention will encode at least 15, 25, 30, 50, 75, 100, 125, 150, 175, 200, 225, 250, 275, 300, 325, 350 contiguous amino acids, or up to the total number of amino acids present in a full-length mismatch endonuclease protein disclosed in the sequence listing or otherwise disclosed herein. For example, a mismatch endonuclease fragment in accordance with the present invention may have an N-terminal or a C-terminal truncation of at least 20 amino acids, at least 50, at least 75, at least 90, at least 100, or at least 150 amino acids relative to any one of the mismatch endonuclease amino acid sequences disclosed in the sequence listing or otherwise disclosed herein.

Also of interest in the present invention are variants of the polynucleotides disclosed in the sequence listing or otherwise disclosed herein. Such variants may be naturally-occurring, including homologous polynucleotides from the same or a different species, or may be non-natural variants, for example polynucleotides synthesized using chemical synthesis methods, or generated using recombinant DNA techniques. Variants can be generated having modified nucleic acid molecules in which nucleotides have been inserted, deleted, and/or substituted, and such modifications can provide a desired effect on the endonuclease biological activity as described herein. Degeneracy of the genetic code provides the possibility to substitute at least one base of the protein encoding sequence of a gene with a different base without causing the amino acid sequence of the polypeptide produced from the gene to be changed. Hence, the nucleic acid molecules of the present invention may also have any base sequence that has been changed from any one of the polynucleotide sequences disclosed herein by substitution in accordance with degeneracy of the genetic code.

The skilled artisan will further appreciate that changes can be introduced by mutation of the nucleotide sequences of the invention, thereby leading to changes in the amino acid sequence of the encoded endonuclease proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted nonessential amino acid residues. A "nonessential" amino acid residue, as used herein, is a residue that can be altered from the wild-type sequence of a mismatch endonuclease protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As discussed above, it will be appreciated by one skilled in the art that amino acid substitutions may be made in non-conserved regions that retain function. In general, such substitutions would not be made for conserved amino acid residues, or for amino acid residues residing within a conserved motif, where such residues are essential for protein activity. Conserved residues, domains and motifs of mismatch endonuclease sequences are reported in the art. Examples of residues that are conserved and that may be essential for protein activity include, for example, residues that are identical between all proteins contained in an alignment of the amino acid sequences of the present invention and known mismatch endonuclease sequences. Examples of residues that are conserved but that may allow conservative amino acid substitutions and still retain activity include, for example, residues that have only conservative substitutions between all proteins contained in an alignment of the amino acid sequences of the present invention and known mismatch endonuclease sequences. However, one of skill in the art would understand that functional variants may have minor conserved or non-conserved alterations in the conserved residues.

In some embodiments of the present invention, such mismatch endonuclease variants include proteins having an amino acid sequence that differs from any one of the polypeptides disclosed herein, by an amino acid deletion, insertion, or substitution at one or more of the positions corresponding to the conserved amino acid residues as identified in FIG. 4. In some preferred embodiments, such mismatch endonuclease variants include proteins having an amino acid sequence that differs from the polypeptide sequence of SEQ ID NO: 11 or SEQ ID NO: 17 or a fragment of either, by an amino acid deletion, insertion, or substitution at one or more of the positions corresponding to the conserved amino acid residues as identified in FIG. 4, and combinations of any thereof.

Alternatively, variant nucleotide sequences can be made by introducing mutations randomly along all or part of the coding sequence, such as by saturation mutagenesis, and the resultant mutants can subsequently be screened for ability to confer mismatch endonuclease activity in order to identify mutants that retain mismatch endonuclease activity. For example, following mutagenesis, the encoded protein can be expressed recombinantly, and the activity of the protein can be determined using standard assay techniques. Methods for assaying endonuclease activity and particularly mismatch endonuclease activity are well known in the art. See, for example, U.S. Pat. Nos. 6,391,557; 7,129,075.

In addition, using sequence-based methods such as PCR, hybridization, and the like corresponding mismatch endonuclease sequences can be identified, such sequences having substantial identity to the sequences of the invention. See, for example, Sambrook and Russell (2001, supra.).

Polynucleotides and polypeptides that are variants of the polynucleotides and polypeptides provided herein will generally demonstrate significant identity with the polynucleotides and polypeptides provided herein. Of particular interest are polynucleotide and polypeptide homologs having at least about 50% sequence identity, preferably at least about 60%, preferably at least about 70%, more preferably at least about 75%, more preferably at least about 80%, more preferably at least about 85%, more preferably at least about 90%, even more preferably at least about 95%, and most preferably at least about 96%, 97%, 98% or 99% sequence identity with any one of the polynucleotide or polypeptide sequences described in the sequence listing or otherwise described herein. For example, the invention provides polynucleotide homologs having the recited percent sequence identities to polynucleotides of any of SEQ ID NOs: 1, 3, 5, 7, 9, 12, 15, 18, 20, 22, 24, 26, 29, 30, and 32, as well as to constructs SEQ ID NOs: 31 and 33. The invention also provides polypeptides that are encoded by any of the polynucleotides disclosed herein. The invention also provides polypeptide variants having the recited percent sequence identities to polypeptides of any of SEQ ID NO: 2, 4, 6, 8, 10, 11, 13, 14, 16, 17, 19, 21, 23, 25, 27, 28, and 29. The invention also provides fragments of the polynucleotides and polypeptides disclosed herein.

"Sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

"Percentage of sequence identity" or "percent sequence identity", as used herein with reference to polynucleotides, refers to the percentage of identical nucleotides or amino acids in a linear polynucleotide sequence of a reference ("query") polynucleotide molecule (or its complementary strand) as compared to a test ("subject") polynucleotide molecule (or its complementary strand) when the two sequences are optimally aligned. The terms are used in the same way with reference to polypeptide sequences and their corresponding amino acid residues. As is known in the art, when calculating percentage sequence identity for the polynucleotide and/or polypeptide sequences described herein, any leader sequences or sequence tags or other such sequences included for a purpose such as, for example, ease of purification, expression, secretion, etc. are not included in the sequence for the purpose of such calculation.

Percent sequence identity is determined by comparing two optimally locally aligned sequences over a comparison window defined by the length of the local alignment between the two sequences. The polynucleotide sequences in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g., BLAST). The percentage identity is calculated by determining the number of positions at which the identical nucleic acid base (or polypeptide amino acid) occurs in both sequences to yield the number of matched positions, dividing the number of matched positions by the total number of positions in the window of comparison and multiplying the result by 100. Optimal alignment of sequences for aligning a comparison window are well known to those skilled in the art and any may be used in the invention such as the local homology algorithm of Smith and Waterman (*Add. APL. Math.* 2:482, 1981), by the global homology alignment algorithm of Needleman and Wunsch (*J Mol. Biol.* 48:443, 1970), by the search for similarity method of Pearson and Lipman (*Proc. Natl. Acad. Sci.* (USA) 85: 2444, 1988), by heuristic implementations of these algorithms such as, GAP, BESTFIT, FASTA, and TFASTA available as part of the GCG™ Wisconsin Package™ (Genetics Computer Group, Accelrys Inc., Burlington, Mass.), by heuristic implementations of these algorithms such as NCBI BLAST, WU-BLAST, BLAT, SIM, BLASTZ, or by manual inspection. As described above, an "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

For purposes of this invention, "percent identity" may also be determined using BLASTX version 2.0 for translated nucleotide sequences and BLASTN version 2.0 for polynucleotide sequences (or BLASTp for polypeptide sequences). In a preferred embodiment of the present invention, the presently disclosed gene regulatory sequences comprise protein, peptide, nucleic acid molecules or fragments having a BLAST score of more than 200, preferably a BLAST score of more than 300, and even more preferably a BLAST score of more than 400 with their respective homologues.

When two sequences have been identified for comparison, GAP and BESTFIT programs can be employed to determine their optimal alignment. For this purpose, the percent of sequence identity is preferably determined using the BESTFIT or GAP program of the Sequence Analysis Software Package™ (Version 10; Genetics Computer Group, Inc., Madison, Wis.). GAP utilizes the algorithm of Needleman and Wunsch (Needleman and Wunsch, *J Mol. Biol.* 48:443-453, 1970) to find the alignment of two sequences that maximizes the number of matches and minimizes the number of gaps. BESTFIT performs an optimal alignment of the best segment of similarity between two sequences and inserts gaps to maximize the number of matches using the local homology algorithm of Smith and Waterman (Smith and Waterman, *Adv. Applied Math.*, 2:482-489, 1981, Smith et al., *Nucl. Acids Res.* 11:2205-2220, 1983). The percent identity is most preferably determined using the BESTFIT program. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, preferably at least about 70%, preferably at least about 80%, more preferably at least about 85%, more preferably at least about 90%, even more preferably at least about 95%, and most preferably at least about 96%, 97%, 98% or 99% sequence identity compared to a reference sequence using the programs. Thus, according to one embodiment of the invention are protein, peptide, or polynucleotide molecules that have at least about 50% sequence identity, preferably at least about 70%, preferably at least about 80%, more preferably at least about 85%, more preferably at least about 90%, even more preferably at least about 95%, and most preferably at least about 96%, 97%, 98% or 99% sequence identity with a protein, peptide, or polynucleotide sequence described herein. Polynucleotide molecules that are capable of regulating transcription of operably linked transcribable polynucleotide molecules and have a substantial percent sequence identity to the polynucleotide sequences of the polynucleotide molecules provided herein are encompassed within the scope of this invention.

In one aspect of the invention, the present disclosure also provides polypeptides that are encoded by any of the polynucleotides of the invention described herein. Thus, the invention provides polypeptides of SEQ ID NOs: 2, 4, 6, 8, 10, 11, 13, 14, 16, 17, 19, 21, 23, 25, 27, 28, and 29. The invention also provides variants or fragments of the polynucleotides disclosed herein, and polypeptides encoded by any of the polynucleotide variants or fragments disclosed herein.

The endonuclease polypeptides of the present invention, including full-length polypeptides and biologically active fragments and fusion polypeptides, can be produced in genetically engineered host cells according to conventional techniques. Suitable host cells are those cell types that can be transformed or transfected with exogenous DNA and grown in culture, and include bacteria, insect cells, plant cells, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., 1989, supra; and Ausubel et al., eds., *Current Protocols in Molecular Biology*, John Wiley and Sons, Inc., NY, 1987.

In general, a nucleic acid sequence encoding an endonuclease polypeptide is operably linked to other genetic elements required for its expression, generally including a transcription promoter and terminator, within an expression vector or construct. The vector or construct will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct an endonuclease polypeptide into the secretory pathway of a host cell, a secretory signal sequence (also known as a leader sequence, pre sequence, or prepro sequence) can be included in the expression vector. The secretory signal sequence may be that of the native endonuclease polypeptide, or may be derived from another secreted protein or synthesized de novo. The secretory signal sequence is operably linked to the endonuclease-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., U.S. Pat. Nos. 5,037,743 and 5,143,830).

A variety of prokaryotic and eukaryotic cells are suitable host cells for the present invention, including but are not limited to microbial cells, algal cells, fungal cells, insect cells, mammalian cells, and plant cells. For example, when plants cells are used as hosts, the use of *Agrobacterium rhizogenes* as a vector for expressing genes in plant cells is well known in the field of plant biotechnology. Transformation of insect cells and production of foreign polypeptides therein is described extensively in, for example, U.S. Pat. No. 5,162,222 and WIPO publication WO 94/06463. Insect cells can be infected with recombinant baculovirus, commonly derived from *Autographa californica* nuclear polyhedrosis virus (AcNPV). See, e.g., D. R. et al., *Baculovirus Expression Vectors: A Laboratory Manual*, New York, Oxford University Press., 1994; and Richardson, Ed., *Baculovirus Expression Protocols. Methods in Molecular Biology*, Totowa, N.J., Humana Press, 1995. The second method of making recombinant baculovirus utilizes a transposon-based system described by Luckow et al. (*J Virol* 67:4566-79, 1993), Bac-to-Bac® Kit (Life Technologies, Inc., Carlsbad, CA). This system utilizes a transfer vector, pFastBacl™ (Life Technologies, Inc., Carlsbad, CA) containing a Tn7 transposon to move the DNA encoding a polypeptide of interest into a baculovirus genome maintained in *E. coli* as a large plasmid called a "bacmid." The pFastBac™ transfer vector utilizes the AcNPV polyhedrin promoter to drive the expression of the gene of interest, in this case a mismatch endonuclease. Further, pFastBacl™ (Life Technologies, Inc., Carlsbad, CA) can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, e.g., Hill-Perkins and Possee *J. Gen. Virol.* 71:971-6, 1990; Bonning et al., *J. Gen. Virol.* 75:1551-6, 1994; and, Chazenbalk and Rapoport, *J. Biol. Chem.* 270:1543-9, 1995. In such transfer vector constructs, a short or long version of the basic protein promoter can be used. Moreover, transfer vectors can be constructed to include secretory signal sequences derived from insect proteins. For example, a secretory signal sequence from Ecdysteroid Glucosyltransferase (EGT), honey bee melittin, or baculovirus gp67 can be used in recombinant nucleic acid constructs in accordance with the present invention. In addition, transfer vectors can include an in-frame fusion with DNA encoding an epitope tag at the C- or N-terminus of the expressed endonuclease polypeptide. Using techniques known in the art, a transfer vector containing an endonuclease of the present invention may be transformed into *E. coli*, and screened for bacmids which contain an interrupted lacZ gene indicative of recombinant baculovirus. The bacmid DNA containing the recombinant baculovirus genome can be isolated, using common techniques, and used to transfect *Spodoptera frugiperda* insect cells, e.g., Sf9 cells. Recombinant virus that expresses recombinant endonuclease can be subsequently produced. Recombinant viral stocks can be made by methods commonly used the art.

Fungal cells, including yeast cells are suitable as hosts for the present invention. Yeast species of particular interest in this regard include *Saccharomyces cerevisiae, Pichia pastoris*, and *Pichia methanolica*. Methods for transforming cells of these yeast species with exogenous DNA and producing recombinant polypeptides therefrom are well known in the art. See, for example, U.S. Pat. Nos. 4,599,311; 4,931,373; 4,870,008; 5,037,743; and 4,845,075. Transformed cells are selected by phenotype determined by the selectable marker, commonly drug resistance or the ability to grow in the absence of a particular nutrient (e.g., adenine or leucine). Suitable promoters and terminators for use in yeast include those from glycolytic enzyme genes (see, e.g., U.S. Pat. Nos. 4,599,311; 4,615,974; and 4,977,092) and alcohol dehydrogenase genes. See also U.S. Pat. Nos. 4,990, 446; 5,063,154; 5,139,936 and 4,661,454. The use of *Pichia methanolica* as host for the production of recombinant proteins is well known (see, e.g., PCT Publication Nos. WO199717450, WO199717451, WO199802536, and WO 91998/902565). Transformation systems for other yeasts, including *Hansenula polymorpha, Schizosaccharomyces pombe, Kluyveromyces lactis, Kluyveromyces fragilis, Ustilago maydis, Pichia* pastoris, *Pichia guillermondii* and *Candida maltosa* are also known in the art. See, for example, Gleeson et al., J. Gen. Microbiol. 132:3459-65, 1986 and U.S. Pat. No. 4,882,279. *Aspergillus* cells may be used as recombinant host cells according to a variety of known methods described in, for example, U.S. Pat. No. 4,935,349. Methods for transforming *Acremonium chrysogenum* and *Neurospora* sp. are also well known (see, e.g., U.S. Pat. Nos. 5,162,228; 4,486,533.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., Ibid.). When expressing an endonuclease polypeptide in bacteria such as *E. coli*, the polypeptide may be directed to the periplasmic space by a bacterial secretion sequence, or may be retained in the cytoplasm, typically as insoluble granules. In the former case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding. In the latter case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution.

In addition, cultured mammalian cells are also suitable hosts for the present invention. Methods for introducing exogenous DNA into mammalian host cells are well known and include, but are not limited to, liposome-mediated transfection (Hawley-Nelson et al., *Focus* 15:73, 1993; Ciccarone et al., *Focus* 15:80, 1993); calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973); electroporation (Neumann et al., *EMBO J.* 1:841-5, 1982), DEAE-dextran mediated transfection (Ausubel et al., ibid.), and viral vectors (Miller and Rosman, BioTechniques 7:980-90, 1989; Wang and Finer, *Nature Med.* 2:714-6, 1996). The production of recombinant polypeptides in cultured mammalian cells is described extensively in scientific literature and patent literature (see, e.g., U.S. Pat. Nos. 4,713,339; 4,784,950; 4,579,821; and 4,656,134). Suitable cultured mammalian cells include, but are not limited to, BHK (ATCC No. CRL 1632), BHK 570 (ATCC No. CRL 10314), COS-1 (ATCC No. CRL 1650), COS-7 (ATCC No. CRL 1651), 293 (ATCC No. CRL 1573; Graham et al., *J Gen. Virol.* 36:59-72, 1977) and Chinese hamster ovary (e.g., CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Methods for Correcting Errors in Nucleic Acid Molecules

In one aspect, embodiments or methods of the present invention provide a process for error correction in nucleic acid molecules. Errors arise in the replication, amplification, and/or synthesis of nucleic acid molecules. An "error" is a deviation from the nucleotide sequence that the nucleic acid molecules are intended to have, e.g., the desired sequence resulting from replication and/or amplification and/or synthesis procedures. Errors include deletions from, substitutions in, and additions to the desired nucleotide sequence, and may arise at any point in the synthesis by any mechanism.

The chemical synthesis of oligonucleotides is inherently subject to the occurrence of errors in nucleotide insertion due to the limitations of the chemistry involved, which generally has involved some type of solid-phase synthesis involving sequential addition of nucleotides to the 3' end of the growing molecule. The occurrence of incomplete reactions or side reactions places an upper limit on the length of nucleotides that can be synthesized, but even shorter nucleotides incorporate some rate of unintended or erroneous nucleotides.

The assembled nucleic acid molecules are double-stranded by default. Double-stranded nucleic acid molecules can be denatured and annealed by conventional methods. For example, heat denaturation of double-stranded nucleic acid molecules separates the double-stranded molecules into pairs of corresponding single-stranded molecules. Cooling the single-stranded molecules promotes their annealing into double-stranded molecules as individual nucleotides comprising the nucleic acid molecules coalesce into nucleotide base pairs along complementary stretches of nucleotide sequence. The kinetics or other physical or chemical parameters of denaturation and annealing may be controlled to promote mixing of the single-stranded molecules, so that the single-stranded molecules change partners. For example, if a double-stranded DNA molecule had a sequence error in both strands at the 400th nucleotide from one end, after denaturation and annealing, the single strands of that molecule may be paired with other single-stranded molecules lacking an error at that position, resulting in a nucleotide mismatch at that position. Thus, the denaturation and annealing process can produce double-stranded nucleic acid molecules with mismatches between nucleotide bases at sites of error. These mismatches can be targeted for removal, for example, by reacting annealed molecules with endonucleases having certain characteristics under appropriate conditions. A mismatch site or nucleotide mismatch site is a site on a double-stranded nucleic acid molecule where non-complementary base pairs are situated opposite each other. Nucleotide mismatch is caused by the erroneous insertion, deletion or mis-incorporation of bases that can arise during DNA replication or amplification. Examples of mismatched bases are G/T or A/C pairing or other deviations from standard G/C and A/T Watson-Crick base pairing. Mismatches can also be caused by tautomerization of bases during synthesis.

An aspect of the invention may be practiced to correct and reduce errors in double-stranded nucleic acid molecules. A first set of double-stranded nucleic acid molecules, which are intended to have a desired nucleotide sequence and a desired length, are reacted with one or more endonucleases. In one embodiment the endonuclease is a mismatch endonuclease that cuts the nucleic acids at or near the mismatch site, resulting in a nucleic acid molecule having a mismatched end. This can be accomplished by the selection of one or more appropriate endonucleases. The nucleic acid molecules having a mismatch are thus cut into smaller fragments that have a nucleotide mismatch at or near the end. The nucleic acids having the mismatch end are then treated with an endonuclease which cuts into the mismatch end and thus removes the mismatch. The resulting overhangs are then filled by the action of another enzyme, e.g., a DNA polymerase or other molecule having polymerase activity, and made into a fully double-stranded nucleic acid molecule. In one embodiment the process of denaturing, annealing, cutting with an appropriate endonuclease, and filling an overhang if necessary, can be repeated until the mismatch rate in the sample is insignificant, meaning that the rate of error is so low that it has no material effect on the outcome of the study for which the nucleic acids are being used. Nucleic acids having a mismatch at or near the end refers to a nucleic acid molecule having a mismatched nucleotide pair within 10 or less nucleotides of the end of the nucleic acid molecule. In other embodiments the mismatched nucleotide pair is present within 9 or less nucleotides of the end of the nucleic acid molecule, or within 8 or less, or within 7 or less, or within 6 or less, or within 5 or less, or within 4 or less, or within 3 or less, or within 2 or less, or within 1 nucleotide of the nucleotide mismatch.

FIG. 1 is a diagram showing a general illustration of a method of the invention. In this embodiment, error-free dsDNA molecules 101 are contained in a solution with dsDNA molecules having an error 103. Error-free dsDNA molecules are those having the "correct" desired nucleotide sequence, i.e., the desired sequence, whereas those dsDNA molecules having an error have an "incorrect" nucleotide in their sequence, i.e., that deviates from the desired sequence. The dsDNA molecules are denatured and then annealed, producing double-stranded nucleic acid molecules (dsDNA) with one or more errors or mismatches 105 in one of the single strands of the dsDNA. The dsDNA molecules are then exposed to the action of an endonuclease, thus cleaving the dsDNA into fragments. In some embodiments the endonuclease is a mismatch endonuclease that produces a dsDNA fragment having a mismatch at or near the end of the molecule 107. In the embodiment depicted in FIG. 1 the mismatch occurs at the 3' end of one of the single strands, but the mismatch can also occur at the 5' end depending on which endonuclease(s) are selected. In the embodiment depicted the nucleic acids are then exposed to the action of a 3' exonuclease, which "chews" away the 3' end of the molecule and thus removes the mismatch error by removing the incorrect nucleotide. The nucleic acid molecules are then again denatured, annealed, exposed to mismatch endonuclease, filled if desirable, and optionally amplified to produce error-free dsDNA molecules 111. The process can be repeated several times until the rate of error in the strands is insignificant. In some embodiments a ligase can be used to ligate the strands if desired.

Double-stranded nucleic acid molecules in the invention can be fragmented by reacting them with a unidirectional mismatch endonuclease. Unidirectional mismatch endonuclease refers to any molecule or combination of molecules having unidirectional mismatch endonuclease activity. In one embodiment the molecule is an enzyme, but the molecule can also be another molecule that is not an enzyme but that nevertheless has unidirectional endonuclease activity. The unidirectional mismatch endonucleases can be used either as a single endonuclease or as a mixture of endonucleases and other molecules. In one embodiment a single mismatch endonuclease enzyme in used, and in other embodiments a single mismatch endonuclease enzyme can be used in combination with another non-enzymatic molecule that is necessary for or enhances mismatch endonuclease activity.

As used herein, the term "mismatch endonuclease" refers to an enzyme activity that is able to both recognize a mismatch in a heteroduplex polynucleotide (e.g., a double-stranded nucleic acid molecule containing a nucleotide mismatch) and cut one or both strands of the heteroduplex at or near the mismatch. A molecule having unidirectional mismatch endonuclease activity consistently cuts on one side of the mismatch, either the 5' or 3' side, and not on the other side. In one embodiment the mismatch endonuclease is substantially unidirectional, meaning that at least 90% of the cuts are on one side of the mismatch, either the 5' or 3' side, but allowing for up to 10% of the cuts being on the opposing side. In various embodiments the mismatch endonucleases of the invention can recognize a nucleotide mismatch in the heteroduplex polynucleotide and cut both strands of the heteroduplex. In various embodiments the cut is introduced within 10 or less nucleotides of the nucleotide mismatch. In other embodiments the cut is introduced within 9 or less nucleotides, or 8 or less, or 7 or less, or 6 or less, or 5 or less, or 4 or less, or 3 or less, or 2 or less, or within 1 nucleotide of the nucleotide mismatch. In another embodiment the cut is introduced at the nucleotide mismatch site, thus leaving at least one of the mismatched nucleotides at the terminal end of the nucleic acid molecule. In one embodiment the mismatch endonuclease leaves a blunt end cut over both strands of the heteroduplex. When a blunt end is left at a nucleotide mismatch site the mismatched nucleotide pair is present at the end of the nucleic acid molecule. But in other embodiments the cuts can produce an overhang of one or more nucleotides such as, for example, 1 nucleotide or 2 or 3 or 4 or 5 or 6 or 7 or 8 or 9 or 10 or more than 10 nucleotides. Conventional methods are used to assemble these fragments into a second set of double-stranded nucleic acid molecules 111, which are overwhelmingly more likely to have the desired nucleotide sequence and desired length than were the first set of molecules.

A variety of mismatch endonucleases will find use in the present invention. RES I, CEL I, CEL II, SP nuclease, SP I endonuclease, T7 endonuclease, T4 endonuclease, endonuclease V, a Mut protein, are all useful mismatch endonucleases. One unidirectional mismatch endonuclease useful in the invention is commercially available as SURVEYOR® nuclease (Transgenomic, Inc., Omaha, NE), which uses CEL II as a principal component. It is also advantageous to utilize combinations of more than one of any of these. In a specific embodiment the mismatch endonuclease utilized is a combination of CEL I and CEL II mismatch endonucleases. Some of these have also been expressed recombinantly (CEL I and SP I) (Pimkin et al. *BMC Biotechnology*, 7:29 (2007). SP nuclease has been described by Doetsch et al. *Nucleic Acids Res.*, Vol. 16, No. 14 (1988).

In various embodiments a component can also be added to the reaction mixture to increase the action of endonucleases to create a double-stranded break in the nucleic acid molecule. Some endonucleases, e.g., endonuclease V, cleave only one strand of the nucleic acid molecule. But cleaving of both strands can be promoted by the inclusion in the medium of manganese ions, $Mn^{+2}$ at an appropriate concentration. In one embodiment the reaction medium includes about 10 nM $Mn^{+2}$ in a convenient form, e.g., $MnCl_2$. In another embodiment the additional step is taken to exclude magnesium $Mg^{+2}$ from the reaction medium.

Variants of the mismatch endonucleases disclosed herein are also useful in the invention. With reference to this disclosure the person of ordinary skill will realize many more endonucleases that will be useful in the present invention. It is also likely that new endonucleases having the required activity will be discovered or developed, and those can also find use in the application of the present invention. Thus, variants and homologs of the mismatch endonucleases disclosed herein are also useful in the invention. In various embodiments a protein having at least 70% sequence identity, or at least 75% sequence identity, or at least 80% sequence identity, or at least 85% sequence identity, or at least 90% sequence identity, or at least 95% or 96% or 97% or 98% or 99% sequence identity to any endonuclease disclosed herein is also useful in the invention. Thus, in two separate embodiments a protein having any of the above sequence identities to either CEL I or CEL II can be used in the invention.

In an alternative embodiment, the protein, peptide, or nucleic acid molecules useful in the invention comprise a protein, peptide, or nucleic acid sequence that exhibits 70% or greater identity, and more preferably at least 75% or greater, 80% or greater, 85% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater identity to a protein, peptide, or nucleic acid molecule selected from the group consisting of SEQ ID NO: 1 through SEQ ID NO: 33 in the Sequence Listing, any complements thereof, any fragments thereof, or any functional domain thereof. Thus, all variants and homologs of all endonucleases and exonuclease disclosed herein will be useful in this invention, and such variants and homologs can be discovered or designed using the principles disclosed herein.

For nucleic acids and polypeptides, the term "variant" is used herein to denote a polypeptide, protein or polynucleotide molecule with some differences, generated synthetically or naturally, in their base or amino acid sequences as compared to a reference polypeptide or polynucleotide, respectively. For example, these differences include substitutions, insertions, deletions or any desired combinations of such changes in a reference polypeptide or polynucleotide. Polypeptide and protein variants can further consist of changes in charge and/or post-translational modifications (such as glycosylation, methylation. phosphorylation, etc.). Biologically active variants of the polynucleotide sequences are also encompassed by the compositions of the present invention. Biologically active variants of the invention may be created by site-directed mutagenesis, induced mutation, or may occur as allelic variants (polymorphisms). Synthetic nucleotide sequences are those that are made through chemical processes in a laboratory environment. An example of a synthetic nucleotide is an oligonucleotide made using the known phosporamidite chemical synthesis. This chemical method joins nucleotides in the 3' to 5' direction using phosphoramidite building blocks derived from protected 2'-deoxynucleosides (dA, dC, dG, and T). Another process for creating synthetic nucleic acids is the polymerase chain reaction. Naturally produced oligonucleotides are synthesized either in Nature or in the laboratory using natural processes, such as the synthesis of an oligonucleotide by a microorganism. Synthetic nucleotide sequences can differ from naturally produced nucleotide sequences because the naturally produced sequences may have been processed through some post-transcriptional modification to result in a chemically changed nucleotide sequence. Synthetically produced oligonucleotides can be assembled from smaller oligonucleotides or subsets to form larger synthetic oligonucleotides.

The term "functional homolog" as used herein describes those proteins or polypeptides that have at least one characteristic in common. Such characteristics include sequence similarity, biochemical activity, transcriptional pattern similarity and phenotypic activity. Typically, a functional homolog is a polypeptide that has sequence similarity to a reference polypeptide, and that carries out one or more of the biological activities of the reference polypeptide. Functional homologs will typically give rise to the same characteristics to a similar, but not necessarily the same, degree. Typically, functionally homologous proteins give the same characteristics where the quantitative measurement due to one of the homologs is at least 20% of the other; more typically, between 30 to 40%; more typically, between 50-60%; even more typically, between 70 to 80%; even more typically, between 90 to 95%; even more typically, between 98 to 100% of the other.

A functional homolog and the reference polypeptide may be naturally occurring polypeptides, and the sequence similarity may be due to convergent or divergent evolutionary events. As such, functional homologs are sometimes designated in the literature as homologs, orthologs, or paralogs. Variants of a naturally-occurring functional homolog, such as polypeptides encoded by mutants or a wild-type coding sequence, may themselves be functional homologs. As used herein, functional homologs can also be created via site-directed mutagenesis of the coding sequence for a polypeptide, or by combining domains from the coding sequences for different naturally-occurring polypeptides. The term "functional homolog" sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of polypeptides. Sequence analysis can involve BLAST, Reciprocal BLAST, or PSI-BLAST analysis of non-redundant databases using amino acid sequence of a polypeptide as the reference sequence. Amino acid sequence is, in some instances, deduced from the nucleotide sequence. Typically, those polypeptides in the database that have greater than 40% sequence identity are candidates for further evaluation for suitability as a polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in the polypeptide of interest, e.g., conserved functional domains.

Conserved regions can be identified by locating a region within the primary amino acid sequence of a polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. A description of the information included at the Pfam database is described in, for example, Sonnhammer et al. (*Nucl. Acids Res.*, 26:320-322, 1998), Sonnhammer et al. (*Proteins*, 28:405-420, 1997); and Bateman et al. (*Nucl. Acids Res.*, 27:260-262, 1999). Conserved regions also can be determined by aligning sequences of the same or related polypeptides from closely related species. Closely related species preferably are from the same family. In some embodiments, alignment of sequences from two different species is adequate. Examples of domains indicative of the activity of the polypeptide of interest can be found in various literature sources and species, such as plants, algae, fungi, bacteria, and animals, which can be investigated.

Typically, polypeptides that exhibit at least 40% amino acid sequence identity are useful to identify conserved regions. Conserved regions of related polypeptides exhibit at least 45% amino acid sequence identity, e.g., at least 50%, at least 60%, at least 70%, at least 80%, or at least 90% amino acid sequence identity. In some embodiments, a conserved region exhibits at least 92%, 94%, 96%, 98%, or 99% amino acid sequence identity.

As used herein, the term "exonuclease" refers to an enzyme activity that removes nucleotides from one or more termini of a polynucleotide. In some embodiments the polynucleotide is bound to a second polynucleotide to form a double-stranded nucleic acid molecule. A molecule having unidirectional exonuclease activity proceeds to remove nucleotides in a 5' to 3' direction or a 3' to 5' direction in a stepwise manner. The molecule can be an enzyme, or another molecule that has exonuclease activity. A molecule having a substantially unidirectional exonuclease activity indicates that at least 90% of the nucleotides removed are on the 5' or 3' side of the nucleic acid molecule, and from 0% up to 10% are removed on the opposite side of the nucleic acid molecule. In one embodiment the exonuclease used in the method of the invention has the same directionality as the mismatch endonuclease used in the method.

A variety of exonucleases will be useful in the present invention. Exonuclease refers to any molecule having exonuclease activity, including both enzyme and non-enzyme molecules. In various embodiments the exonuclease is exonuclease III, a DNA polymerase having exonuclease activity, lambda exonuclease, T7 exonuclease, and T5 exonuclease, and variants thereof. The exonucleases can also be utilized in a combination of two or more of the exonucleases. DNA polymerases often have a 3' exonuclease activity, and one such DNA polymerase that is commercially available is the PHUSION® DNA polymerase (Finnzymes Oy, Espoo, Sweden). Other DNA polymerases with exonuclease activity include T4 DNA polymerase, phi29 polymerase. Variants and homologs of exonucleases disclosed herein can also find use in the present invention, and can be identified or discovered as disclosed herein.

Figure 2:
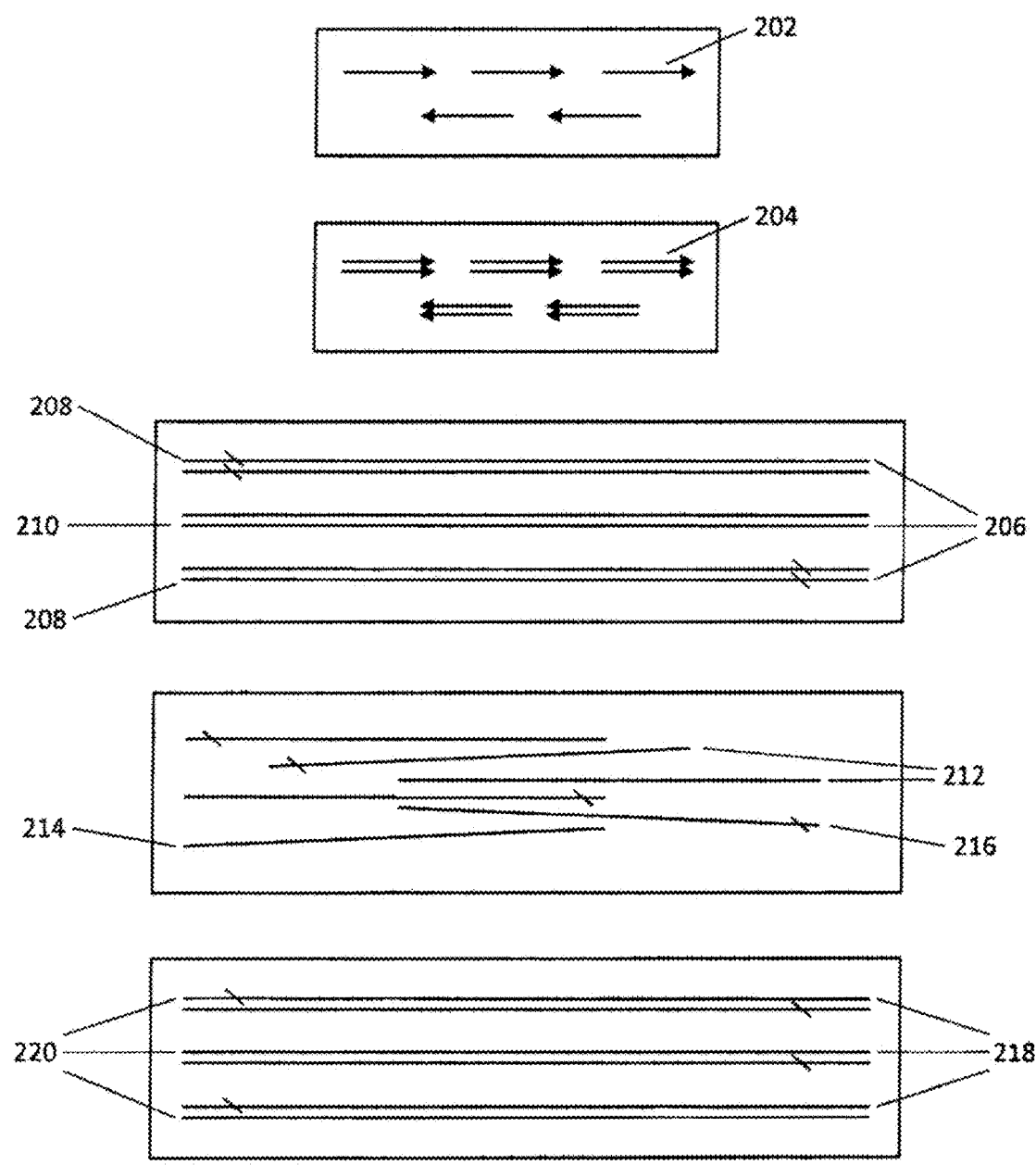
FIG. 2 provides a schematic illustration of steps of one embodiment of the present invention.

FIG. 2 depicts five distinct oligos 202 for the purpose of illustration, but any number of oligos may be used. The oligos may be obtained in any manner, including purchase from an industrial supplier and/or independent synthesis. Any number of oligos may be obtained in a manner different from that in which one or more other oligos are obtained. Any oligo may or may not be sequenced to determine whether it comprises enough molecules with the desired nucleotide sequence. Any of the oligos may optionally be further purified to reduce the number of any nucleotide-sequence errors they may bear.

In some embodiments, the oligos are obtained for both strands of the nucleic acid molecule that is intended to have a desired nucleotide sequence. Oligos 202 can be obtained for only a single strand of DNA that is intended to have a desired nucleotide sequence. In some embodiments oligos 202 may be obtained for both strands of DNA so that a set of oligos 202 comprises some oligos 202 having overlapping fragments of a full-length desired nucleotide sequence. A set of oligos 202 with such sequence overlaps can be used to assemble a full-length molecule intended to have a desired nucleotide sequence more efficiently than is otherwise possible. This increase in efficiency means that a smaller amount of full-length molecules (or even no full-length molecules) intended to have a desired nucleotide sequence may be used in order to obtain more full-length molecules intended to have a desired nucleotide sequence. This efficiency allows better control of the costs of nucleic acid molecule synthesis.

Referring to FIGS. 1 and 2, the oligos 202 are amplified into the oligos 204, increasing the number of molecules comprising each oligo 202. Each amplified oligo 204 is represented by a double arrow. The double arrow is merely a representational device: the number of molecules of each oligo 204 after amplification is not necessarily twice the number of molecules of each oligo 202 present before amplification, and is likely orders of magnitude greater. Any amplified oligo 204 may or may not be sequenced to determine whether it comprises enough molecules with the desired nucleotide sequence. Any amplified oligo 204 optionally may be further purified to reduce the number of any nucleotide sequence errors they may bear.

The amplified oligos 204 are used to assemble a first set of full length molecules 206 that are intended to have a desired nucleotide sequence. Double, parallel line-segments represent a full-length, double-stranded DNA molecule 206. Within a set of such full-length molecules 206, however, it is expected that there may be one or more molecules with one or more sequence errors 208. Sequence errors are denoted with a short slash along the full-length molecule 208. There may be many molecules 208 with one or more sequence errors at different points in the sequence. Within a set of such full-length molecules 206, it may also be expected that there are one or more molecules without any sequence errors 210.

The first set of dsDNA molecules 206 is denatured, so that the two strands of each molecule separate. The set of denatured, single-stranded, full-length molecules 212 thus may comprise one or more molecules without sequence errors 214, and one or more molecules with one or more sequence errors 216. There may be many molecules 216 with one or more sequence errors at different points in the sequence. The set of full-length molecules 206 may be denatured in any manner, for example, by heating the molecules 206.

The set of denatured molecules 212 is then annealed to obtain double-stranded DNA (dsDNA) molecules 218 that are intended to have a desired nucleotide sequence. Within a set of such dsDNA molecules, it may be expected that there are one or more molecules with one or more sequence errors, or mismatches in the dsDNA (220 and 105), and one or more molecules without any sequence errors or mismatches (not shown). The denatured set of single-stranded (ssDNA) molecules 212 may be annealed in any manner, for example, by cooling the molecules.

There may be many molecules (220 and 105) with one or more sequence errors or mismatches in dsDNA at different points in the sequence. The distribution of sequence errors over the second set of molecules 218 will most likely be different from that over the first set of molecules 206, since one or more single-stranded molecules 214 and 216 will anneal to other single-stranded molecules 214 and 216 different from those to which they were bound before denaturation. For example, a double-stranded molecule 208 in the first set of molecules 206 may have two sequence errors, one in each strand, are directly across from each other. During denaturation, a single strand 216 from the molecule 208 may move near a single-stranded molecule without errors 214. During annealing, a second full length molecule 220 may form that has an error in only one of its two strands.

The second set of full-length molecules 218 may be cut (e.g., by a mismatch endonuclease) to form a third set of molecules (not shown, but graphically depicted in FIG. 1 107), so that two or more molecules in the third set of molecules are shorter than full-length molecules 206 or 218. The cuts can occur wherever there is a mismatch in dsDNA. In one embodiment the cuts leave blunt ends and in other embodiments can leave sticky ends or overhangs. In one embodiment the endonuclease is one or more of the endonucleases that are unidirectional mismatch endonucleases disclosed herein. These endonucleases will cut dsDNA where there is a mismatch between the two strands of the dsDNA nucleic acid molecule. This will thus leave dsDNA having a mismatch at the end of the nucleic acid molecule, such as in nucleic acid 107 (shown as a blunt end cut embodiment). These dsDNA can then be digested with an exonuclease, for example a unidirectional exonuclease, that will "chew off" the end of the molecule and eliminate the incorrect nucleotide, resulting in a dsDNA with overhangs (109 in FIG. 1). These dsDNA can then be annealed and amplified and any gaps filled in with a polymerase. In some embodiments nicks can be repaired with a ligase if necessary.

With reference to this disclosure it can be seen that with each cycle of denaturation, annealing, and cutting with endonucleases and exonucleases, the number of sequence errors in the set of molecules is much lower than in the starting set of molecules. By providing a unique and powerful error-correction process operating late in the nucleic acid molecule synthesis process, the exemplary method for error correction of nucleic acid molecules yields a set of full-length molecules 111 intended to have a desired nucleotide sequence that has remarkably fewer errors than can be otherwise obtained.

Figure 3:
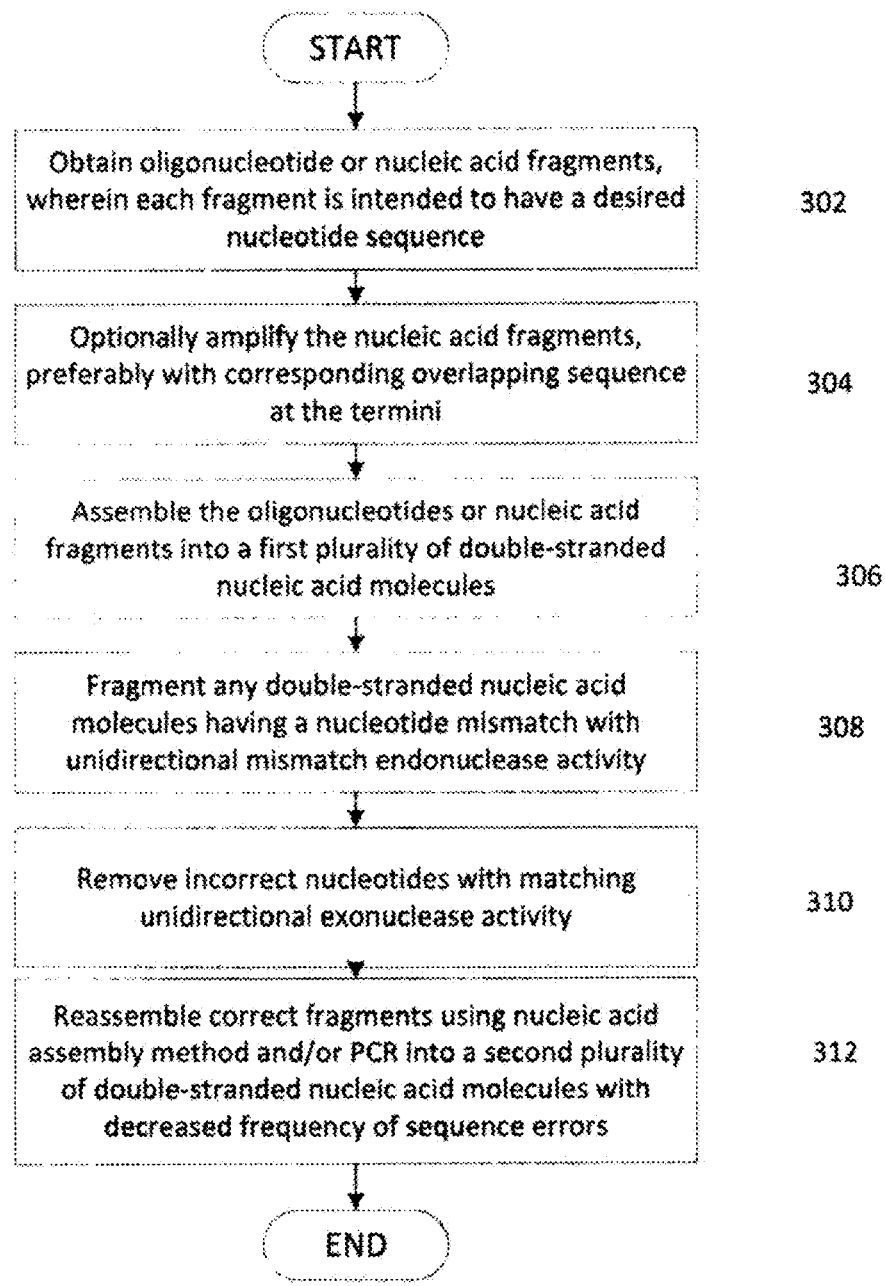
FIG. 3 provides a flow chart illustrating steps taken in one embodiment of the invention.

FIG. 3 is a flow chart depicting one embodiment of the method for synthesis of error-minimized nucleic acid molecules. At step 302, oligos 101 (FIG. 1) of a length smaller than that of the full-length desired nucleotide sequence (i.e., "oligonucleotide fragments" of the full-length desired nucleotide sequence) are obtained. Each oligo 101 is intended to have a desired nucleotide sequence that comprises a part of the full length desired nucleotide sequence. In various embodiments each oligo 101 may also be intended to have a desired nucleotide sequence that comprises an adapter primer for PCR amplification of the oligo 101, a tethering sequence for attachment of the oligo to a DNA microchip, or any other nucleotide sequence determined by any experimental purpose or other intention. The oligos may be obtained in any of one or more ways, for example, through synthesis, purchase, etc.

At step 304, the oligos 101 obtained are amplified to obtain more of each oligo. The amplification may be accomplished by any method, for example, by PCR. Introduction of additional errors into the nucleotide sequences of any of the oligos 103 may occur during amplification. The distinct amplified oligos result from the amplification at step 304. Oligos may be amplified by adapter primers, and the adapter sequence may be cleaved off by means of type IIS restriction endonucleases.

At step 306 the amplified oligos are assembled into a first plurality of double-stranded nucleic acid, which in one embodiment are intended to have a desired length that is the full length of the desired nucleotide sequence intended to be synthesized. Assembly of amplified oligos into full-length molecules may be accomplished in any way, for example, by using a PCR-based method. One or more of the double-stranded nucleic acid molecules (or full-length molecules) may be a double-stranded nucleic acid molecule containing at least one nucleotide mismatch (105), caused by one or more sequence errors in one or both of its strands. And one or more of the double-stranded nucleic acid molecules (or full length molecules) may be a double-stranded nucleic acid molecule containing no nucleotide mismatches or sequence errors in one of its single strands 105 (FIG. 1).

At step 308 the first plurality of double-stranded nucleic acid molecules are reacted with one or more endonucleases. In some embodiments the endonuclease is a unidirectional mismatch endonuclease, which fragments the double-stranded nucleic acid molecules having at least one nucleotide mismatch by cutting at or near the mismatched nucleotide pair. The one or more endonucleases thus cut the double-stranded nucleic acid molecules having a mismatch into shorter molecules that have a mismatch nucleotide pair at or near the terminal nucleotide of the nucleic acid molecule. In the case of a sticky end or overhang, the terminal nucleotide is the last nucleotide of the single stranded overhang. In the case of a blunt end cut, the terminal nucleotide will be either of the terminal pair of nucleotides of the nucleic acid molecule.

At step 310 of the embodiment of the methods the nucleotide mismatch is removed from the double-stranded nucleic acid molecules having a mismatch at or near the terminal nucleotide of the nucleic acid molecule by the action of a molecule having unidirectional exonuclease activity. In one embodiment the unidirectional exonuclease activity is of the same directionality as the unidirectional mismatch endonuclease activity. Thus, if the unidirectional mismatch endonuclease cleaves to the 3' side of the nucleotide pair mismatch, then the unidirectional exonuclease can chew away nucleotides at the 3' end of the nucleic acid strands comprising the nucleic acid molecule. The nucleotides that are chewed away by the exonuclease can then be replaced by the action of a polymerase either immediately or during the next optional replication/amplification phase. This then provides a fragmented error-free double-stranded nucleic acid molecule.

Finally in step 312 a second plurality of double-stranded nucleic acid molecules having the fragmented error-free double-stranded nucleic acid molecules 111 is assembled. This second plurality of double-stranded nucleic acid molecules has a decreased frequency of nucleotide mismatches as compared to the first plurality of double-stranded nucleic acid molecules.

In various embodiments of the invention the steps of the methods can be varied. For example in one embodiment the steps of fragmenting double-stranded nucleic acid molecules having a nucleotide mismatch, and the step of removing incorrect nucleotides with a matching unidirectional exonuclease can be performed sequentially as separate steps in a two-step reaction. But in other embodiments, one or more of the steps involved in the methods can be performed simultaneously. Thus, in one embodiment the reaction with endonuclease and exonuclease (e.g., steps 308 and 310 depicted in the embodiment in FIG. 2) can be performed simultaneously as a one-step reaction. This embodiment involves identifying reaction parameters where both the mismatch endonuclease and unidirectional exonuclease can perform their reactions in the same reaction. In a one-step reaction the reaction container does not need to be opened once all of the components necessary for the reaction have been added until the reaction is complete. In some embodiments the fragmentation step can be performed with SURVEYOR® nuclease (Transgenomic, Inc., Omaha, NE) and the exonuclease/error correction step performed with exonuclease III, and this combination of enzymes can be used in either a two-step or one-step procedure, as detailed in Example 3.

The present invention also provides compositions useful for performing the methods of the invention. The compositions can comprise (i) a molecule having a unidirectional mismatch endonuclease activity; and (ii) a molecule having unidirectional exonuclease activity of the same directionality as the unidirectional mismatch endonuclease activity in (i). In various embodiments the molecule having unidirectional mismatch endonuclease activity can be any described herein. The molecule having unidirectional exonuclease activity can also be any molecule having said activity described herein. The molecules can be combined in any combinations. In various examples the molecule having unidirectional mismatch endonuclease activity can be any of RES I, CEL I, CEL II, T7 endonuclease, T4 endonuclease, endonuclease V, a Mut protein, a variant of any thereof, and a combination of any two or more thereof. This molecule can be combined in a composition with a molecule having unidirectional exonuclease activity, for example, any of exonuclease III, a DNA polymerase, a variant of any thereof, or a combination of any two or more thereof. In different embodiments the composition can be provided in a dried form, or in a suitable buffer. The composition can also be provided in a tube, vial, or other suitable container. In one embodiment the molecules of (i) and (ii) are provided in a purified form in the container.

The present invention also provides kits useful in performing the methods of the invention. The kits may include any two or more of the following components: a mismatch endonuclease, a 5' or 3' exonuclease, a DNA polymerase (with or without 3' exonuclease proofreading activity), suitable buffers for performing the method, instructions for performing one or more methods of the invention, and information identifying a website that contains information about an error correction method of the invention. The information may be instructions for performing a method of the invention. In one embodiment the kit contains a unidirectional mismatch endonuclease and exonuclease III, each in a quantity sufficient to perform a method of the invention. The kits of the invention can also comprise any composition described herein. The endonucleases, exonucleases and DNA polymerases included in the kits can be any disclosed herein, such as SURVEYOR® nuclease (Transgenomic, Inc., Omaha, NE) or a generic substitute, exonuclease III, and PHUSION® DNA polymerase (Finnzymes Oy, Finland) or a generic substitute of any. The components of the kits can be provided in individual suitable containers, or can be provided with one or more components in a single container. The components of the kit can be provided in a purified form in the containers. The components of the kit can also be provided in dried form, or within a suitable buffer.

The present invention can also be utilized in conjunction with various techniques for the manipulation of nucleic acids. For example, in one embodiment the error correction techniques of the present invention can be utilized following or in conjunction with methods of joining nucleic acid molecules to ensure correct replication of nucleic acid molecules during the procedure. Examples include methods disclosed in US Patent Application No. 2010/0035768. Although any methods of assembly of nucleic acids would benefit from the addition of error correction methods as disclosed herein. The kits of the invention can therefore contain components for performing additional procedures and manipulations of DNA either before or after performing an error correction method of the invention. Therefore, in addition to the kit components described above, a kit may also include one or more of any of the following components: a non-thermostable 5' to 3' exonuclease that lacks 3' exonuclease activity (e.g., T5 exonuclease), a crowding agent (e.g., polyethylene glycol, a Ficoll), a thermostable non-strand displacing DNA polymerase with 3' exonuclease activity, a mixture of a said DNA polymerase and another DNA polymerase that lacks 3' exonuclease activity, and a thermostable ligase.

Throughout this disclosure, various information sources are referred to and incorporated by reference. The information sources include, for example, scientific journal articles, patent documents, textbooks, and World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

The discussion of the general methods given herein is intended for illustrative purposes only. Other alternative methods and embodiments will be apparent to those of skill in the art upon review of this disclosure, and are to be included within the spirit and purview of this application.

It should also be understood that the following examples are offered to illustrate, but not limit, the invention.

EXAMPLE 1

Assembly of Synthetic HA and NA Genes from Oligonucleotides

Synthetic gene products were assembled from a plurality of oligonucleotides with overlapping sequences at their terminal ends using Gibson Assembly™ (Synthetic Genomics, Inc., San Diego, CA) as previously described (see, e.g., US Patent Application No. 2010/0035768). Genes included representative hemagglutinin (HA) genes and representative neuraminidase (NA) genes.

Reagents

5× Isothermal (ISO) Buffer

The 5×ISO buffer contains 25% PEG-8000, 500 mM Tris-HCl pH 8.0, 50 mM MgCl2, 50 mM DTT, 1 mM each of the 4 dNTPs, and 5 mM NAD.

Six ml of this buffer can be prepared by combining the following:
- 3 ml of 1 M Tris-HCl pH 8.0
- 300 μl of 1 M MgCl2
- 600 μl of 10 mM dNTPs
- 300 μl of 1 M DTT (1.54 g dissolved in dH2O up to 10 ml)
- 1.5 g PEG-8000
- 300 μl of 100 mM NAD (Sigma; 0.66 g dissolved in dH2O up to 10 ml; resuspend by heating at 50° C. followed by continuous vortexing)

Add water to 6 ml, aliquot 1 ml and store at −80° C.

2× Assembly Master Mix

The 2× Assembly Master Mix contains the ISO reaction buffer and the enzymatic activities required for assembly of the component oligonucleotides into the gene products: 5× isothermal (ISO) reaction buffer) T5 exonuclease (Epicentre), PHUSION® DNA polymerase (Finnzymes Oy, Vantaa, Finland) and Taq DNA ligase.

800 μl of the 2× assembly master mix, sufficient for 80 reactions, can be prepared by combining the following:
- 320 μl 5×ISO buffer as prepared above
- 6.4 μl of 1 U/μl T5 exo (diluted 1:10 from enzyme stock in 1×T5 exo buffer)
- 20 μl of 2 U/μl PHUSION® polymerase (Finnzymes Oy, Vantaa, Finland)
- 80 μl of 40 U/μl Taq ligase
- 374 μl dH$_2$O Mix well and store at −20° C., or on ice if to be used immediately.

The assembly mixture can be stored at −20° C. for at least one year. The enzymes remain active following at least 10 freeze-thaw cycles. The mixture is ideal for the assembly of DNA molecules with 20-150 bp overlaps.

Oligonucleotides

Standard oligonucleotides were purchased at a concentration of 10,000 nM each. The entire HA gene sequence was covered using 52 oligonucleotides (oligos), and the entire NA gene sequence was covered using 44 NA oligonucleotides.

Assembly of Genes

For the assembly reactions 10 μl of each oligo was pooled, for a concentration of 192 nM per oligo (10,000 nM/52) for HA and 227 nM per oligo (10,000 nM/44) for NA. Oligo lengths were on average 60 bases with 30 bp overlaps.

Once pooled, 10 μl of this oligo mix was added to 10 μl of the 2× assembly master mix prepared as above. Reactions were incubated for 50° C. for 1 hour. Following assembly reactions, the gene products were amplified by PCR as follows:
- 5 μl assembly reaction
- 20 μl 5× PHUSION® HF Buffer (Finnzymes Oy, Vantaa, Finland)
- 2 μl 10 mM dNTPs
- 71 μl water
- 1 μl Hot Start PHUSION® Polymerase (Finnzymes Oy, Vantaa, Finland)
- 0.5 μl 100 uM RC-Univ-PKS10-F primer (universal forward primer for cloning vector)
- 0.5 μl 100 uM RC-Univ-PKS10-R primer (universal reverse primer for cloning vector)

Cycling reaction was as follows:
- 98° C. for 1 minute,
- 98° C. for 10 seconds, 60° C. for 30 seconds, 72° C. for 1.5 minutes,
- Repeated for 24 additional cycles, 72° C. for 5 minutes, and then kept at 4° C.

EXAMPLE 2

Cloning of Assembled Genes into Cloning Vector

In order to clone the assembled gene products into the PKS10 cloning vector, the plasmid was first amplified with primers to create matching overlapping sequences and the termini for a subsequent assembly reaction with the assembled gene product.

Preparation of Cloning Vector

The universal PKS10 cloning vector as amplified by PCR as follows:
- 20 μl 5× PHUSION® HF PCR Buffer
- 2 μl 10 mM dNTPs
- 75 μl water
- 1 μl Hot Start PHUSION® Polymerase (Finnzymes Oy, Vantaa, Finland)
- 1 μl 6 ng/μl PKS10 plasmid template
- 0.5 μl 100 uM Univ-PKS10-F primer
- 0.5 μl 100 uM Univ-PKS10-R primer Cycling reaction was as follows:
- 98° C. for 30 seconds,
- 98° C. for 10 seconds, 60° C. for 30 seconds, 72° C. for 3 minutes,
- Repeated for 29 additional cycles, 72° C. for 5 minutes, and then kept at 4° C.

The resulting PCR product was then gel purified using the QIAGEN® (Qiagen, GmbH, Hilden, Germany) gel purification kit. The typical yield for this PCR reaction was about 50 ng/μl.

Assembly of Synthetic Genes into Cloning Vector

PCR products of amplified synthetic genes or error-corrected synthetic genes were gel purified with the QIAGEN® gel purification kit, and used for assembly with the gel purified universal PKS10 vector PCR product as follows:
- 0.3 μl vector
- 4.7 μl HA or NA
- 5 μl 2× assembly master mix Reactions were incubated for 50° C. for 1 hour, and then 20 μl of water was added and mixed with the assembly reaction. This diluted assembly reaction mix was then used to transform E. coli by standard electroporation methods (Epicentre Epi300 cells). $\frac{1}{1000}^{th}$ of the 1 ml SOC outgrowth was plated onto LB Carbenicillin plates to obtain individual colonies.

A number of cultures of individual colonies were then grown, plasmid DNA was prepared, and then the sequence of the synthetic genes was determined using standard Sanger sequencing protocols. The percentage of clones containing the desired sequence was determined, and error rates were determined by multiplying the number of clones sequenced by the number of base pairs (bp) of DNA that was synthesized, then dividing this number by the total number of errors.

EXAMPLE 3

Error Correction of Synthetic HA and NA Genes Using a Mismatch Endonuclease Together with an Exonuclease Assembled HA and NA gene products were subjected to various error correction methods using combinations of an endonuclease enzyme and an exonuclease enzyme to remove inherent mismatches, primarily due to incorrect sequences within oligonucleotides incorporated in the assembled gene products. The result is a simple, high-fidelity, high efficiency gene synthesis of the HA and NA genes. Error rates were determined by multiplying the number of clones sequenced by the number of base pairs (bp) of DNA that was synthesized, then dividing this number by the total number of errors.

A. Two-Step Reactions

In the two-step reactions, the endonuclease enzyme reaction was performed first, followed by the exonuclease enzyme reaction. Following PCR of the assembled gene product as indicated in Example 1, the following reactions were performed.

SURVEYOR® nuclease/Exonuclease III

8 µl of the PCR product was denatured and annealed as follows:
98° C. for 2 minutes, slow cool to 85° C. at 2° C./second, hold at 85° C. for 2 minutes, slow cool to 25° C. at 0.1° C./second, hold at 25° C. for 2 minutes, and then hold at 10° C.

2 µl SURVEYOR® nuclease (Transgenomic, Inc., Omaha, NE) (a mismatch endonuclease derived from the celery plant that cleaves all types of mismatches) was added and incubated at 42° C. for 1 hour.

1 µl Exonuclease III (diluted 1 to 4000 in 1× HF Buffer) was added and incubated at 37° C. for 1 hour.

2 µl of this reaction mix was then amplified by PCR as described above.

Optionally, steps 1-3 were repeated to increase fidelity (to further reduce errors in the final gene product).

Results of Error Correction Using Two-Step Reactions

A synthetic HA gene was assembled from oligonucleotides and then subjected to error correction using SURVEYOR® nuclease alone, or SURVEYOR® nuclease followed by Exonuclease III in the two-step reaction above. The resultant error rates were as follows:

| Gene | Error Correction Method | Error Rate | Number of Correct Clones |
|---|---|---|---|
| HA | None | 1/1,791 bp | 11 out of 23 (48%) |
| HA | SURVEYOR® nuclease | 1/3,710 bp | 18 out of 29 (62%) |
| HA | SURVEYOR® nuclease + Exonuclease III | 1/5,572 bp | 21 out of 28 (75%) |

Thus, error correction of the synthetic HA gene increased the number of correct sequences obtained from 48% to 62% using SURVEYOR® nuclease treatment alone with an error rate improvement of 1/1,791 bp to 1/3,710 bp; and from 48% to 75% with an error rate improvement of 1/1,791 bp to 1/5,572 bp using the two-step error correction method combining an endonuclease enzyme with an exonuclease enzyme as disclosed.

In another experiment, both HA and NA synthetic genes were assembled from oligonucleotides and then subjected to error correction using SURVEYOR® nuclease alone, or SURVEYOR® nuclease followed by Exonuclease III in the two-step reaction above. The resultant error rates were as follows:

| Gene | Error Correction Method | Error Rate | Number of Correct Clones |
|---|---|---|---|
| HA | None | 1/1,635 bp | 2 out of 21 (9.5%) |
| HA | SURVEYOR® nuclease | 1/2,828 bp | 16 out of 30 (58.3%) |
| HA | SURVEYOR® nuclease + Exonuclease III | 1/6,169 bp | 22 out of 31 (71%) |
| NA | None | 1/1,850 bp | 13 out of 28 (46.4%) |
| NA | SURVEYOR® nuclease | 1/2,480 bp | 18 out of 31 (58.1%) |
| NA | SURVEYOR® nuclease + Exonuclease III | 1/5,314 bp | 24 out of 30 (80%) |

Thus, error correction of the synthetic HA gene increased the number of correct sequences obtained from 9.5% to 58.3% using SURVEYOR® nuclease treatment alone with an error rate improvement of 1/1635 bp to 1/2828 bp; and from 9.5% to 71% with an error rate improvement of 1/1635 bp to 1/6169 bp using the two-step error correction method combining an endonuclease enzyme with an exonuclease enzyme as disclosed.

Error correction of the synthetic NA gene increased the number of correct sequences obtained from 46.4% to 58.1% using SURVEYOR® nuclease (Transgenomic, Inc., Omaha, NE) treatment alone with an error rate improvement of 1/1850 bp to 1/2480 bp; and from 46.4% to 80% with an error rate improvement of 1/1850 bp to 1/5314 bp using the two-step error correction method combining an endonuclease enzyme with an exonuclease enzyme as disclosed.

Alternative Endonucleases+Exonuclease III

Reactions were performed as in the two-step procedure above but varying the endonuclease and conditions in step 2 as follows.

T4 endonuclease was substituted for SURVEYOR® nuclease, and incubated at 37° C. for 1 hour.

Endonuclease V was substituted for SURVEYOR® nuclease, and incubated at 37° C. for 1 hour.

Results of Error Correction Using Two-Step Reactions with Alternative Endonucleases

| Gene | Error Correction Method | Error Rate | Number of Correct Clones |
|---|---|---|---|
| HA | None | 1/876 bp | 3 out of 23 (13%) |
| HA | SURVEYOR® nuclease + Exonuclease III | 1/16,716 bp | 25 out of 28 (89%) |
| HA | T4 endonuclease + Exonuclease III | 1/2,239 bp | 11 out of 30 (37%) |
| HA | Endonuclease V + Exonuclease III | 1/1,327 bp | 3 out of 20 (15%) |

Thus, other alternative nucleases were able to increase the number of correct sequences obtained and improve the error rate to varying degrees in combination with an exonuclease enzyme as disclosed.

B. One-Step Reactions

In the one-step reactions, the endonuclease enzyme reaction was performed simultaneously (in the same reaction mixture at the same time) with the exonuclease enzyme reaction. Following PCR of the assembled gene product as indicated in Example 1, the following reactions were performed.

8 µl of the PCR product was denatured and annealed as follows:

98° C. for 2 minutes, slow cool to 85° C. at 2° C./second, hold at 85° C. for 2 minutes, slow cool to 25° C. at 0.1° C./second, hold at 25° C. for 2 minutes, and then hold at 10° C.

2 µl SURVEYOR® nuclease (Transgenomic, Inc., Omaha, NE) and 1 µl Exonuclease III, (diluted 1 to 4000 in 1× HF Buffer) were added and incubated at 42° C. for 1 hour.

2 µl of this reaction mix was then amplified by PCR as described above.

Optionally, steps 1 and 2 were repeated to increase fidelity.

Results of Error Correction Using One-Step Reactions

A synthetic HA gene was assembled from oligonucleotides and then subjected to error correction using SURVEYOR® nuclease (Transgenomic, Inc., Omaha, NE) together with Exonuclease III in the one-step reaction above. After the reaction components were added the reaction vessel was not opened again until the reaction had finished. The temperature of the incubation was varied from 4° C. to 50° C. to determine the optimal reaction conditions for the error correction. The resultant error rates were as follows:

| Gene | Temperature (° C.) | Error Rate | Number of Correct Clones |
|---|---|---|---|
| HA | 4 | 1/1,357 bp | 10 out of 25 (40%) |
| HA | 25 | 1/1,866 bp | 11 out of 25 (44%) |
| HA | 30 | 1/6,716 bp | 22 out of 30 (73%) |
| HA | 37 | 1/3,582 bp | 19 out of 30 (63%) |
| HA | 42 | 1/6,716 bp | 23 out of 30 (77%) |
| HA | 50 | 1/5,572 bp | 21 out of 28 (75%) |

Thus, the one-step error correction of the synthetic HA gene using the using SURVEYOR© nuclease together with Exonuclease III increased the number of correct sequences obtained and the error rates at various temperatures from 30° C. to 50° C. One-step error correction methods can be readily performed at 42° C.

EXAMPLE 4

Error Correction of Synthetic HA and NA Genes Using an Endonuclease Enzyme Alone or Together with an Exonuclease Enzyme or a Polymerase Enzyme Having Exonuclease Activity Assembled HA gene products were subjected to various error correction methods using combinations of various endonuclease enzymes alone or together with an exonuclease enzyme or a polymerase enzyme having exonuclease activity to remove inherent mismatches, primarily due to incorrect sequences within oligonucleotides incorporated in the assembled gene products.

SURVEYOR© nuclease (Transgenomic, Inc., Omaha, NE) (cuts 3? to mismatch) was used to perform error correction alone or in a two-step reaction as described above together with PHUSION© DNA polymerase (Finnzymes, Oy, Finland), which has 3? to 5? exonuclease activity. Reaction conditions were 42° C. for 20 minutes with SURVEYOR© nuclease, followed by 37° C. for 20 minutes with PHUSION© DNA polymerase.

T7 endonuclease (cuts 5? to mismatch) was used to perform error correction alone or in a two-step reaction as described above together with T5 exonuclease having 5? to 3? exonuclease activity. Reaction conditions were 37° C. for 20 minutes with T7 endonuclease, followed by 37° C. for 20 minutes with T5 exonuclease.

Results of Error Correction Using Two-Step Reactions with Alternative Endonucleases and Alternative Exonuclease Activities

| Gene | Error Correction Method | Error Rate | Number of Correct Clones |
|---|---|---|---|
| HA | None | 1/791 bp | 2 out of 19 (10.5%) |
| HA | SURVEYOR ® nuclease | 1/1,725 bp | 8 out of 26 (30.8%) |
| HA | SURVEYOR ® nuclease + PHUSION ® DNA polymerase | 1/2,217 bp | 13 out of 26 (50%) |
| HA | T7 endonuclease | 1/973 bp | 5 out of 25 (20%) |
| HA | T7 endonuclease + T5 exonuclease | 1/1,504 bp | 6 out of 21 (28.6%) |

Thus, other alternative nucleases were able to increase the number of correct sequences obtained and improve the error rate to varying degrees in combination with an exonuclease enzyme or another enzyme having exonuclease activity as disclosed.

EXAMPLE 5

Identification and Isolation of Genes Encoding Novel Mismatch Endonucleases

Several novel genes encoding novel mismatch endonucleases were identified and isolated. The nucleotide sequences of these genes together with the deduced amino acid sequences are provided in the accompanying Sequence Listing.

In a BLASTX homology analysis, the nucleotide sequence of each of the novel genes was determined to encode a protein having homology to known mismatch endonucleases. A homology search for the nucleotide sequences of the genes and the deduced amino acid sequences was also conducted using the DDBJ/GenBank/EMBL database. Additionally, sequence identity and similarity were also determined using GENOMEQUEST™ software (GenomeQuest, Inc., Westborough, MA) (Gene-IT, Worcester, MA). As reported in Table 1, the deduced amino acid sequence of each of the genes exhibited high sequence similarity with the amino acid sequences of known mismatch endonucleases CEL I and CEL II isolated from celery and *Selaginella lepidophlla* (U.S. Pat. Nos. 6,391,557; 7,078,211; and 7,560,261).

TABLE 1

Amino acid sequence homology to known endonucleases was calculated using the AlignX ® (Life Technologies, Carlsbad, CA) tool of the Vector NTI ® package (Life Technologies, Carlsbad, CA).

| Source Organism | RES I (SEQ ID NO: 02) | CEL I (SEQ ID NO: 04) | CEL II (SEQ ID NO: 06) | CEL II (SEQ ID NO: 08) |
|---|---|---|---|---|
| *Mimulus guttatus* (SEQ ID NO: 10) | 51% | 75% | 48% | 51% |

TABLE 1-continued

Amino acid sequence homology to known endonucleases was calculated using the AlignX ® (Life Technologies, Carlsbad, CA) tool of the Vector NTI ® package (Life Technologies, Carlsbad, CA).

| Source Organism | RES I (SEQ ID NO: 02) | CEL I (SEQ ID NO: 04) | CEL II (SEQ ID NO: 06) | CEL II (SEQ ID NO: 08) |
|---|---|---|---|---|
| Solanum tuberosum (SEQ ID NO: 13) | 50% | 74% | 46% | 50% |
| Vitis vinifera (SEQ ID NO: 16) | 52% | 51% | 73% | 74% |
| Vitis vinifera (SEQ ID NO: 23) | 50% | 50% | 68% | 72% |
| Solanum tuberosum (SEQ ID NO: 25) | 50% | 48% | 68% | 73% |
| Medicago sp. (SEQ ID NO: 27) | 51% | 51% | 67% | 71% |

FIG. 4 is an alignment of a *Selaginella lepidophlla* RES I endonuclease (SEQ ID NO: 02), a celery CEL I endonuclease (SEQ ID NO: 04), an *Apium* sp. CEL II endonuclease (SEQ ID NO: 06), another *Apium* sp. CEL II endonuclease (SEQ ID NO: 08), *Mimulus guttatus* CEL I endonuclease (SEQ ID NO: 10), a *Solanum tuberosum* CEL I endonuclease (SEQ ID NO: 13), a *Vitis vinifera* CEL II endonuclease (SEQ ID NO: 16), a *Solanum tuberosum* CEL II endonuclease (SEQ ID NO: 25), a *Medicago* sp. CEL II endonuclease (SEQ ID NO: 27). In this example the sequence alignment of FIG. 4 was generated using the program AlignX© (Life Technologies, Carlsbad, CA) of the Vector NTI Advance© (Invitrogen Corp., Carlsbad, CA) 11.5 package (Invitrogen, Carlsbad, Calif.) with default settings. As discussed in detail elsewhere herein, several polypeptide domains and motifs with high degree of conservation have been identified from this sequence comparison analysis. In the alignment figure shown herein, a dash in an aligned sequence represents a gap, i.e., a lack of an amino acid at that position. Black boxes and gray boxes identify identical amino acids and conserved amino acids, respectively, among aligned sequences.

In addition, using the program SignalP 4.0, a proteolytic cleavage site was predicted between the A30 and W31 of the full-length polypeptide of *Mimulus guttatus* CEL I endonuclease (SEQ ID NO: 10). As a result, the mature core region of *Mimulus guttatus* CEL I endonuclease, which was predicted to correspond to residues 31 to 306 of the amino acid sequence of SEQ ID NO: 10, was subsequently used for the production of recombinant of *Mimulus guttatus* CEL I endonuclease in insect cells as described in detail below, e.g., Examples 6, 7, and 8.

Similarly, the mature core region of *Vitis vinifera* CEL II endonuclease, predicted to correspond to residues 25 to 323 of the amino acid sequence of SEQ ID NO: 23, was subsequently used for the production of recombinant *Vitis vinifera* CEL II endonuclease in insect cells as described in Examples 6, 7, and 8 below.

EXAMPLE 6

Construction of Recombinant Expression Cassettes Suitable for Heterologous Enzyme Production in Recombinant Insect Cells This Example describes the construction of two recombinant expression cassettes to enable the heterologous expression of the mismatch endonucleases isolated from *Mimulus guttatus* and *Vitis vinifera* in insect cells by utilizing the Bac-to-Bac® Baculovirus Expression System (Life Technologies, Inc., Carlsbad, Calif.).

Two chimeric expression cassettes were designed for the recombinant expression of chimeric polypeptides containing the mature core region of either *Mimulus guttatus* CEL I endonuclease (SEQ ID NO: 14) or *Vitis vinifera* CEL II endonuclease (residues 25 to 323 of SEQ ID NO: 23). Each chimeric polypeptide contained a coding sequence of a mature core region that was operably linked to an N-terminal secretion signal for honeybee melittin (Tesier et al., Gene 98, 177-183), and a C-terminal 8× poly-Histidine epitope tag with linkers. The amino acid sequences of the chimeric proteins are disclosed in the Sequence Listing as SEQ ID NO: 11 and SEQ ID NO: 17.

The amino acid sequences of SEQ ID NO: 11 and SEQ ID NO: 17 were then used to generate expression cassettes having their DNA sequences codon optimized for expression in insect cells. For this purpose, the codon bias of *Spodoptera frugiperda* was used. The nucleotide sequences of the two codon-optimized expression cassettes are disclosed herein in the Sequence Listing as SEQ ID NO: 31 and SEQ ID NO: 33. Each of the recombinant expression cassettes were subsequently cloned into the expression vector pFastbac1 at the two cloning sites 5' EcoRI and 3' NotI. The resulting plasmids, which were named Mimmulus-C-His-pFastbac1 and *Vitis*-C-His-pFastbac1 respectively, were used to infect Sf9 insect cells. P1 baculovirus stocks were generated in Sf9 insect cells using the BAC-TO-BAC® System (Life Technologies, Inc., Carlsbad, CA) according to manufacturer's specifications.

EXAMPLE 7

Preparation of Solubilized Membrane Extracts of Insect Cells Expressing Recombinant Chimeric Endonucleases This Example describes details of the production of the recombinantly-expressed Mimmulus-C-His and *Vitis*-C-His endonucleases in cultures of insect cells by utilizing the BAC-TO-BAC® Baculovirus Expression System (Life Technologies, Inc., Carlsbad, Calif.). Briefly, P1 virus generation and heterologous production of the recombinant expression cassettes were performed according to the manufacturer's specifications. Cell lysates from P1 virus stock cultures for expression of the recombinant endonucleases were analyzed by Western blot assay using anti-His tag antibody as described below.

Preparation of Crude Solubilized Membrane Extracts from Insect Cell Cultures

Preparation of membranes: Cell pellet of each insect cell culture was resuspended in IMAC A buffer (20 mM Tris, 500 mM NaCl, 0.0125% Brij-35, 0.01% Triton X-100, 0.005% Tween-20, pH 8.0). The cell suspension was then sonicated (3×30 seconds, pulsing) and centrifuged at 18,000 rpm for 60 minutes, using a bench top centrifuge. The supernatant was decanted and the pellet was resuspended in 20 mM Tris-HCl, 150 mM NaCl, 5% glycerol. The protein concentration was quantitated and then diluted down to 10 mg/ml into the final buffer (50 mM Tris-HCl, 300 mM NaCl, 10 μM ZnCl2, 20% glycerol). The protein extract was aliquoted into 1 ml fractions and snap frozen using liquid nitrogen and stored at −80° C. To monitor cell lysis efficiency, SDS-PAGE gel assays (CRITERION™ Stain-Free precast PAGE system) (BioRad Laboratories, Inc., Hercules, CA) and Western Blot analysis (anti-HIS epitope antibody) were typically performed on whole-cell and resuspended pellet samples.

Both recombinant Mimmulus-C-His and Vitis-C-His endonucleases were found soluble in the following solubilization study. Insect cell pellets were resuspended 1:10 in 20 mM Tris-HCl, 150 mM NaCl. The resuspended protein was then broken into 4 equal tubes to create 4 conditions as follows:

I. 20 mM Tris-HCl, 150 mM NaCl
II. 20 mM Tris-HCl, 150 mM NaCl, 0.0125% Brij-35, 0.01% Triton X-100, 0.005% Tween-20
III. 20 mM Tris-HCl, 150 mM NaCl, 8M Urea
IV. 20 mM Tris-HCl, 150 mM NaCl, 0.0125% Brij-35, 0.01% Triton X-100, 0.005% Tween-20, 8 M Urea The four samples above were sonicated (3×15 seconds, on ice), and centrifuged at 18,000 rpm for 60 minutes using the bench top Allegra centrifuge. SDS-PAGE gel assays and Western Blot analysis were typically performed on whole-cell and resuspended pellet samples. Primary antibody was monoclonal anti-polyHistidine antibody produced in mouse, dilution: 1:3000; Secondary antibody was goat anti-mouse Peroxidase-conjugated; dilution: 1:20,000. Detection was performed with SUPERSIGNAL™ West Pico Chemiluminescent Substrate (Pierce Chemical Co., Rockford, IL).

Purification of Recombinant Mimmulus-C-his Endonuclease Expressed Heterologously in Insect Cells Each of the expression cassettes described in Example 6 contained a nucleotide sequence encoding a secretion signal for honeybee melittin which was operably linked to the nucleic acid sequence encoding the mature core region of the endonuclease. This feature allowed for the recombinant protein to be secreted into the culture media once it was produced in the cytoplasm of the insect cells.

1 L of insect cell culture in conditioned media was batch-bound overnight to 5 ml of Ni-SEPHAROSE®6 FF resin (Pharmacia Fine Chemicals, Piscataway, NJ). Resin was then collected by centrifugation, packed in a 5 ml column, and connected to an AKTA® Explorer (GE Health Care Biosciences, Inc., Uppsala, Sweden). The column was washed with 10CV of IMAC Buffer A (20 mM Tris 500 mM NaCl 5 mM Imidazole pH7.5). Bound protein was eluted with a linear 4% to 100% gradient of IMAC Buffer B over 30 CV (20 mM Tris, 500 mM NaCl, 1M Imidazole, pH7.5), collecting 2.5 ml fractions. The following samples were typically analyzed by SDS PAGE CRITERION™ Stain-Free (BioRad Laboratories, Inc., Hercules, CA) and Western blot with an anti-His antibody: (1) Elution fractions, (2) Load, (3) Flow Through (FT), and (4) Wash samples were. Protein containing fractions were pooled and dialyzed against final formulation buffer. (50 mM Tris, 30 mM NaCl, 10 µM ZnCl2, 20% glycerol, pH7.6). Dialyzed pool was filtered (0.45 µL) and analyzed by SDS PAGE CRITERION™ Stain Free and Western blot with an anti-His antibody. Protein concentration in protein samples was determined by UV spectrophotometry. The pool was dispensed into 1 ml aliquots, snap-frozen using liquid nitrogen and stored at −80° C. Final concentration of MimmulusC-His protein was 0.75 mg/ml. Total amount of protein from 1 L of cell culture was 9 mg. Formulation buffer was as follows: 50 mM Tris-HCl, 300 mM NaCl, 10 µM ZnCl2; 20% glycerol, pH 7.6.

Final concentration of MimmulusC-His protein was 0.75 mg/ml. Total amount of protein from 1 L of cell culture was 9 mg. Formulation buffer was as follows: 50 mM Tris-HCl, 300 mM NaCl, 10 µM ZnCl2; 20% glycerol, pH 7.6

Figures 5A, 5B:
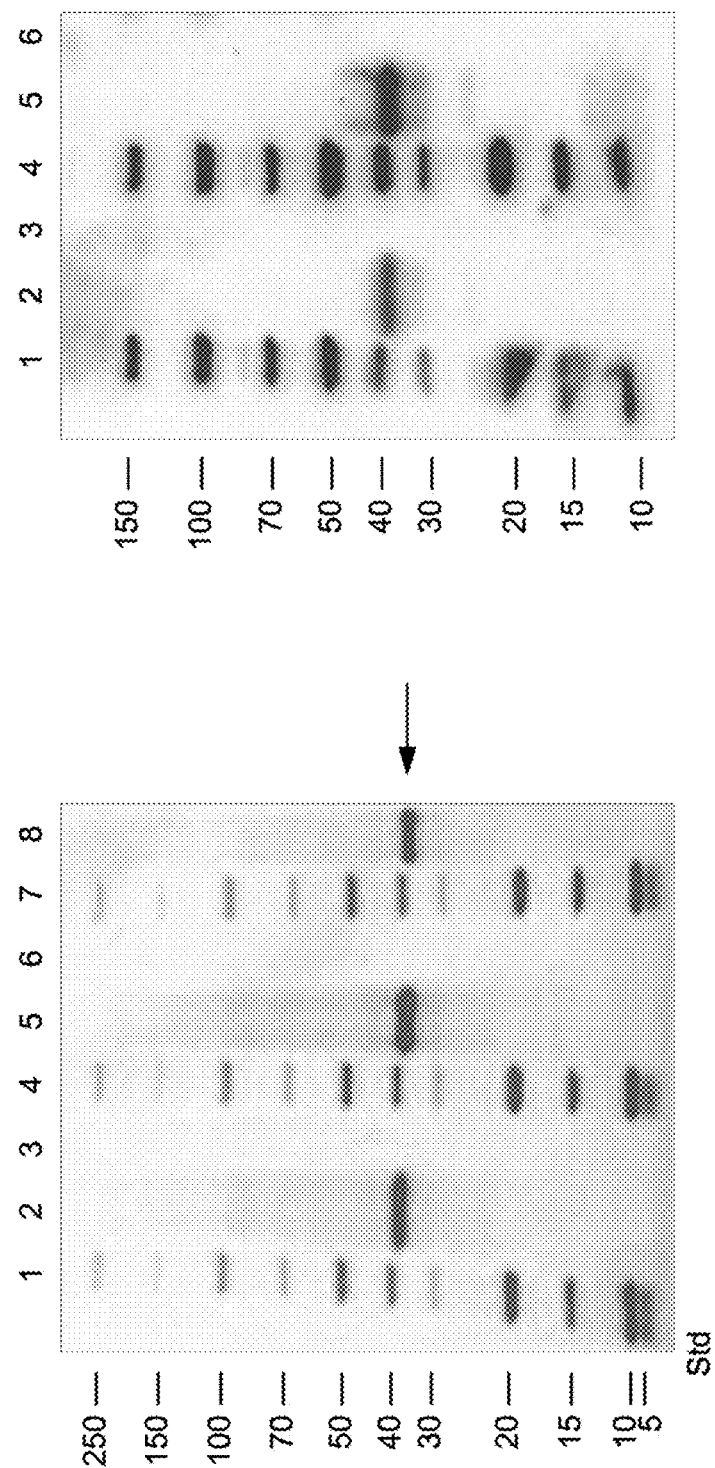
FIG. 5A depicts SDS polyacrylamide gel analysis of purified MimmulusC-His CEL I protein and FIG. 5B depicts Western Blot results using anti-polyHistidine antibody. Lane 1: Fermentas Marker (5 µL); Lane 2: MimmulusC-His Pre-Dialysis (12 µL); Lane 4: Fermentas Marker (12 µL); Lane 5: MimmulusC-His Post-Dialysis (12 µL); Lane 7: Fermentas Marker (5 µL); Lane 8: MimmulusC-His Post-Dialysis (6 µL).

FIGS. 5A and 5B depict SDS polyacrylamide gel analysis of purified MimmulusC-His CEL I protein (FIG. 5A) and Western Blot results using anti-polyHistidine antibody (FIG. 5B). Lane 1: Fermentas Marker (5 µL); Lane 2: MimmulusC-His Pre-Dialysis (12 µL); Lane 4: Fermentas Marker (12 µL); Lane 5: MimmulusC-His Post-Dialysis (12 µL); Lane 7: Fermentas Marker (5 µL); Lane 8: MimmulusC-His Post-Dialysis (6 µL). Primary antibody was monoclonal Anti-polyHistidine antibody produced in mouse, Dilution: 1:3000; Secondary antibody was goat anti-mouse Peroxidase-conjugated. Dilution: 1:20,000. Detection was performed with SUPERSIGNAL® West Pico Chemiluminescent Substrate (Pierce Chemical Co., Rockford, IL).

EXAMPLE 8

Error Correction of a Synthetic Gene Using Purified Mimulus C-his Chimeric Endonuclease Enzymes The purified recombinant Mimulus C-His chimeric endonuclease isolated as described in Example 7 above was subjected to various two-step error correction assays as described in Example 3, i.e., an endonuclease enzyme reaction was performed first, followed by an exonuclease enzyme reaction. Error rates were determined by multiplying the number of clones sequenced by the number of base pairs (bp) of DNA that was synthesized, then dividing this number by the total number of errors.

Briefly, a synthetic NA gene was assembled from oligonucleotides as indicated in Example 1 and then subjected to error correction using unpurified recombinant Mimulus C-His endonuclease, or purified recombinant Mimulus C-His endonuclease, followed by an exonuclease reaction as described in the two-step reaction above. In this experiment, either T5 exonuclease or Exonuclease III was used in the exonuclease treatment step. The resultant error rates were as follows:

TABLE 2

Error correction assays performed with unpurified recombinant *Mimulus* CEL I mature core derived from solubilized membrane extracts.

| Gene | Error Correction Method | Error Rate | Number of Correct Clones |
| --- | --- | --- | --- |
| NA | None | 1/1,572 bp | 12 out of 30 (40%) |
| NA | Unpurified recombinant *Mimulus* CEL I mature core | 1/2,801 bp | 23 out of 42 (55%) |
| NA | Unpurified recombinant *Mimulus* CEL I mature core + T5 exonuclease | 1/2,517 bp | 10 out of 20 (50%) |
| NA | Unpurified recombinant *Mimulus* CEL I mature core + Exonuclease III | 1/10,131 bp | 19 out of 23 (83%) |

Thus, error correction of the synthetic HA gene using unpurified recombinant Mimulus CEL I treatment alone provided an error rate improvement of 1/1,572 bp to 1/2,801 bp. Error rates were greatly improved using the two-step error correction method combining an endonuclease enzyme with an exonuclease enzyme as disclosed in TABLE 2. In particular, a combination of unpurified recombinant Mimulus CEL I mature core and Exonuclease III increased the number of correct sequences obtained from 40% to 83%, and provided an error rate improvement of 1/1,572 bp to 1/10,131 bp.

In another experiment, both unpurified and purified Mimulus CEL I endonucleases were tested in two-step error correction assays. In this experiment, an HA synthetic gene was assembled from oligonucleotides and then subjected to error correction using Mimulus CEL I endonuclease (42° C., 1 hour), followed by Exonuclease III treatment (55° C., 1 hour) in a two-step reaction as described in Example 3. The resultant error rates were as follows:

TABLE 3

Error correction assays performed with recombinant Mimulus CEL I mature core purified by Ni-SEPHAROSE ® column chromatography (Pharmacia Fine Chemicals, Piscataway, NJ).

| Gene | Error Correction Method | Error Rate | Number of Correct Clones |
|---|---|---|---|
| NA | None | 1/1,204 bp | 8 out of 32 (25%) |
| NA | Unpurified recombinant Mimulus CEL I mature core + Exonuclease III | 1/3,081 bp | 25 out of 42 (59.5%) |

TABLE 3-continued

Error correction assays performed with recombinant Mimulus CEL I mature core purified by Ni-SEPHAROSE ® column chromatography (Pharmacia Fine Chemicals, Piscataway, NJ).

| Gene | Error Correction Method | Error Rate | Number of Correct Clones |
|---|---|---|---|
| NA | Purified recombinant Mimulus CEL I mature core + Exonuclease III | 1/13,570 bp | 33 out of 37 (89%) |

Thus, error correction of the synthetic HA gene increased the number of correct sequences obtained from 25% to 59.5% using unpurified recombinant Mimulus CEL I mature core alone with an error rate improvement of $1/1{,}204$ bp to $1/3{,}081$ bp; and from 25% to 89% with an error rate improvement of $1/1{,}204$ bp to $1/13{,}570$ bp using the two-step error correction method combining an endonuclease enzyme with Exonuclease III treatment.

```
                        SEQUENCES
Exemplary Endonuclease - RES I
U.S. Pat. No. 7,078,211- SEQ ID NO: 01 - Nucleic Acid Sequence
>RES I_US7078211_SEQIDNO_01
ATGGCAACGACCAAGACGAGCGGGATGGCGCTGGCTTTGCTCCTCGTCGCCGCCCTGGCC

GTGGGAGCTGCGGCCTGGGGGAAAGAGGGCCATCGCCTCACTTGTATGGTCGCCGAGCCC

TTTCTAAGCTCTGAATCCAAGCAAGCTGTGGAGGAGCTTCTCTCTGGAAGAGATCTCCCG

GACTTGTGTTCATGGGCCGATCAGATTCGAAGATCGTATAAGTTTAGATGGACTGGTCCT

TTGCACTACATCGATACTCCAGACAACCTCTGCACCTATGACTATGATCGTGACTGCCAC

GATTCCCATGGGAAGAAGGACGTGTGTGTCGCTGGTGGGATCAACAATTACTCGTCGCAG

CTGGAAACGTTTCTAGATTCAGAGAGCTCGTCGTATAACTTGACCGAGGCGCTGCTCTTC

CTGGCTCACTTTGTCGGGGATATACACCAGCCCTTGCACGTAGCATTTACGAGTGATGCC

GGAGGCAATGGCGTGCACGTCCGCTGGTTTGGACGAAAGGCCAACTTGCATCACGTCTGG

GATACAGAATTTATTTCTAGAGCCAATCGTGTGTACTACCACGACATTTCCAAGATGCTC

CGGAACATTACCAGGAGCATAACTAAGAAGAATTTCAATAGTTGGAGCAGATGTAAGACT

GATCCGGCGGCTTGTATTGATAGTTATGCGACAGAAAGTATAGATGCTTCTTGCAACTGG

GCATACAAAGACGCACCCGACGGAAGCTCTCTAGATGATGATTACTTCTCTTCACGCCTT

CCAATTGTTGAGCAGCGTCTTGCTCAAGGGGCGTCAGGCTGGCGTCAATACTCAACAGG

ATTTTTGGAGGAGCAAAGTCGAACAGGTCCAGTCGCTCAAGCATGTAG

U.S. Pat. No. 7,078,211- SEQ ID NO: 02 - Amino Acid Sequence
>RES I_US7078211_SEQIDNO_02
MATTKTSGMALALLLVAALAVGAAAWGKEGHRLTCMVAEPFLSSESKQAVEELLSGRDLP

DLCSWADQIRRSYKFRWTGPLHYIDTPDNLCTYDYDRDCHDSHGKKDVCVAGGINNYSSQ

LETFLDSESSSYNLTEALLFLAHFVGDIHQPLHVAFTSDAGGNGVHVRWFGRKANLHHVW

DTEFISRANRVYYHDISKMLRNITRSITKKNFNSWSRCKTDPAACIDSYATESIDASCNW

AYKDAPDGSSLDDDYFSSRLPIVEQRLAQGGVRLASILNRIFGGAKSNRSSRSSM

Exemplary Endonuclease - CEL I
U.S. Pat. No. 6,391,557- SEQ ID NO: 03 - Nucleic Acid Sequence
>CEL I_US6391557_SEQIDNO_03
TACTCACTATAGGGCTCGAGCGCCCGCCCGGGCAGGTATAATATTAGACTTGTACTCAAT

GACAAGCGCCATCTATGAGTTTCATCATGCCTATATATAAACACATGAACCTGTCATTGT

TCATTTATGCATTATTGTTGTATTAGCTGAAAAATTTCTGGCAAATGACGCGATTATATT

CTGTGTTCTTTCTTTTGTTGGCTCTTGTAGTTGAACCGGGTGTTAGAGCCTGGAGCAAAG
```

-continued

```
AAGGCCATGTCATGACATGTCAAATTGCGCAGGATCTGTTGGAGCCAGAAGCAGCACATG

CTGTAAAGATGCTGTTACCGGACTATGCTAATGGCAACTTATCGTCGCTGTGTGTGTGGC

CTGATCAAATTCGACACTGGTACAAGTACAGGTGGACTAGCTCTCTCCATTTCATCGATA

CACCTGATCAAGCCTGTTCATTTGATTACCAGAGAGACTGTCATGATCCACATGGAGGGA

AGGACATGTGTGTTGCTGGAGCCATTCAAAATTTCACATCTCAGCTTGGACATTTCCGCC

ATGGAACATCTGATCGTCGATATAATATGACAGAGGCTTTGTTATTTTTATCCCACTTCA

TGGGAGATATTCATCAGCCTATGCATGTTGGATTTACAAGTGATATGGGAGGAAACAGTA

TAGATTTGCGCTGGTTTCGCCACAAATCCAACCTGCACCATGTTTGGGATAGAGAGATTA

TTCTTACAGCTGCAGCAGATTACCATGGTAAGGATATGCACTCTCTCCTACAAGACATAC

AGAGGAACTTTACAGAGGGTAGTTGGTTGCAAGATGTTGAATCCTGGAAGGAATGTGATG

ATATCTCTACTTGCGCCAATAAGTATGCTAAGGAGAGTATAAAACTAGCCTGTAACTGGG

GTTACAAAGATGTTGAATCTGGCGAAACTCTGTCAGATAAATACTTCAACACAAGAATGC

CAATTGTCATGAAACGGATAGCTCAGGGTGGAATCCGTTTATCCATGATTTTGAACCGAG

TTCTTGGAAGCTCCGCAGATCATTCTTTGGCATGAATTTAGATACTGATATTCGCATTTC

TCATGACACCCTTCTCTTATGCAATTTGCAGATCAGCTGTGATTCACTAATTGAA

U.S. Pat. No. 6,391,557- SEQ ID NO: 04 - Amino Acid Sequence
>CEL I_US6391557_SEQIDNO_04
MTRLYSVFFLLLALVVEPGVRAWSKEGHVMTCQIAQDLLEPEAAHAVKMLLPDYANGNLS

SLCVWPDQIRHWYKYRWTSSLHFIDTPDQACSFDYQRDCHDPHGGKDMCVAGAIQNFTSQ

LGHFRHGTSDRRYNMTEALLFLSHFMGDIHQPMHVGFTSDMGGNSIDLRWFRHKSNLHHV

WDREIILTAAADYHGKDMHSLLQDIQRNFTEGSWLQDVESWKECDDISTCANKYAKESIK

LACNWGYKDVESGETLSDKYFNTRMPIVMKRIAQGGIRLSMILNRVLGSSADHSLA

Exemplary Endonucleases - CEL II
U.S. Pat. No. 7,560,261- SEQ ID NO: 05 - Nucleic Acid Sequence
>CEL II_US7560261_SEQIDNO_05
ATGGGTATGTTGACTTATACTGGAATTTATTTTCTGCTATTACTTCCAAGTGTTTTCTGT

TGGGGAAAACAAGGACATTTTGCAATTTGTAAAATTGCCCAGGGGTTCCTTAGTAAAGAT

GCACTGACTGCAGTGAAAGCATTGCTCCCAGAATATGCAGATGGTGATCTAGCAGCTGTT

TGCTCCTGGGCTGACGAGGTTCGATTTCATATGCGTTGGAGTAGCCCATTACATTATGTG

GACACGCCTGATTTCAGGTGTAACTATAAATACTGTAGAGATTGCCATGATTCTGTTGGA

CGGAAAGACCGGTGTGTTACTGGAGCAATTCACAACTACACAGAGCAACTTCTATTGGGT

GTTCATGACTTGAATTCAAAAATGAATAACAACTTGACGGAGGCACTTATGTTCTTATCA

CATTTCGTTGGTGATGTCCATCAGCCTCTACATGTTGGCTTCCTTGGCGATGAAGGAGGA

AACACAATCACCGTCCGCTGGTATCGGAGGAAAACCAATTTGCATCATGTATGGGACACA

ATGATGATTGAATCCTCCTTGAAGACATTCTACAATTCAGATCTTTCTAGCTTAATACAA

GCTATTCAGAGCAATATTACAGGTGTCTGGCTTACCGACAGCTTATCTTGGAGCAATTGC

ACTGCTGATCATGTGGTTTGTCCAGACCCGTATGCTTCTGAAAGCATTGAGTTGGCCTGC

AAGTTTGCCTACAGAAATGCCACACCTGGGACCACTTTAGGAGATGAGTACTTCCTCTCT

CGGTTGCCTGTTGCGGAGAAGAGGTTGGCTCAGGCTGGGGTCCGTTTGGCTGCTACTCTT

AACCGAATCTTCACTTCAAACCCCAGCGATCTCACAAGATTGAATATGCATAATGGTGGA

CATAGAAGCAGTAACAATATTGAAATAGTGTAA
```

-continued

U.S. Pat. No. 7,560,261- SEQ ID NO: 06 - Amino Acid Sequence
>CEL II_US7560261_SEQIDNO_06
MGMLTYTGIYFLLLLPSVFCWGKQGHFAICKIAQGFLSKDALTAVKALLPEYADGDLAAV

CSWADEVRFHMRWSSPLHYVDTPDFRCNYKYCRDCHDSVGRKDRCVTGAIHNYTEQLLLG

VHDLNSKMNNNLTEALMFLSHFVGDVHQPLHVGFLGDEGGNTITVRWYRRKTNLHHVWDT

MMIESSLKTFYNSDLSSLIQAIQSNITGVWLTDSLSWSNCTADHVVCPDPYASESIELAC

KFAYRNATPGTTLGDEYFLSRLPVAEKRLAQAGVRLAATLNRIFTSNPSDLTRLNMHNGG

HRSSNNIEIV

U.S. Pat. No. 7,560,261- SEQ ID NO: 07 - Nucleic Acid Sequence
>CEL II_US7560261_SEQIDNO_07
TGGGGAAAACAAGGACATTTTGCAATTTGTAAAATTGCCCAGGGGTTCCTTAGTAAAGAT

GCACTGACTGCAGTGAAAGCATTGCTCCCAGAATATGCAGATGGTGATCTAGCAGCTGTT

TGCTCCTGGGCTGACGAGGTTCGATTTCATATGCGTTGGAGTAGCCCATTACATTATGTG

GACACGCCTGATTTCAGGTGTAACTATAAATACTGTAGAGATTGCCATGATTCTGTTGGA

CGGAAAGACCGGTGTGTTACTGGAGCAATTCACAACTACACAGAGCAACTTCTATTGGGT

GTTCATGACTTGAATTCAAAAATGAATAACAACTTGACGGAGGCACTTATGTTCTTATCA

CATTTCGTTGGTGATGTCCATCAGCCTCTACATGTTGGCTTCCTTGGCGATGAAGGAGGA

AACACAATCACCGTCCGCTGGTATCGGAGGAAAACCAATTTGCATCATGTATGGGACACA

ATGATGATTGAATCCTCCTTGAAGACATTCTACAATTCAGATCTTTCTAGCTTAATACAA

GCTATTCAGAGCAATATTACAGGTGTCTGGCTTACCGACAGCTTATCTTGGAGCAATTGC

ACTGCTGATCATGTGGTTTGTCCAGACCCGTATGCTTCTGAAAGCATTGAGTTGGCCTGC

AAGTTTGCCTACAGAAATGCCACACCTGGGACCACTTTAGGAGATGAGTACTTCCTCTCT

CGGTTGCCTGTTGCGGAGAAGAGGTTGGCTCAGGCTGGGGTCCGTTTGGCTGCTACTCTT

AACCGAATCTTCACTTCAAACCCCAGCGATCTCACAAGATTGAATATGCATAATGGTGGA

CATAGAAGCAGTAACAATATTGAAATAGTGTAA

U.S. Pat. No. 7,560,261- SEQ ID NO: 08 - Amino Acid Sequence
>CEL II_US7560261_SEQIDNO_08
WGKQGHFAICKIAQGFLSKDALTAVKALLPEYADGDLAAVCSWADEVRFHMRWSSPLHYV

DTPDFRCNYKYCRDCHDSVGRKDRCVTGAIHNYTEQLLLGVHDLNSKMNNNLTEALMFLS

HFVGDVHQPLHVGFLGDEGGNTITVRWYRRKTNLHHVWDTMMIESSLKTFYNSDLSSLIQ

AIQSNITGVWLTDSLSWSNCTADHVVCPDPYASESIELACKFAYRNATPGTTLGDEYFLS

RLPVAEKRLAQAGVRLAATLNRIFTSNPSDLTRLNMHNGGHRSSNNIEIV

Exemplary Endonucleases - CEL I Variant - *Mimulus guttatus*
Nucleic Acid Sequence
SEQ ID NO: 09
ATGCAGATGTCGATTTCACGAGGAATTTTTGTTTCTTATTTTGCTTTATTTCTTTGTGTT

TGTGTTGTTTATGAACCTTGTGTCCAGGCATGGAGTAAAGAAGGTCATTCCATGACATGC

AAAATTGCTCAGGATTTGCTGGGACCAGAGGCGAAGCATGCTGTCCAAATGCTGTTACCT

GAAAATGTTAATGGTGATTTATCGGCACTTAGCGTGTGGCCTGACCAAGTAAGACACTGG

TATAAGTACCGTTGGACGAGCCCTCTTCACTTCATAGACACACCAGATCAAGCCTGTAAT

TTCAATTATCAGAGGGATTGCCATGATCCACATGGTGTTAAGGGTATGTGTGTAGCGGGG

GCAATTCAGAACTTCACCAATCAGCTTTCGCATTATCGGCACGGAACCTCTGATCGACGC

TATAATATGACAGAGGCCTTGTTGTTCTTGGCACACTTCATGGGAGATATTCATCAGCCA

CTGCATGTTGGATTCACGAGTGACGAAGGAGGAAACACTATAGACTTGCGCTGGTTCAGA

CACAAGTCAAATCTGCACCATGTATGGGACAGAGAGATAATTCTTACAGCTGCAGCAGAT

```
-continued
TACTACGGAAAGGACATTGACCTCCTGCAAGAAGACATTAAGGGAAACTTCACTGATGGA

ATCTGGTCTGGTGATCTTGCCTCTTGGAGGGAATGCAGTGATATATTTTCTTGTGTCAAC

AAGTATGCTGCTGAGAGTATAAACATGGCCTGCAAATGGGGTTACAAAGATGTTAAATCA

GGGGACACTCTTTCAGATGATTACTTTAATTCAAGATTGCCGATTGTTATGAAACGCATA

GCTCAGGGTGGAGTCCGTTTAGCTATGATTTTGAACCGGGTTTTCGGTGATAGCAAAGAG

GATTCCTTAATTGCTACTTAA

Amino Acid Sequence
                                                    SEQ ID NO: 10
MQMSISRGIFVSYFALFLCVCVVYEPCVQAWSKEGHSMTCKIAQDLLGPEAKHAVQMLLP

ENVNGDLSALSVWPDQVRHWYKYRWTSPLHFIDTPDQACNFNYQRDCHDPHGVKGMCVAG

AIQNFTNQLSHYRHGTSDRRYNMTEALLFLAHFMGDIHQPLHVGFTSDEGGNTIDLRWFR

HKSNLHHVWDREIILTAAADYYGKDIDLLQEDIKGNFTDGIWSGDLASWRECSDIFSCVN

KYAAESINMACKWGYKDVKSGDTLSDDYFNSRLPIVMKRIAQGGVRLAMILNRVFGDSKE

DSLIAT

Amino Acid Sequence for Insect Cell Expression
                                                    SEQ ID NO: 11
MKFLVNVALVFMVVYISYIYAWSKEGHSMTCKIAQDLLGPEAKHAVQMLLPENVNGDLSA

LSVWPDQVRHWYKYRWTSPLHFIDTPDQACNFNYQRDCHDPHGVKGMCVAGAIQNFTNQL

SHYRHGTSDRRYNMTEALLFLAHFMGDIHQPLHVGFTSDEGGNTIDLRWFRHKSNLHHVW

DREIILTAAADYYGKDIDLLQEDIKGNFTDGIWSGDLASWRECSDIFSCVNKYAAESINM

ACKWGYKDVKSGDTLSDDYFNSRLPIVMKRIAQGGVRLAMILNRVFGDSKEDSLIATGSH

HHHHHHG
Underlined—honeybee melittin secretion signal; polyhistidine
tag with linkers Exemplary Endonucleases - CEL I Variant - Solanum tuberosum
Nucleic Acid Sequence
                                                    SEQ ID NO: 12
ATGTTGAGGTTAACTTCATTAAGCATTATTTTCTTTCTCTGTCTTGCTTTTATCAACCAT

CATGGTGCTGAAGCATGGAGCAAAGAGGGGCATATGATGACATGTCGCATCGCGCAGGGC

TTGTTGAATGATGAGGCAGCTCATGCAGTCAAGATGTTGTTGCCGGAATATGTTAACGGC

GACTTATCGGCCCTCTGTGTGTGGCCGGATCAAGTCCGGCACTGGTATAAGTATAAATGG

ACAAGCCCTCTACACTTCATTGATACACCAGATAAAGCTTGCAACTTTGATTATGAAAGG

GACTGTCATGATCAACATGGAGTGAAGGATATGTGTGTTGCTGGTGCAATTCAGAACTTT

ACTACTCAACTCTCTCATTACAGAGAGGGAACTTCTGATCGTCGATATAATATGACAGAG

GCCTTGCTGTTCTTGTCACATTTTATGGGAGATATCCATCAACCAATGCATGTTGGCTTT

ACAAGTGATGCTGGAGGAAATAGTATTGATTTACGCTGGTTTAGGCATAAATCGAACTTG

CACCATGTGTGGGATAGGGAGATAATTCTAACAGCTGCTAAAGACTACTATGCAAAGGAT

GTAAACCTCCTTGAAGAAGACATTGAAGGAAACTTCACTGACGGAATTTGGTCTGATGAT

CTTGCTTCTTGGAGAGAATGTGGCAATGTCTTTTCTTGTGTAAACAAGTTTGCAACGGAA

AGTATAAATATAGCATGCAAATGGGGATACAAAAGTGTTGAAGCTGGTGAAACTTTATCA

GATGATTATTTCAATTCAAGACTTCCAATAGTGATGAAACGAGTAGCACAAGGTGGAATA

CGATTAGCCATGCTTTTAAACAACGTTTTTGGAGTTTCTCAACAAGAAGATTCAGTTGCT

GCAACTTAA
```

-continued

Amino Acid Sequence
                                                    SEQ ID NO: 13
MLRLTSLSIIFFLCLAFINHHGAEAWSKEGHMMTCRIAQGLLNDEAAHAVKMLLPEYVNG

DLSALCVWPDQVRHWYKYKWTSPLHFIDTPDKACNFDYERDCHDQHGVKDMCVAGAIQNF

TTQLSHYREGTSDRRYNMTEALLFLSHFMGDIHQPMHVGFTSDAGGNSIDLRWFRHKSNL

HHVWDREIILTAAKDYYAKDVNLLEEDIEGNFTDGIWSDDLASWRECGNVFSCVNKFATE

SINIACKWGYKSVEAGETLSDDYFNSRLPIVMKRVAQGGIRLAMLLNNVFGVSQQEDSVA

AT

Exemplary Endonucleases - CEL I Mature Core Sequence
Amino Acid Sequence
                                                    SEQ ID NO: 14
WSKEGHSMTCKIAQDLLGPEAKHAVQMLLPENVNGDLSALSVWPDQVRHWYKYRWTSPLH

FIDTPDQACNFNYQRDCHDPHGVKGMCVAGAIQNFTNQLSHYRHGTSDRRYNMTEALLFL

AHFMGDIHQPLHVGFTSDEGGNTIDLRWFRHKSNLHHVWDREIILTAAADYYGKDIDLLQ

EDIKGNFTDGIWSGDLASWRECSDIFSCVNKYAAESINMACKWGYKDVKSGDTLSDDYFN

SRLPIVMKRIAQGGVRLAMILNRVFGDSKEDSLIAT

Exemplary Endonucleases - CEL II Variant - *Vitis vinifera*
Nucleic Acid Sequence
                                                    SEQ ID NO: 15
ATGTGGGGAAAGGAAGGACACTATGCAGTTTGTAAAATAGCTGAGGGGTTCCTTTCTGAA

GATGCATTAGGAGCAGTGAAAGGATTGCTTCCAGATTATGCTGATGGTGATCTGGCTGCC

GTTTGCTCCTGGGCTGATGAGATTCGTCACAACTTCCATTGGCGATGGAGTGGCCCTTTA

CATTATGTAGATACACCAGATTACAGGTGTAATTATGAATACTGCAGAGACTGCCATGAC

TTCAGAGGACACAAAGATATATGTGTAACTGGAGCAATTTACAACTACACAAAGCAACTC

ACTTCTGGTTATCACAATTCAGGTTCAGAAATAAGATACAATTTGACAGAGGCCCTCATG

TTCTTATCAGATTTTATTGGGGATGTCCATCAGCCCCTACATGTTGGTTTTACTGGAGAT

GAAGGTGGGAACACAATAATAGTCCGTTGGTACCGGAGGAAGACTAATTTGCATCATATA

TGGGATGACATGATCATTGATTCCGCCTTGAAGACATATTACAATTCAGATATTGCAATC

ATGATACAAGCCATTCAAAGAAATATTACAGGTGACTGGTCCTTTGATATCTCATCATGG

AAAAATTGTGCATCTGATGATACGGCTTGTCCAAACCTGTATGCGTCTGAAGGCATTAGT

TTAGCTTGCAAGTTTGCTTACAGAAATGCCACACCAGGAAGCACTCTAGGAGATGATTAC

TTCCTGTCTCGGCTACCAATTGTGGAGAAGAGGCTAGCCCCGAGTGGGATCCGCCTGGCT

GCCACCCTTAACCGTATCTTTGCTTCTCAAGGCAAGAGAGCTAAAGCATGA

Amino Acid Sequence
                                                    SEQ ID NO: 16
MWGKEGHYAVCKIAEGFLSEDALGAVKGLLPDYADGDLAAVCSWADEIRHNFHWRWSGPL

HYVDTPDYRCNYEYCRDCHDFRGHKDICVTGAIYNYTKQLTSGYHNSGSEIRYNLTEALM

FLSDFIGDVHQPLHVGFTGDEGGNTIIVRWYRRKTNLHHIWDDMIIDSALKTYYNSDIAI

MIQAIQRNITGDWSFDISSWKNCASDDTACPNLYASEGISLACKFAYRNATPGSTLGDDY

FLSRLPIVEKRLAPSGIRLAATLNRIFASQGKRAKA

Amino Acid Sequence for Insect Cell Expression
                                                    SEQ ID NO: 17
MKFLVNVALVFMVVYISYIYAWGKEGHYAVCKIAEGFLSEDALGAVKALLPDYAEGDLAA

VCSWADEIRHNFHWRWSGPLHYVDTPDYRCNYEYCRDCHDFRGHKDICVTGAIYNYTKQL

TSGYHNSGSEIRYNLTEALMFLSHFIGDVHQPLHVGFTGDEGGNTIIVRWYRRKTNLHHI

WDNMIIDSALKTYYNSDLAIMIQAIQRNITGDWSFDISSWKNCASDDTACPNLYASESIS

LACKFAYRNATPGSTLGDDYFLSRLPIVEKRLAQGGIRLAATLNRIFASQPKISLKHEDK

RVEKTTPVDYIEWSPLQQFSGSHHHHHHHHG
Underlined—honeybee melittin secretion signal; polyhistidine tag with linkers Exemplary Endonucleases - CEL II Variant - Chocolate Pots
Nucleic Acid Sequence

SEQ ID NO: 18

ATGACTTGGGGATTTTGGGCACATCGGCAAATACATCGCCAAGCCGTTTATCTTATGCCT

TCGCCCGTGGCAGAGTTCTTTCGCGCAAATGTTCAAGAACTTGTCGACCGCTCGGTTGAA

GCCGATGAACGCCGACGCATAGACCCCAACGAAGCTCCGCAACACTTCATTGATTTAGAC

CGCTACGGTGCCTATCCTTTTGAACAACTTCCGAGAGATTATGAAAAAGCCGTTGAGAAA

TTCGGCTATGAGCGGCTGAAAGAAAATGGACTTGTGCCGTGGCGCATTGCCGCCTTTGCC

GATAGCCTCACCAACGCATTTCGGGAGCAGAACCGCGAAAAAATTTTATACTTCGCCGCA

AATTTAGGGCATTATGTCGCCGATGCTAACGTGCCACTTCATGCCACCGAAAACTACGAC

GGACAACTCACAGGGCAAAAGGATTGCACGCACGTTGGGAAACTATTTATCCTCAAAAG

TTTATGCTCCCACGAGAAACCACCTATCTCGAAAACGGGAGCATCTTTATCATTGACAAC

ATCACCGAAGAAGCCTTCAACTGGTCATTAGAAAGTTATGTATTGAGCCAACAAGTTTTG

GCGATTGATAAGCAAATTCAATCGGAATTGTCAGAAGAAGAATTGTATGAGTTAAATTCA

TCAGACGCGCCGCCATTTCGTCGCGATTTTTCACAACGCTATTATGAAAAACTCAAAGAA

AAATTGAATCAAATGGTTGAAAAATGCTTTGAGTTAAGCGTCATTAGGGTAGCGTCAGTT

TGGTATTTTTCTTGGTTAAAAGCAGAAAAACCGAATTTATTTAACTTATTAAAAAATTGA

Amino Acid Sequence

SEQ ID NO: 19

MTWGFWAHRQIHRQAVYLMPSPVAEFFRANVQELVDRSVEADERRRIDPNEAPQHFIDLD

RYGAYPFEQLPRDYEKAVEKFGYERLKENGLVPWRIAAFADSLTNAFREQNREKILYFAA

NLGHYVADANVPLHATENYDGQLTGQKGLHARWETIYPQKFMLPRETTYLENGSIFIIDN

ITEEAFNWSLESYVLSQQVLAIDKQIQSELSEEELYELNSSDAPPFRRDFSQRYYEKLKE

KLNQMVEKCFELSVIRVASVWYFSWLKAEKPNLFNLLKN

Exemplary Endonucleases - CEL II Variant - Obsidian pool
Nucleic Acid Sequence

SEQ ID NO: 20

ATGTTTTGGGCACATCAAAAAGTCAACGAGCATGCCATTGATTTATACCCGAGCCACTC

CGCAGTTTTTATGAACAAAATAAGGAATACATAGTTAAGGAGTCGGTCGCCCCTGATCTC

AGGCGTGCAGAAAACAAGGAAGAAGGTTATTATCACTATATGGATCTCGATAAATATGGT

GAATATCCGTTCAAGAATTTGCCAGAAAACTACGACGACGCAGTAAAAAGGTTTGGTTAC

GATACTGTTCTCAAGAACGGAATTGTGCCGTGGAAGGTAAAATGGTTGACAGACAGTTTG

AGTCAAGCTATGGAGAGAAAGGATGTGCCACAGGTCTTAAGACTTTCAGCCGACCTTGGT

CATTATGTTGCTGACATGCATGTTCCATTTCATTCGACAGAAAATTATGATGGACAGCTG

ACAGGCAACATAGGAATACACTTCAGATGGGAAAGCGGCATTCCAGAACATTTTGGAACA

AATTACAACTATGAGGGAATAGAGCCCGCTGTTTACTTCAAGCATCCTGATAAAAAGGCA

TTTGAGATACTGACTATGAGTTACAAGTTGATTCTACCTTCTCTCAAGGCTGATAGTCTT

GCAAAAGTTGGATTGAATGGAAAGAGACTTTATAAAGTTGAGAGAGAAGACGGTAAAAAA

GTTTACGTTTATTCAAACGAGTATTATGAGAAGTTCAACAAAAACCTTGGTGGTATTGTA

-continued

GAATCGCAGATGAGGCTGGCAATCCATGATGTTGCAAGCTACTGGTATACTGCATGGGTA

AATGCCGGTAAACCAAAGTTTTGGTAA

Amino Acid Sequence
SEQ ID NO: 21
MFWAHQKVNEHAIDLLPEPLRSFYEQNKEYIVKESVAPDLRRAENKEEGYYHYMDLDKYG

EYPFKNLPENYDDAVKRFGYDTVLKNGIVPWKVKWLTDSLSQAMERKDVPQVLRLSADLG

HYVADMHVPFHSTENYDGQLTGNIGIHFRWESGIPEHFGTNYNYEGIEPAVYFKHPDKKA

FEILTMSYKLILPSLKADSLAKVGLNGKRLYKVEREDGKKVYVYSNEYYEKFNKNLGGIV

ESQMRLAIHDVASYWYTAWVNAGKPKFW

Exemplary Endonucleases - CEL II Variant - *Vitis vinifera*
Nucleic Acid Sequence
SEQ ID NO: 22
ATGGCTTGGTCTGGGGTCTTGTTGATTGTGAGGGCACTTGTTCTTCTGCAATTGATTCCT

GGAATTCTGAGTTGGGGAAAGGAAGGACACTATGCAGTTTGTAAAATAGCTGAGGGGTTC

CTTTCTGAAGATGCATTAGGAGCAGTGAAAGCATTGCTTCCAGATTATGCTGAAGGTGAT

CTGGCTGCGGTTTGCTCCTGGGCTGATGAGATTCGTCACAACTTCCATTGGCGATGGAGT

GGCCCTTTACATTATGTAGATACGCCAGATTACAGGTGTAACTATGAATACTGCAGAGAC

TGCCATGACTTCAGAGGACACAAAGATATATGTGTAACTGGAGCAATTTACAATTACACA

AAGCAACTCACTTCTGGTTATCACAATTCAGGTTCAGAAATAAGATACAATTTGACAGAG

GCACTCATGTTCTTATCACATTTTATTGGGGATGTCCATCAGCCCCTACATGTTGGTTTT

ACTGGAGATGAAGGTGGGAACACAATAATAGTCCGTTGGTACCGGAGGAAGACTAATTTG

CATCATATATGGGATAACATGATCATTGATTCCGCCCTGAAGACATATTACAATTCAGAT

CTTGCAATCATGATACAAGCCATTCAAAGAAATATTACGGGTGATTGGTCCTTTGATATC

TCATCATGGAAAAATTGTGCATCTGATGATACGGCTTGTCCAAACCTGTATGCTTCTGAA

AGCATTAGTTTAGCTTGCAAGTTTGCTTACAGAAATGCCACACCAGGAAGCACTCTAGGA

GATGATTACTTCCTGTCTCGGCTACCAATTGTGGAGAAGAGGCTAGCCCAAGGTGGGATC

CGCCTGGCTGCCACCCTTAACCGTATCTTTGCTTCTCAACCAAAAATCTCTCTCAAGCAT

GAAGATAAAAGGGTAGAGAAAACAACTCCAGTGGATTATATAGAGTGGAGCCCACTGCAA

CAATTTTCATAA

Amino Acid Sequence
SEQ ID NO: 23
MAWSGVLLIVRALVLLQLIPGILSWGKEGHYAVCKIAEGFLSEDALGAVKALLPDYAEGD

LAAVCSWADEIRHNFHWRWSGPLHYVDTPDYRCNYEYCRDCHDFRGHKDICVTGAIYNYT

KQLTSGYHNSGSEIRYNLTEALMFLSHFIGDVHQPLHVGFTGDEGGNTIIVRWYRRKTNL

HHIWDNMIIDSALKTYYNSDLAIMIQAIQRNITGDWSFDISSWKNCASDDTACPNLYASE

SISLACKFAYRNATPGSTLGDDYFLSRLPIVEKRLAQGGIRLAATLNRIFASQPKISLKH

EDKRVEKTTPVDYIEWSPLQQFS

Exemplary Endonucleases - CEL II Variant - *Solanum*
Nucleic Acid Sequence
SEQ ID NO: 24
ATGGGTGGGTTTGAGCTCAAATGGTTTGTAGGAGTAGCTGTTGTTCTGATGATGGTTCAA

AATATTCTTGGTTGGGGGAAAGAGGGACACTATATTATCTGCAAAATTGCTGAGGAATAT

CTAACAGAAGATGCTTTAGCTGCAGTCAAAGCATTACTCCCAGATCAAGCCGAAGGTGAT

CTTGCAGCTGTCTGCTCCTGGCCTGATGAGGTTCGGCGCCACTACCACTACCGCTGGAGC

TCTCCATTACATTATGTAGATACACCTGATTTCTTGTGCAATTACAAATATTGCCGAGAC

TGCCATGACGGGCATGGGCTCAAGGACAGGTGTGTTACGGGAGCAATATACAACTACTCA

```
ATGCAACTTTCGCAGGGATATTATGATTTGAATTCAGAAAAATACAACTTGACTGAAGCA

CTTATGTTCTTGTCTCATTTTGTTGGTGACGTACATCAGCCTCTCCATGTTGGTTTCACT

GGAGATCTTGGTGGAAACAGTATAATTGTTCGTTGGTACAGGAGGAAGACTAATTTGCAC

CATGTATGGGATAACATGATTATTGAATCTGCGTTGAAGACATACTACAAATCTGATATA

ATGTTAATGACACAAGTTCTTCTGAAAAACATCACTCATGAATGGTCCGATGATGTTCCA

TCTTGGGAAGATTGCAAGGAGATGGTTTGTCCTGACCCATATGCTTCTGAAAGTATCCGT

TTGGCCTGCAAATTTGCCTACAGAAATGCAACCCCGGGAAGCACTTTAACAGACGATTAC

TTCCTCTCTCGTCTTCCTGTTGTGGAGAAGAGGTTGGCACAAGGTGGGGTCCGCTTGGCC

GAAGTTCTCAACAGAATTTTCACTAAAAAACCATCAGATGCTGCACAATGA
```

Amino Acid Sequence
                                            SEQ ID NO: 25
```
MGGFELKWFVGVAVVLMMVQNILGWGKEGHYIICKIAEEYLTEDALAAVKALLPDQAEGD

LAAVCSWPDEVRRHYHYRWSSPLHYVDTPDFLCNYKYCRDCHDGHGLKDRCVTGAIYNYS

MQLSQGYYDLNSEKYNLTEALMFLSHFVGDVHQPLHVGFTGDLGGNSIIVRWYRRKTNLH

HVWDNMIIESALKTYYKSDIMLMTQVLLKNITHEWSDDVPSWEDCKEMVCPDPYASESIR

LACKFAYRNATPGSTLTDDYFLSRLPVVEKRLAQGGVRLAEVLNRIFTKKPSDAAQ
```

Exemplary Endonucleases - CEL II Variant - *Medicago*
Nucleic Acid Sequence
                                            SEQ ID NO: 26
```
ATGATCACGCTCTTAGTTCCGTTGCTGCTATCACTCGCGTTGCCAAATGTTCTGGCTTGG

GGAAAAGATGGTCACTATGCAATTTGTAAAATTTCACAGGAGTATCTTAGTGAAGATGCT

CTATTTGCAGTCAAACAATTACTTCCAGATTCTGCTCAAGCTGATCTTGCTTCAGTTTGC

TCTTGGCCTGATGAGATTCGCCATAATTACCATTATCGTTGGAGTAGTCCTTTACATTAT

ATTGATACACCAGATTTCAAATGTAACTATCAATATTGCAGAGACTGTCATGATTCTTAT

GGACATAAGCATAGATGCGTTACTGGAGCAATATACAATTATACAATGCAATTAAAATTA

GCTAACGCCGATGCTTCATCTGAATTAAAATATAACTTGACAGAGGCACTTATGTTCTTG

TCACATTTTGTTGGAGATGTTCATCAGCCCCTACATGTTGGTTTTACTGGAGACCTAGGT

GGAAACTCAATAACAGTTCGTTGGTACAGGAGGAAAACAAATCTTCATCACGTATGGGAT

AACATGATTATTGAGTCTGCTCTGAAAAAGTTCTATGGTTCAGATCTTTCAACTATGATA

CAGGCTATTCAAAGGAATATTAGTGATATTTGGTCAAATGATGTATCTATTTGGGAACAT

TGTGCACACAACCACACAGCATGTCCAGACCGGTATGCTTCTGAGAGTATTAGCTTGGCA

TGCAAGTTTGCGTATAAGAATGCTACACCGGGAAGCACTTTGGAAGATGACTACTTCCTT

TCTCGGTTGCCTATTGTGGAGAAAAGGCTGGCTCAAGGTGGTGTGCGACTTGCAGCTATC

CTCAACCACATTTTCACTCCGAAGACCAGAATAGCTCAAGCTTAA
```

Amino Acid Sequence
                                            SEQ ID NO: 27
```
MITLLVPLLLSLALPNVLAWGKDGHYAICKISQEYLSEDALFAVKQLLPDSAQADLASVC

SWPDEIRHNYHYRWSSPLHYIDTPDFKCNYQYCRDCHDSYGHKHRCVTGAIYNYTMQLKL

ANADASSELKYNLTEALMFLSHFVGDVHQPLHVGFTGDLGGNSITVRWYRRKTNLHHVWD

NMIIESALKKFYGSDLSTMIQAIQRNISDIWSNDVSIWEHCAHNHTACPDRYASESISLA

CKFAYKNATPGSTLEDDYFLSRLPIVEKRLAQGGVRLAAILNHIFTPKTRIAQA
```

-continued

Exemplary Endonucleases - CEL II Variant Mature Core Sequence
Amino Acid Sequence
SEQ ID NO: 28
WGKEGHYAVCKIAEGFLSEDALGAVKGLLPDYADGDLAAVCSWADEIRHNFHWRWSGPLH

YVDTPDYRCNYEYCRDCHDFRGHKDICVTGAIYNYTKQLTSGYHNSGSEIRYNLTEALMF

LSDFIGDVHQPLHVGFTGDEGGNTIIVRWYRRKTNLHHIWDDMIIDSALKTYYNSDIAIM

IQAIQRNITGDWSFDISSWKNCASDDTACPNLYASEGISLACKFAYRNATPGSTLGDDYF

LSRLPIVEKRLAPSGIRLAATLNRIFASQGK

Exemplary Endonucleases - CEL II Variant Mature Core Sequence
Amino Acid Sequence
SEQ ID NO: 29
WGKEGHYAVCKIAEGFLSEDALGAVKALLPDYAEGDLAAVCSWADEIRHNFHWRWSGPLH

YVDTPDYRCNYEYCRDCHDFRGHKDICVTGAIYNYTKQLTSGYHNSGSEIRYNLTEALMF

LSHFIGDVHQPLHVGFTGDEGGNTIIVRWYRRKTNLHHIWDNMIIDSALKTYYNSDLAIM

IQAIQRNITGDWSFDISSWKNCASDDTACPNLYASESISLACKFAYRNATPGSTLGDDYF

LSRLPIVEKRLAQGGIRLAATLNRIFASQPK

Codon-Optimized Mature Core Region of *Mimulus guttatus* CEL I
Nucleic Acid Sequence
SEQ ID NO: 30
TGGAGTAAGGAGGGACATAGCATGACATGTAAGATAGCCCAGGACTTGTTGGGTCCCGAA

GCCAAACACGCCGTGCAAATGTTGTTGCCTGAAAATGTGAACGGCGACCTAAGCGCCTTG

TCGGTGTGGCCGGACCAAGTGAGACACTGGTACAAATACAGATGGACCTCCCCTTTGCAC

TTCATTGACACCCCCGATCAGGCTTGCAACTTTAACTACCAGAGAGACTGCCATGACCCG

CACGGTGTAAAAGGCATGTGCGTTGCCGGTGCCATTCAAAATTTCACGAACCAATTGTCG

CACTACAGACACGGCACGTCGGACAGACGTTACAACATGACGGAGGCCTTGTTGTTTTTG

GCCCACTTTATGGGCGATATTCATCAGCCGTTGCACGTGGGCTTCACGTCAGACGAAGGC

GGCAACACGATTGACTTGAGATGGTTTCGCCACAAGAGCAACTTGCATCACGTATGGGAT

CGAGAAATTATCCTAACTGCCGCTGCGGACTACTACGGAAAGGACATCGACCTACTCCAG

GAGGATATCAAAGGCAATTTTACTGACGGCATCTGGTCGGGCGATTTGGCCTCGTGGAGA

GAATGTTCGGACATTTTTTCGTGTGTGAACAAGTACGCTGCCGAATCCATAAACATGGCT

TGTAAATGGGGCTACAAGGATGTGAAATCGGGTGACACGCTCTCGGACGACTATTTCAAC

AGTCGTCTCCCGATCGTAATGAAAAGAATCGCTCAAGGAGGCGTTCGCTTAGCAATGATT

CTCAACAGAGTATTCGGTGATAGCAAAGAGGACAGCTTGATTGCCACG

Codon-Optimized Expression Cassette for
Insect Cell Expression of *Mimulus guttatus* CEL I
Nucleic Acid Sequence
SEQ ID NO: 31
ACCATGAAGTTCTTGGTCAACGTAGCACTGGTTTTTATGGTAGTCTATATCAGCTACATT

TACGCGTGGAGTAAGGAGGGACATAGCATGACATGTAAGATAGCCCAGGACTTGTTGGGT

CCCGAAGCCAAACACGCCGTGCAAATGTTGTTGCCTGAAAATGTGAACGGCGACCTAAGC

GCCTTGTCGGTGTGGCCGGACCAAGTGAGACACTGGTACAAATACAGATGGACCTCCCCT

TTGCACTTCATTGACACCCCCGATCAGGCTTGCAACTTTAACTACCAGAGAGACTGCCAT

GACCCGCACGGTGTAAAAGGCATGTGCGTTGCCGGTGCCATTCAAAATTTCACGAACCAA

TTGTCGCACTACAGACACGGCACGTCGGACAGACGTTACAACATGACGGAGGCCTTGTTG

TTTTTGGCCCACTTTATGGGCGATATTCATCAGCCGTTGCACGTGGGCTTCACGTCAGAC

GAAGGCGGCAACACGATTGACTTGAGATGGTTTCGCCACAAGAGCAACTTGCATCACGTA

TGGGATCGAGAAATTATCCTAACTGCCGCTGCGGACTACTACGGAAAGGACATCGACCTA

-continued

CTCCAGGAGGATATCAAAGGCAATTTTACTGACGGCATCTGGTCGGGCGATTTGGCCTCG

TGGAGAGAATGTTCGGACATTTTTTCGTGTGTGAACAAGTACGCTGCCGAATCCATAAAC

ATGGCTTGTAAATGGGGCTACAAGGATGTGAAATCGGGTGACACGCTCTCGGACGACTAT

TTCAACAGTCGTCTCCCGATCGTAATGAAAAGAATCGCTCAAGGAGGCGTTCGCTTAGCA

ATGATTCTCAACAGAGTATTCGGTGATAGCAAAGAGGACAGCTTGATTGCCACGGGCTCG

CACCATCACCACCATCACCACCACGGTTGATAA

Codon-Optimized Mature Core Region of Vitis vinifera CEL II
Nucleic Acid Sequence
SEQ ID NO: 32

TGGGGCAAAGAAGGCCACTACGCCGTGTGTAAGATTGCGGAGGGCTTTTTGTCGGAAGAC

GCATTGGGAGCGGTCAAAGCCTTGTTGCCGGACTACGCGAAGGCGACTTGGCAGCCGTA

TGTAGCTGGGCCGACGAGATCAGACACAACTTTCACTGGAGATGGTCGGGCCCACTGCAT

TACGTCGACACGCCGGATTACAGATGCAACTACGAGTACTGCCGCGACTGTCACGACTTC

AGAGGCCACAAAGACATTTGCGTCACGGGCGCGATATACAACTACACGAAACAATTGACG

TCGGGCTACCACAACAGTGGCTCCGAGATTCGATACAACCTCACGGAGGCCTTGATGTTC

CTCTCGCATTTCATTGGCGACGTGCACCAACCGCTGCATGTGGGCTTTACGGGCGATGAA

GGCGGAAATACGATCATTGTCCGTTGGTACCGCAGAAAGACCAACCTCCACCACATATGG

GACAACATGATCATCGACTCGGCGTTGAAGACCTACTACAACAGCGACCTGGCCATAATG

ATCCAGGCGATTCAAAGAAACATCACCGGCGATTGGTCCTTTGACATCAGCAGCTGGAAG

AACTGTGCCAGTGACGACACTGCTTGTCCGAACCTATACGCGTCGGAGAGCATCTCGTTG

GCCTGTAAATTTGCCTACAGAAATGCCACCCCCGGTTCGACGCTGGGCGACGACTACTTC

TTGTCGCGATTGCCGATTGTTGAAAAACGCCTCGCCCAAGGCGGTATTAGATTGGCCGCC

ACCTTGAACCGTATTTTTGCCTCGCAACCGAAAATCTCGCTGAAACACGAAGACAAGAGA

GTCGAGAAGACGACGCCGGTAGACTACATCGAGTGGTCGCCATTGCAACAGTTCAGC

Codon-Optimized Expression Cassette for
Insect Cell Expression of Mimulus guttatus CEL I
Nucleic Acid Sequence
SEQ ID NO: 33

ACCATGAAGTTCTTGGTGAACGTGGCGCTGGTGTTCATGGTCGTGTACATCTCCTACATT

TACGCGTGGGGCAAAGAAGGCCACTACGCCGTGTGTAAGATTGCGGAGGGCTTTTTGTCG

GAAGACGCATTGGGAGCGGTCAAAGCCTTGTTGCCGGACTACGCGGAAGGCGACTTGGCA

GCCGTATGTAGCTGGGCCGACGAGATCAGACACAACTTTCACTGGAGATGGTCGGGCCCA

CTGCATTACGTCGACACGCCGGATTACAGATGCAACTACGAGTACTGCCGCGACTGTCAC

GACTTCAGAGGCCACAAAGACATTTGCGTCACGGGCGCGATATACAACTACACGAAACAA

TTGACGTCGGGCTACCACAACAGTGGCTCCGAGATTCGATACAACCTCACGGAGGCCTTG

ATGTTCCTCTCGCATTTCATTGGCGACGTGCACCAACCGCTGCATGTGGGCTTTACGGGC

GATGAAGGCGGAAATACGATCATTGTCCGTTGGTACCGCAGAAAGACCAACCTCCACCAC

ATATGGGACAACATGATCATCGACTCGGCGTTGAAGACCTACTACAACAGCGACCTGGCC

ATAATGATCCAGGCGATTCAAAGAAACATCACCGGCGATTGGTCCTTTGACATCAGCAGC

TGGAAGAACTGTGCCAGTGACGACACTGCTTGTCCGAACCTATACGCGTCGGAGAGCATC

TCGTTGGCCTGTAAATTTGCCTACAGAAATGCCACCCCCGGTTCGACGCTGGGCGACGAC

TACTTCTTGTCGCGATTGCCGATTGTTGAAAAACGCCTCGCCCAAGGCGGTATTAGATTG

-continued

GCCGCCACCTTGAACCGTATTTTTGCCTCGCAACCGAAAATCTCGCTGAAACACGAAGAC

AAGAGAGTCGAGAAGACGACGCCGGTAGACTACATCGAGTGGTCGCCATTGCAACAGTTC

AGCGGAAGCCACCACCATCACCACCATCATCACGGCTGATAA

---

What is claimed is:

1. A composition comprising: (i) a molecule having a unidirectional mismatch endonuclease activity having at least 80% sequence identity to a sequence selected from the group consisting of: SEQ ID NO: 10, SEQ ID NO: 11, SEQ ID NO: 13, SEQ ID NO: 14, SEQ ID NO: 16, SEQ ID NO: 17, SEQ ID NO: 19, SEQ ID NO: 21, SEQ ID NO: 23, SEQ ID NO: 25, SEQ ID NO: 27, SEQ ID NO: 28, and SEQ ID NO: 29, and (ii) a molecule having unidirectional exonuclease activity of the same directionality as the unidirectional mismatch endonuclease activity of (i).

2. A composition according to claim 1, wherein the molecule of (ii) is selected from the group consisting of exonuclease III, a DNA polymerase, and a combination of exonuclease III and a DNA polymerase.

3. A composition according to claim 2, wherein the molecule of (ii) is selected from the group consisting of exonuclease III.

4. The composition of claim 1, wherein the molecule having a unidirectional mismatch endonuclease activity has at least 90% sequence identity to a sequence selected from the group consisting of: SEQ ID NO: 10, SEQ ID NO: 11, SEQ ID NO: 13, SEQ ID NO: 14, SEQ ID NO: 16, SEQ ID NO: 17, SEQ ID NO: 19, SEQ ID NO: 21, SEQ ID NO: 23, SEQ ID NO: 25, SEQ ID NO: 27, SEQ ID NO: 28, and SEQ ID NO: 29.

5. The composition according to claim 4, wherein the molecule of (ii) is selected from the group consisting of exonuclease III, a DNA polymerase, and a combination of exonuclease III and a DNA polymerase.

6. The composition according to claim 4 wherein the molecule of (ii) is exonuclease III.

7. A kit comprising a composition according to claim 1.
8. A kit comprising a composition according to claim 2.
9. A kit comprising a composition according to claim 3.
10. A kit comprising a composition according to claim 4.
11. A kit comprising a composition according to claim 5.
12. A kit comprising a composition according to claim 6.

* * * * *

SEQUENCE LISTING

<160> NUMBER OF SEQ ID NOS: 33

<210> SEQ ID NO 1
<211> LENGTH: 888
<212> TYPE: DNA
<213> ORGANISM: Selaginella lepidophylla

<400> SEQUENCE: 1

| | | | | | |
|---|---|---|---|---|---|
| atggcaacga | ccaagacgag | cgggatggcg | ctggctttgc | tcctcgtcgc | cgccctggcc | 60 |
| gtgggagctg | cggcctgggg | gaaagagggc | catcgcctca | cttgtatggt | cgccgagccc | 120 |
| tttctaagct | ctgaatccaa | gcaagctgtg | gaggagcttc | tctctggaag | agatctcccg | 180 |
| gacttgtgtt | catgggccga | tcagattcga | agatcgtata | agtttagatg | gactggtcct | 240 |
| ttgcactaca | tcgatactcc | agacaacctc | tgcacctatg | actatgatcg | tgactgccac | 300 |
| gattcccatg | gaagaagga | cgtgtgtgtc | gctggtggga | tcaacaatta | ctcgtcgcag | 360 |
| ctggaaacgt | tctagattc | agagagctcg | tcgtataact | tgaccgaggc | gctgctcttc | 420 |
| ctggctcact | ttgtcgggga | tatacaccag | cccttgcacg | tagcatttac | gagtgatgcc | 480 |
| ggaggcaatg | gcgtgcacgt | ccgctggttt | ggacgaaagg | ccaacttgca | tcacgtctgg | 540 |
| gatacagaat | ttatttctag | agccaatcgt | gtgtactacc | acgacatttc | caagatgctc | 600 |
| cggaacatta | ccaggagcat | aactaagaag | aatttcaata | gttggagcag | atgtaagact | 660 |
| gatccggcgg | cttgtattga | tagttatgcg | acagaaagta | tagatgcttc | ttgcaactgg | 720 |
| gcatacaaag | acgcacccga | cggaagctct | ctagatgatg | attacttctc | ttcacgcctt | 780 |
| ccaattgttg | agcagcgtct | tgctcaaggg | ggcgtcaggc | tggcgtcaat | actcaacagg | 840 |
| attttggag | gagcaaagtc | gaacaggtcc | agtcgctcaa | gcatgtag | | 888 |

<210> SEQ ID NO 2
<211> LENGTH: 295
<212> TYPE: PRT
<213> ORGANISM: Selaginella lepidophylla

<400> SEQUENCE: 2

Met Ala Thr Thr Lys Thr Ser Gly Met Ala Leu Ala Leu Leu Leu Val
1               5                   10                  15

Ala Ala Leu Ala Val Gly Ala Ala Trp Gly Lys Glu Gly His Arg
            20                  25                  30

Leu Thr Cys Met Val Ala Glu Pro Phe Leu Ser Ser Glu Ser Lys Gln
        35                  40                  45

Ala Val Glu Glu Leu Leu Ser Gly Arg Asp Leu Pro Asp Leu Cys Ser
    50                  55                  60

Trp Ala Asp Gln Ile Arg Arg Ser Tyr Lys Phe Arg Trp Thr Gly Pro
65                  70                  75                  80

Leu His Tyr Ile Asp Thr Pro Asp Asn Leu Cys Thr Tyr Asp Tyr Asp
                85                  90                  95

Arg Asp Cys His Asp Ser His Gly Lys Lys Asp Val Cys Val Ala Gly
            100                 105                 110

Gly Ile Asn Asn Tyr Ser Ser Gln Leu Glu Thr Phe Leu Asp Ser Glu

```
                    115                 120                 125
Ser Ser Ser Tyr Asn Leu Thr Glu Ala Leu Leu Phe Leu Ala His Phe
    130                 135                 140

Val Gly Asp Ile His Gln Pro Leu His Val Ala Phe Thr Ser Asp Ala
145                 150                 155                 160

Gly Gly Asn Gly Val His Val Arg Trp Phe Gly Arg Lys Ala Asn Leu
                165                 170                 175

His His Val Trp Asp Thr Glu Phe Ile Ser Arg Ala Asn Arg Val Tyr
            180                 185                 190

Tyr His Asp Ile Ser Lys Met Leu Arg Asn Ile Thr Arg Ser Ile Thr
        195                 200                 205

Lys Lys Asn Phe Asn Ser Trp Ser Arg Cys Lys Thr Asp Pro Ala Ala
    210                 215                 220

Cys Ile Asp Ser Tyr Ala Thr Glu Ser Ile Asp Ala Ser Cys Asn Trp
225                 230                 235                 240

Ala Tyr Lys Asp Ala Pro Asp Gly Ser Ser Leu Asp Asp Tyr Phe
                245                 250                 255

Ser Ser Arg Leu Pro Ile Val Glu Gln Arg Leu Ala Gln Gly Gly Val
        260                 265                 270

Arg Leu Ala Ser Ile Leu Asn Arg Ile Phe Gly Gly Ala Lys Ser Asn
    275                 280                 285

Arg Ser Ser Arg Ser Ser Met
    290                 295

<210> SEQ ID NO 3
<211> LENGTH: 1135
<212> TYPE: DNA
<213> ORGANISM: Apium sp.

<400> SEQUENCE: 3
tactcactat agggctcgag cgcccgcccg ggcaggtata atattagact tgtactcaat      60
gacaagcgcc atctatgagt ttcatcatgc ctatatataa acacatgaac ctgtcattgt     120
tcatttatgc attattgttg tattagctga aaaatttctg gcaaatgacg cgattatatt     180
ctgtgttctt tcttttgttg gctcttgtag ttgaaccggg tgttagagcc tggagcaaag     240
aaggccatgt catgacatgt caaattgcgc aggatctgtt ggagccagaa gcagcacatg     300
ctgtaaagat gctgttaccg gactatgcta atggcaactt atcgtcgctg tgtgtgtggc     360
ctgatcaaat tcgacactgg tacaagtaca ggtggactag ctctctccat ttcatcgata     420
cacctgatca agcctgttca tttgattacc agagagactg tcatgatcca catggaggga     480
aggacatgtg tgttgctgga gccattcaaa atttcacatc tcagcttgga catttccgcc     540
atggaacatc tgatcgtcga tataatatga cagaggcttt gttattttta tcccacttca     600
tgggagatat tcatcagcct atgcatgttg gatttacaag tgatatggga ggaaacagta     660
tagatttgcg ctggtttcgc cacaaatcca acctgcacca tgtttgggat agagagatta     720
ttcttacagc tgcagcagat taccatggta aggatatgca ctctctccta caagacatac     780
agaggaactt tacagagggt agttggttgc aagatgttga atcctggaag gaatgtgatg     840
atatctctac ttgcgccaat aagtatgcta aggagagtat aaaactagcc tgtaactggg     900
gttacaaaga tgttgaatct ggcgaaactc tgtcagataa atacttcaac acaagaatgc     960
caattgtcat gaaacggata gctcagggtg gaatccgttt atccatgatt ttgaaccgag    1020
ttcttggaag ctccgcagat cattctttgg catgaattta gatactgata ttcgcatttc    1080
```
tcatgacacc cttctcttat gcaatttgca gatcagctgt gattcactaa ttgaa        1135

<210> SEQ ID NO 4
<211> LENGTH: 296
<212> TYPE: PRT
<213> ORGANISM: Apium sp.

<400> SEQUENCE: 4

Met Thr Arg Leu Tyr Ser Val Phe Phe Leu Leu Leu Ala Leu Val Val
1               5                   10                  15

Glu Pro Gly Val Arg Ala Trp Ser Lys Glu Gly His Val Met Thr Cys
            20                  25                  30

Gln Ile Ala Gln Asp Leu Leu Glu Pro Glu Ala Ala His Ala Val Lys
        35                  40                  45

Met Leu Leu Pro Asp Tyr Ala Asn Gly Asn Leu Ser Ser Leu Cys Val
    50                  55                  60

Trp Pro Asp Gln Ile Arg His Trp Tyr Lys Tyr Arg Trp Thr Ser Ser
65                  70                  75                  80

Leu His Phe Ile Asp Thr Pro Asp Gln Ala Cys Ser Phe Asp Tyr Gln
                85                  90                  95

Arg Asp Cys His Asp Pro His Gly Gly Lys Asp Met Cys Val Ala Gly
            100                 105                 110

Ala Ile Gln Asn Phe Thr Ser Gln Leu Gly His Phe Arg His Gly Thr
        115                 120                 125

Ser Asp Arg Arg Tyr Asn Met Thr Glu Ala Leu Leu Phe Leu Ser His
    130                 135                 140

Phe Met Gly Asp Ile His Gln Pro Met His Val Gly Phe Thr Ser Asp
145                 150                 155                 160

Met Gly Gly Asn Ser Ile Asp Leu Arg Trp Phe Arg His Lys Ser Asn
                165                 170                 175

Leu His His Val Trp Asp Arg Glu Ile Ile Leu Thr Ala Ala Ala Asp
            180                 185                 190

Tyr His Gly Lys Asp Met His Ser Leu Leu Gln Asp Ile Gln Arg Asn
        195                 200                 205

Phe Thr Glu Gly Ser Trp Leu Gln Asp Val Glu Ser Trp Lys Glu Cys
    210                 215                 220

Asp Asp Ile Ser Thr Cys Ala Asn Lys Tyr Ala Lys Glu Ser Ile Lys
225                 230                 235                 240

Leu Ala Cys Asn Trp Gly Tyr Lys Asp Val Glu Ser Gly Glu Thr Leu
                245                 250                 255

Ser Asp Lys Tyr Phe Asn Thr Arg Met Pro Ile Val Met Lys Arg Ile
            260                 265                 270

Ala Gln Gly Gly Ile Arg Leu Ser Met Ile Leu Asn Arg Val Leu Gly
        275                 280                 285

Ser Ser Ala Asp His Ser Leu Ala
    290                 295

<210> SEQ ID NO 5
<211> LENGTH: 933
<212> TYPE: DNA
<213> ORGANISM: Apium sp.

<400> SEQUENCE: 5
atgggtatgt tgacttatac tggaatttat tttctgctat tacttccaag tgttttctgt        60
tggggaaaac aaggacattt tgcaatttgt aaaattgccc aggggttcct tagtaaagat       120

```
gcactgactg cagtgaaagc attgctccca gaatatgcag atggtgatct agcagctgtt    180
tgctcctggg ctgacgaggt tcgatttcat atgcgttgga gtagcccatt acattatgtg    240
gacacgcctg atttcaggtg taactataaa tactgtagag attgccatga ttctgttgga    300
cggaaagacc ggtgtgttac tggagcaatt cacaactaca cagagcaact tctattgggt    360
gttcatgact tgaattcaaa atgaataaca aacttgacgg aggcacttat gttcttatca    420
catttcgttg gtgatgtcca tcagcctcta catgttggct tccttggcga tgaaggagga    480
aacacaatca ccgtccgctg gtatcggagg aaaaccaatt gcatcatgt  atgggacaca    540 atgatgatta atcctccttt gaagacattc tacaattcag atctttctag cttaatacaa    600
gctattcaga gcaatattac aggtgtctgg cttaccgaca gcttatcttg gagcaattgc    660
actgctgatc atgtggtttg tccagacccg tatgcttctg aaagcattga gttggcctgc    720
aagtttgcct acagaaatgc cacacctggg accactttag gagatgagta cttcctctct    780
cggttgcctg ttgcggagaa gaggttggct caggctgggg tccgtttggc tgctactctt    840
aaccgaatct tcacttcaaa ccccagcgat ctcacaagat tgaatatgca aatggtgga    900 catagaagca gtaacaatat tgaaatagtg taa                                 933
```

<210> SEQ ID NO 6
<211> LENGTH: 310
<212> TYPE: PRT
<213> ORGANISM: Apium sp.

<400> SEQUENCE: 6

```
Met Gly Met Leu Thr Tyr Thr Gly Ile Tyr Phe Leu Leu Leu Leu Pro
1               5                   10                  15

Ser Val Phe Cys Trp Gly Lys Gln Gly His Phe Ala Ile Cys Lys Ile
            20                  25                  30

Ala Gln Gly Phe Leu Ser Lys Asp Ala Leu Thr Ala Val Lys Ala Leu
        35                  40                  45

Leu Pro Glu Tyr Ala Asp Gly Asp Leu Ala Ala Val Cys Ser Trp Ala
    50                  55                  60

Asp Glu Val Arg Phe His Met Arg Trp Ser Ser Pro Leu His Tyr Val
65                  70                  75                  80

Asp Thr Pro Asp Phe Arg Cys Asn Tyr Lys Tyr Cys Arg Asp Cys His
                85                  90                  95

Asp Ser Val Gly Arg Lys Asp Arg Cys Val Thr Gly Ala Ile His Asn
            100                 105                 110

Tyr Thr Glu Gln Leu Leu Leu Gly Val His Asp Leu Asn Ser Lys Met
        115                 120                 125

Asn Asn Asn Leu Thr Glu Ala Leu Met Phe Leu Ser His Phe Val Gly
    130                 135                 140

Asp Val His Gln Pro Leu His Val Gly Phe Leu Gly Asp Glu Gly Gly
145                 150                 155                 160

Asn Thr Ile Thr Val Arg Trp Tyr Arg Arg Lys Thr Asn Leu His His
                165                 170                 175

Val Trp Asp Thr Met Met Ile Glu Ser Ser Leu Lys Thr Phe Tyr Asn
            180                 185                 190

Ser Asp Leu Ser Ser Leu Ile Gln Ala Ile Gln Ser Asn Ile Thr Gly
        195                 200                 205

Val Trp Leu Thr Asp Ser Leu Ser Trp Ser Asn Cys Thr Ala Asp His
    210                 215                 220

Val Val Cys Pro Asp Pro Tyr Ala Ser Glu Ser Ile Glu Leu Ala Cys
```

```
                225                 230                 235                 240
Lys Phe Ala Tyr Arg Asn Ala Thr Pro Gly Thr Thr Leu Gly Asp Glu
                    245                 250                 255

Tyr Phe Leu Ser Arg Leu Pro Val Ala Glu Lys Arg Leu Ala Gln Ala
                260                 265                 270

Gly Val Arg Leu Ala Ala Thr Leu Asn Arg Ile Phe Thr Ser Asn Pro
                275                 280                 285

Ser Asp Leu Thr Arg Leu Asn Met His Asn Gly His Arg Ser Ser
                290                 295                 300

Asn Asn Ile Glu Ile Val
305                 310

<210> SEQ ID NO 7
<211> LENGTH: 873
<212> TYPE: DNA
<213> ORGANISM: Apium sp.

<400> SEQUENCE: 7
tggggaaaac aaggacattt tgcaatttgt aaaattgccc aggggttcct tagtaaagat      60
gcactgactg cagtgaaagc attgctccca gaatatgcag atggtgatct agcagctgtt     120
tgctcctggg ctgacgaggt tcgatttcat atgcgttgga gtagcccatt acattatgtg     180
gacacgcctg atttcaggtg taactataaa tactgtagag attgccatga ttctgttgga     240
cggaaagacc ggtgtgttac tggagcaatt cacaactaca cagagcaact tctattgggt     300
gttcatgact tgaattcaaa aatgaataac aacttgacgg aggcacttat gttcttatca     360
catttcgttg gtgatgtcca tcagcctcta catgttggct tccttggcga tgaaggagga     420
aacacaatca ccgtccgctg gtatcggagg aaaaccaatt tgcatcatgt atgggacaca     480
atgatgattg aatcctcctt gaagacattc tacaattcag atctttctag cttaatacaa     540
gctattcaga gcaatattac aggtgtctgg cttaccgaca gcttatcttg gagcaattgc     600
actgctgatc atgtggtttg tccagacccg tatgcttctg aaagcattga gttggcctgc     660
aagtttgcct acagaaatgc cacacctggg accactttag agatgagta cttcctctct     720
cggttgcctg ttgcggagaa gaggttggct caggctgggg tccgtttggc tgctactctt     780
aaccgaatct tcacttcaaa ccccagcgat ctcacaagat tgaatatgca taatggtgga     840
catagaagca gtaacaatat tgaaatagtg taa                                  873

<210> SEQ ID NO 8
<211> LENGTH: 290
<212> TYPE: PRT
<213> ORGANISM: Apium sp.

<400> SEQUENCE: 8

Trp Gly Lys Gln Gly His Phe Ala Ile Cys Lys Ile Ala Gln Gly Phe
1               5                   10                  15

Leu Ser Lys Asp Ala Leu Thr Ala Val Lys Ala Leu Leu Pro Glu Tyr
                20                  25                  30

Ala Asp Gly Asp Leu Ala Ala Val Cys Ser Trp Ala Asp Glu Val Arg
            35                  40                  45

Phe His Met Arg Trp Ser Ser Pro Leu His Tyr Val Asp Thr Pro Asp
        50                  55                  60

Phe Arg Cys Asn Tyr Lys Tyr Cys Arg Asp Cys His Asp Ser Val Gly
65                  70                  75                  80

Arg Lys Asp Arg Cys Val Thr Gly Ala Ile His Asn Tyr Thr Glu Gln
```

```
                        85                  90                  95
Leu Leu Leu Gly Val His Asp Leu Asn Ser Lys Met Asn Asn Asn Leu
            100                 105                 110

Thr Glu Ala Leu Met Phe Leu Ser His Phe Val Gly Asp Val His Gln
            115                 120                 125

Pro Leu His Val Gly Phe Leu Gly Asp Glu Gly Gly Asn Thr Ile Thr
            130                 135                 140

Val Arg Trp Tyr Arg Arg Lys Thr Asn Leu His His Val Trp Asp Thr
145                 150                 155                 160

Met Met Ile Glu Ser Ser Leu Lys Thr Phe Tyr Asn Ser Asp Leu Ser
                165                 170                 175

Ser Leu Ile Gln Ala Ile Gln Ser Asn Ile Thr Gly Val Trp Leu Thr
            180                 185                 190

Asp Ser Leu Ser Trp Ser Asn Cys Thr Ala Asp His Val Val Cys Pro
            195                 200                 205

Asp Pro Tyr Ala Ser Glu Ser Ile Glu Leu Ala Cys Lys Phe Ala Tyr
            210                 215                 220

Arg Asn Ala Thr Pro Gly Thr Thr Leu Gly Asp Glu Tyr Phe Leu Ser
225                 230                 235                 240

Arg Leu Pro Val Ala Glu Lys Arg Leu Ala Gln Ala Gly Val Arg Leu
                245                 250                 255

Ala Ala Thr Leu Asn Arg Ile Phe Thr Ser Pro Ser Asp Leu Thr
            260                 265                 270

Arg Leu Asn Met His Asn Gly Gly His Arg Ser Ser Asn Asn Ile Glu
            275                 280                 285

Ile Val
    290

<210> SEQ ID NO 9
<211> LENGTH: 921
<212> TYPE: DNA
<213> ORGANISM: Mimulus guttatus

<400> SEQUENCE: 9
atgcagatgt cgatttcacg aggaattttt gtttcttatt ttgctttatt tctttgtgtt     60
tgtgttgttt atgaaccttg tgtccaggca tggagtaaag aaggtcattc catgacatgc    120
aaaattgctc aggatttgct gggaccagag gcgaagcatg ctgtccaaat gctgttacct    180
gaaaatgtta atggtgattt atcggcactt agcgtgtggc ctgaccaagt aagacactgg    240
tataagtacc gttggacgag ccctcttcac ttcatagaca caccagatca agcctgtaat    300
ttcaattatc agagggattg ccatgatcca catggtgtta agggtatgtg tgtagcgggg    360
gcaattcaga acttcaccaa tcagctttcg cattatcggc acggaacctc tgatcgacgc    420
tataatatga cagaggcctt gttgttcttg gcacacttca tgggagatat tcatcagcca    480
ctgcatgttg gattcacgag tgacgaagga gaaacactag acttgcg ctggttcaga       540 cacaagtcaa atctgcacca tgtatgggac agagagataa ttcttacagc tgcagcagat    600
tactacggaa aggacattga cctcctgcaa gaagacatta agggaaactt cactgatgga    660
atctggtctg gtgatcttgc ctcttggagg gaatgcagtg atatattttc ttgtgtcaac    720
aagtatgctg ctgagagtat aaacatggcc tgcaaatggg gttacaaaga tgttaaatca    780
ggggacactc tttcgagatga ttactttaat tcaagattgc cgattgttat gaaacgcata    840
gctcagggtg gagtccgttt agctatgatt ttgaaccggg ttttcggtga tagcaaagag    900
```
gattccttaa ttgctactta a            921

<210> SEQ ID NO 10
<211> LENGTH: 306
<212> TYPE: PRT
<213> ORGANISM: Mimulus guttatus

<400> SEQUENCE: 10

```
Met Gln Met Ser Ile Ser Arg Gly Ile Phe Val Ser Tyr Phe Ala Leu
1               5                   10                  15

Phe Leu Cys Val Cys Val Val Tyr Glu Pro Cys Val Gln Ala Trp Ser
            20                  25                  30

Lys Glu Gly His Ser Met Thr Cys Lys Ile Ala Gln Asp Leu Leu Gly
        35                  40                  45

Pro Glu Ala Lys His Ala Val Gln Met Leu Leu Pro Glu Asn Val Asn
    50                  55                  60

Gly Asp Leu Ser Ala Leu Ser Val Trp Pro Asp Gln Val Arg His Trp
65                  70                  75                  80

Tyr Lys Tyr Arg Trp Thr Ser Pro Leu His Phe Ile Asp Thr Pro Asp
                85                  90                  95

Gln Ala Cys Asn Phe Asn Tyr Gln Arg Asp Cys His Asp Pro His Gly
            100                 105                 110

Val Lys Gly Met Cys Val Ala Gly Ala Ile Gln Asn Phe Thr Asn Gln
        115                 120                 125

Leu Ser His Tyr Arg His Gly Thr Ser Asp Arg Arg Tyr Asn Met Thr
130                 135                 140

Glu Ala Leu Leu Phe Leu Ala His Phe Met Gly Asp Ile His Gln Pro
145                 150                 155                 160

Leu His Val Gly Phe Thr Ser Asp Glu Gly Gly Asn Thr Ile Asp Leu
                165                 170                 175

Arg Trp Phe Arg His Lys Ser Asn Leu His His Val Trp Asp Arg Glu
            180                 185                 190

Ile Ile Leu Thr Ala Ala Ala Asp Tyr Tyr Gly Lys Asp Ile Asp Leu
        195                 200                 205

Leu Gln Glu Asp Ile Lys Gly Asn Phe Thr Asp Gly Ile Trp Ser Gly
    210                 215                 220

Asp Leu Ala Ser Trp Arg Glu Cys Ser Asp Ile Phe Ser Cys Val Asn
225                 230                 235                 240

Lys Tyr Ala Ala Glu Ser Ile Asn Met Ala Cys Lys Trp Gly Tyr Lys
                245                 250                 255

Asp Val Lys Ser Gly Asp Thr Leu Ser Asp Asp Tyr Phe Asn Ser Arg
            260                 265                 270

Leu Pro Ile Val Met Lys Arg Ile Ala Gln Gly Gly Val Arg Leu Ala
        275                 280                 285

Met Ile Leu Asn Arg Val Phe Gly Asp Ser Lys Glu Asp Ser Leu Ile
    290                 295                 300

Ala Thr
305
```

<210> SEQ ID NO 11
<211> LENGTH: 308
<212> TYPE: PRT
<213> ORGANISM: Artificial Sequence
<220> FEATURE:
<223> OTHER INFORMATION: Synthetic construct: Insect Cell Expression

<400> SEQUENCE: 11

Met Lys Phe Leu Val Asn Val Ala Leu Val Phe Met Val Tyr Ile
1               5                   10                  15

Ser Tyr Ile Tyr Ala Trp Ser Lys Glu Gly His Ser Met Thr Cys Lys
            20                  25                  30

Ile Ala Gln Asp Leu Leu Gly Pro Glu Ala Lys His Ala Val Gln Met
            35                  40                  45

Leu Leu Pro Glu Asn Val Asn Gly Asp Leu Ser Ala Leu Ser Val Trp
50                  55                  60

Pro Asp Gln Val Arg His Trp Tyr Lys Tyr Arg Trp Thr Ser Pro Leu
65                  70                  75                  80

His Phe Ile Asp Thr Pro Asp Gln Ala Cys Asn Phe Asn Tyr Gln Arg
                85                  90                  95

Asp Cys His Asp Pro His Gly Val Lys Gly Met Cys Val Ala Gly Ala
            100                 105                 110

Ile Gln Asn Phe Thr Asn Gln Leu Ser His Tyr Arg His Gly Thr Ser
            115                 120                 125

Asp Arg Arg Tyr Asn Met Thr Glu Ala Leu Leu Phe Leu Ala His Phe
130                 135                 140

Met Gly Asp Ile His Gln Pro Leu His Val Gly Phe Thr Ser Asp Glu
145                 150                 155                 160

Gly Gly Asn Thr Ile Asp Leu Arg Trp Phe Arg His Lys Ser Asn Leu
                165                 170                 175

His His Val Trp Asp Arg Glu Ile Ile Leu Thr Ala Ala Asp Tyr
            180                 185                 190

Tyr Gly Lys Asp Ile Asp Leu Leu Gln Glu Asp Ile Lys Gly Asn Phe
            195                 200                 205

Thr Asp Gly Ile Trp Ser Gly Asp Leu Ala Ser Trp Arg Glu Cys Ser
210                 215                 220

Asp Ile Phe Ser Cys Val Asn Lys Tyr Ala Ala Glu Ser Ile Asn Met
225                 230                 235                 240

Ala Cys Lys Trp Gly Tyr Lys Asp Val Lys Ser Gly Asp Thr Leu Ser
                245                 250                 255

Asp Asp Tyr Phe Asn Ser Arg Leu Pro Ile Val Met Lys Arg Ile Ala
            260                 265                 270

Gln Gly Gly Val Arg Leu Ala Met Ile Leu Asn Arg Val Phe Gly Asp
            275                 280                 285

Ser Lys Glu Asp Ser Leu Ile Ala Thr Gly Ser His His His His
    290                 295                 300

His His His Gly
305

<210> SEQ ID NO 12
<211> LENGTH: 909
<212> TYPE: DNA
<213> ORGANISM: Solanum tuberosum

<400> SEQUENCE: 12
atgttgaggt taacttcatt aagcattatt ttctttctct gtcttgcttt tatcaaccat      60
catggtgctg aagcatggag caaagagggg catatgatga catgtcgcat cgcgcagggc     120
ttgttgaatg atgaggcagc tcatgcagtc aagatgttgt tgccggaata tgttaacggc     180
gacttatcgg ccctctgtgt gtggccggat caagtccggc actggtataa gtataaatgg     240
acaagccctc tacacttcat tgatacacca gataaagctt gcaactttga ttatgaaagg     300

```
gactgtcatg atcaacatgg agtgaaggat atgtgtgttg ctggtgcaat tcagaacttt    360
actactcaac tctctcatta cagagaggga acttctgatc gtcgatataa tatgacagag    420
gccttgctgt tcttgtcaca ttttatggga gatatccatc aaccaatgca tgttggcttt    480
acaagtgatg ctggaggaaa tagtattgat ttacgctggt ttaggcataa atcgaacttg    540
caccatgtgt gggataggga gataattcta acagctgcta agactacta tgcaaaggat     600 gtaaacctcc ttgaagaaga cattgaagga aacttcactg acggaatttg gtctgatgat    660
cttgcttctt ggagagaatg tggcaatgtc ttttcttgtg taaacaagtt tgcaacggaa    720
agtataaata tagcatgcaa atggggatac aaaagtgttg aagctggtga aactttatca    780
gatgattatt tcaattcaag acttccaata gtgatgaaac gagtagcaca aggtggaata    840
cgattagcca tgcttttaaa caacgttttt ggagtttctc aacaagaaga ttcagttgct    900
gcaacttaa                                                             909

<210> SEQ ID NO 13
<211> LENGTH: 302
<212> TYPE: PRT
<213> ORGANISM: Solanum tuberosum

<400> SEQUENCE: 13

Met Leu Arg Leu Thr Ser Leu Ser Ile Ile Phe Phe Leu Cys Leu Ala
1               5                   10                  15

Phe Ile Asn His His Gly Ala Glu Ala Trp Ser Lys Glu Gly His Met
            20                  25                  30

Met Thr Cys Arg Ile Ala Gln Gly Leu Leu Asn Asp Glu Ala Ala His
        35                  40                  45

Ala Val Lys Met Leu Leu Pro Glu Tyr Val Asn Gly Asp Leu Ser Ala
    50                  55                  60

Leu Cys Val Trp Pro Asp Gln Val Arg His Trp Tyr Lys Tyr Lys Trp
65                  70                  75                  80

Thr Ser Pro Leu His Phe Ile Asp Thr Pro Asp Lys Ala Cys Asn Phe
                85                  90                  95

Asp Tyr Glu Arg Asp Cys His Asp Gln His Gly Val Lys Asp Met Cys
            100                 105                 110

Val Ala Gly Ala Ile Gln Asn Phe Thr Thr Gln Leu Ser His Tyr Arg
        115                 120                 125

Glu Gly Thr Ser Asp Arg Arg Tyr Asn Met Thr Glu Ala Leu Leu Phe
    130                 135                 140

Leu Ser His Phe Met Gly Asp Ile His Gln Pro Met His Val Gly Phe
145                 150                 155                 160

Thr Ser Asp Ala Gly Gly Asn Ser Ile Asp Leu Arg Trp Phe Arg His
                165                 170                 175

Lys Ser Asn Leu His His Val Trp Asp Arg Glu Ile Ile Leu Thr Ala
            180                 185                 190

Ala Lys Asp Tyr Tyr Ala Lys Asp Val Asn Leu Glu Glu Asp Ile
        195                 200                 205

Glu Gly Asn Phe Thr Asp Gly Ile Trp Ser Asp Leu Ala Ser Trp
    210                 215                 220

Arg Glu Cys Gly Asn Val Phe Ser Cys Val Asn Lys Phe Ala Thr Glu
225                 230                 235                 240

Ser Ile Asn Ile Ala Cys Lys Trp Gly Tyr Lys Ser Val Glu Ala Gly
                245                 250                 255

Glu Thr Leu Ser Asp Asp Tyr Phe Asn Ser Arg Leu Pro Ile Val Met
```

```
                260                 265                 270
Lys Arg Val Ala Gln Gly Gly Ile Arg Leu Ala Met Leu Leu Asn Asn
            275                 280                 285

Val Phe Gly Val Ser Gln Gln Glu Asp Ser Val Ala Ala Thr
        290                 295                 300

<210> SEQ ID NO 14
<211> LENGTH: 276
<212> TYPE: PRT
<213> ORGANISM: Mimulus guttatus

<400> SEQUENCE: 14

Trp Ser Lys Glu Gly His Ser Met Thr Cys Lys Ile Ala Gln Asp Leu
1               5                   10                  15

Leu Gly Pro Glu Ala Lys His Ala Val Gln Met Leu Leu Pro Glu Asn
            20                  25                  30

Val Asn Gly Asp Leu Ser Ala Leu Ser Val Trp Pro Asp Gln Val Arg
        35                  40                  45

His Trp Tyr Lys Tyr Arg Trp Thr Ser Pro Leu His Phe Ile Asp Thr
    50                  55                  60

Pro Asp Gln Ala Cys Asn Phe Asn Tyr Gln Arg Asp Cys His Asp Pro
65                  70                  75                  80

His Gly Val Lys Gly Met Cys Val Ala Gly Ala Ile Gln Asn Phe Thr
                85                  90                  95

Asn Gln Leu Ser His Tyr Arg His Gly Thr Ser Asp Arg Arg Tyr Asn
            100                 105                 110

Met Thr Glu Ala Leu Leu Phe Leu Ala His Phe Met Gly Asp Ile His
        115                 120                 125

Gln Pro Leu His Val Gly Phe Thr Ser Asp Glu Gly Gly Asn Thr Ile
    130                 135                 140

Asp Leu Arg Trp Phe Arg His Lys Ser Asn Leu His His Val Trp Asp
145                 150                 155                 160

Arg Glu Ile Ile Leu Thr Ala Ala Asp Tyr Tyr Gly Lys Asp Ile
                165                 170                 175

Asp Leu Leu Gln Glu Asp Ile Lys Gly Asn Phe Thr Asp Gly Ile Trp
            180                 185                 190

Ser Gly Asp Leu Ala Ser Trp Arg Glu Cys Ser Asp Ile Phe Ser Cys
        195                 200                 205

Val Asn Lys Tyr Ala Ala Glu Ser Ile Asn Met Ala Cys Lys Trp Gly
    210                 215                 220

Tyr Lys Asp Val Lys Ser Gly Asp Thr Leu Ser Asp Tyr Phe Asn
225                 230                 235                 240

Ser Arg Leu Pro Ile Val Met Lys Arg Ile Ala Gln Gly Gly Val Arg
                245                 250                 255

Leu Ala Met Ile Leu Asn Arg Val Phe Gly Asp Ser Lys Glu Asp Ser
            260                 265                 270

Leu Ile Ala Thr
        275

<210> SEQ ID NO 15
<211> LENGTH: 831
<212> TYPE: DNA
<213> ORGANISM: Vitis vinifera

<400> SEQUENCE: 15 atgtgggaa aggaaggaca ctatgcagtt tgtaaaatag ctgaggggtt cctttctgaa    60
```

-continued

```
gatgcattag gagcagtgaa aggattgctt ccagattatg ctgatggtga tctggctgcc    120
gtttgctcct gggctgatga gattcgtcac aacttccatt ggcgatggag tggccccttta   180 cattatgtag atacaccaga ttacaggtgt aattatgaat actgcagaga ctgccatgac    240
ttcagaggac acaaagatat atgtgtaact ggagcaattt acaactacac aaagcaactc    300
acttctggtt atcacaattc aggttcagaa ataagataca atttgacaga ggccctcatg    360
ttcttatcag attttattgg ggatgtccat cagcccctac atgttggttt tactggagat    420
gaaggtggga acacaataat agtccgttgg taccggagga agactaattt gcatcatata    480
tgggatgaca tgatcattga ttccgccttg aagacatatt acaattcaga tattgcaatc    540
atgatacaag ccattcaaag aaatattaca ggtgactggt cctttgatat ctcatcatgg    600
aaaaattgtg catctgatga tacggcttgt ccaaacctgt atgcgtctga aggcattagt    660
ttagcttgca gtttgcttta cagaaatgcc acaccaggaa gcactctagg agatgattac    720
ttcctgtctc ggctaccaat tgtggagaag aggctagccc cgagtgggat ccgcctggct    780 gccacccttta accgtatctt tgcttctcaa ggcaagagag ctaaagcatg a            831
```

<210> SEQ ID NO 16
<211> LENGTH: 276
<212> TYPE: PRT
<213> ORGANISM: Vitis vinifera

<400> SEQUENCE: 16

```
Met Trp Gly Lys Glu Gly His Tyr Ala Val Cys Lys Ile Ala Glu Gly
1               5                   10                  15

Phe Leu Ser Glu Asp Ala Leu Gly Ala Val Lys Gly Leu Leu Pro Asp
            20                  25                  30

Tyr Ala Asp Gly Asp Leu Ala Ala Val Cys Ser Trp Ala Asp Glu Ile
        35                  40                  45

Arg His Asn Phe His Trp Arg Trp Ser Gly Pro Leu His Tyr Val Asp
    50                  55                  60

Thr Pro Asp Tyr Arg Cys Asn Tyr Glu Tyr Cys Arg Asp Cys His Asp
65                  70                  75                  80

Phe Arg Gly His Lys Asp Ile Cys Val Thr Gly Ala Ile Tyr Asn Tyr
                85                  90                  95

Thr Lys Gln Leu Thr Ser Gly Tyr His Asn Ser Gly Ser Glu Ile Arg
            100                 105                 110

Tyr Asn Leu Thr Glu Ala Leu Met Phe Leu Ser Asp Phe Ile Gly Asp
        115                 120                 125

Val His Gln Pro Leu His Val Gly Phe Thr Gly Asp Glu Gly Gly Asn
    130                 135                 140

Thr Ile Ile Val Arg Trp Tyr Arg Arg Lys Thr Asn Leu His His Ile
145                 150                 155                 160

Trp Asp Asp Met Ile Ile Asp Ser Ala Leu Lys Thr Tyr Tyr Asn Ser
                165                 170                 175

Asp Ile Ala Ile Met Ile Gln Ala Ile Gln Arg Asn Ile Thr Gly Asp
            180                 185                 190

Trp Ser Phe Asp Ile Ser Ser Trp Lys Asn Cys Ala Ser Asp Asp Thr
        195                 200                 205

Ala Cys Pro Asn Leu Tyr Ala Ser Glu Gly Ile Ser Leu Ala Cys Lys
    210                 215                 220

Phe Ala Tyr Arg Asn Ala Thr Pro Gly Ser Thr Leu Gly Asp Asp Tyr
225                 230                 235                 240
```

```
Phe Leu Ser Arg Leu Pro Ile Val Glu Lys Arg Leu Ala Pro Ser Gly
                245                 250                 255

Ile Arg Leu Ala Ala Thr Leu Asn Arg Ile Phe Ala Ser Gln Gly Lys
            260                 265                 270

Arg Ala Lys Ala
        275

<210> SEQ ID NO 17
<211> LENGTH: 331
<212> TYPE: PRT
<213> ORGANISM: Artificial Sequence
<220> FEATURE:
<223> OTHER INFORMATION: Synthetic construct: Insect Cell Expression

<400> SEQUENCE: 17

Met Lys Phe Leu Val Asn Val Ala Leu Val Phe Met Val Val Tyr Ile
1               5                   10                  15

Ser Tyr Ile Tyr Ala Trp Gly Lys Glu Gly His Tyr Ala Val Cys Lys
            20                  25                  30

Ile Ala Glu Gly Phe Leu Ser Glu Asp Ala Leu Gly Ala Val Lys Ala
        35                  40                  45

Leu Leu Pro Asp Tyr Ala Glu Gly Asp Leu Ala Ala Val Cys Ser Trp
    50                  55                  60

Ala Asp Glu Ile Arg His Asn Phe His Trp Arg Trp Ser Gly Pro Leu
65                  70                  75                  80

His Tyr Val Asp Thr Pro Asp Tyr Arg Cys Asn Tyr Glu Tyr Cys Arg
                85                  90                  95

Asp Cys His Asp Phe Arg Gly His Lys Asp Ile Cys Val Thr Gly Ala
            100                 105                 110

Ile Tyr Asn Tyr Thr Lys Gln Leu Thr Ser Gly Tyr His Asn Ser Gly
        115                 120                 125

Ser Glu Ile Arg Tyr Asn Leu Thr Glu Ala Leu Met Phe Leu Ser His
    130                 135                 140

Phe Ile Gly Asp Val His Gln Pro Leu His Val Gly Phe Thr Gly Asp
145                 150                 155                 160

Glu Gly Gly Asn Thr Ile Ile Val Arg Trp Tyr Arg Arg Lys Thr Asn
                165                 170                 175

Leu His His Ile Trp Asp Asn Met Ile Ile Asp Ser Ala Leu Lys Thr
            180                 185                 190

Tyr Tyr Asn Ser Asp Leu Ala Ile Met Ile Gln Ala Ile Gln Arg Asn
        195                 200                 205

Ile Thr Gly Asp Trp Ser Phe Asp Ile Ser Ser Trp Lys Asn Cys Ala
    210                 215                 220

Ser Asp Asp Thr Ala Cys Pro Asn Leu Tyr Ala Ser Glu Ser Ile Ser
225                 230                 235                 240

Leu Ala Cys Lys Phe Ala Tyr Arg Asn Ala Thr Pro Gly Ser Thr Leu
                245                 250                 255

Gly Asp Asp Tyr Phe Leu Ser Arg Leu Pro Ile Val Glu Lys Arg Leu
            260                 265                 270

Ala Gln Gly Gly Ile Arg Leu Ala Ala Thr Leu Asn Arg Ile Phe Ala
        275                 280                 285

Ser Gln Pro Lys Ile Ser Leu Lys His Glu Asp Lys Arg Val Glu Lys
    290                 295                 300

Thr Thr Pro Val Asp Tyr Ile Glu Trp Ser Pro Leu Gln Gln Phe Ser
305                 310                 315                 320
```

Gly Ser His His His His His His His Gly
            325                 330

<210> SEQ ID NO 18
<211> LENGTH: 840
<212> TYPE: DNA
<213> ORGANISM: Artificial Sequence
<220> FEATURE:
<223> OTHER INFORMATION: Synthetic construct: Chocolate pots

<400> SEQUENCE: 18

```
atgacttggg gattttgggc acatcggcaa atacatcgcc aagccgttta tcttatgcct      60
tcgcccgtgg cagagttctt tcgcgcaaat gttcaagaac ttgtcgaccg ctcggttgaa     120
gccgatgaac gccgacgcat agaccccaac gaagctccgc aacacttcat tgatttagac     180
cgctacggtg cctatccttt tgaacaactt ccgagagatt atgaaaaagc cgttgagaaa     240
ttcggctatg agcggctgaa agaaaatgga cttgtgccgt ggcgcattgc cgcctttgcc     300
gatagcctca ccaacgcatt tcgggagcag aaccgcgaaa aaattttata cttcgccgca     360
aatttagggc attatgtcgc cgatgctaac gtgccacttc atgccaccga aaactacgac     420
ggacaactca cagggcaaaa aggattgcac gcacgttggg aaactattta tcctcaaaag     480
tttatgctcc cacgagaaac cacctatctc gaaacgggga gcatctttat cattgacaac     540
atcaccgaag aagccttcaa ctggtcatta gaaagttatg tattgagcca acaagttttg     600
gcgattgata agcaaattca atcggaattg tcagaagaag aattgtatga gttaaattca     660
tcagacgcgc cgccatttcg tcgcgatttt tcacaacgct attatgaaaa actcaaagaa     720
aaattgaatc aaatggttga aaaatgcttt gagttaagcg tcattagggt agcgtcagtt     780
tggtatttt cttggttaaa agcagaaaaa ccgaatttat ttaacttatt aaaaaattga     840
```

<210> SEQ ID NO 19
<211> LENGTH: 279
<212> TYPE: PRT
<213> ORGANISM: Artificial Sequence
<220> FEATURE:
<223> OTHER INFORMATION: Synthetic construct: Chocolate pots

<400> SEQUENCE: 19

Met Thr Trp Gly Phe Trp Ala His Arg Gln Ile His Arg Gln Ala Val
1               5                   10                  15

Tyr Leu Met Pro Ser Pro Val Ala Glu Phe Phe Arg Ala Asn Val Gln
            20                  25                  30

Glu Leu Val Asp Arg Ser Val Glu Ala Asp Glu Arg Arg Ile Asp
        35                  40                  45

Pro Asn Glu Ala Pro Gln His Phe Ile Asp Leu Asp Arg Tyr Gly Ala
    50                  55                  60

Tyr Pro Phe Glu Gln Leu Pro Arg Asp Tyr Glu Lys Ala Val Glu Lys
65                  70                  75                  80

Phe Gly Tyr Glu Arg Leu Lys Glu Asn Gly Leu Val Pro Trp Arg Ile
                85                  90                  95

Ala Ala Phe Ala Asp Ser Leu Thr Asn Ala Phe Arg Glu Gln Asn Arg
            100                 105                 110

Glu Lys Ile Leu Tyr Phe Ala Ala Asn Leu Gly His Tyr Val Ala Asp
        115                 120                 125

Ala Asn Val Pro Leu His Ala Thr Glu Asn Tyr Asp Gly Gln Leu Thr
    130                 135                 140

```
Gly Gln Lys Gly Leu His Ala Arg Trp Glu Thr Ile Tyr Pro Gln Lys
145                 150                 155                 160

Phe Met Leu Pro Arg Glu Thr Thr Tyr Leu Glu Asn Gly Ser Ile Phe
                165                 170                 175

Ile Ile Asp Asn Ile Thr Glu Glu Ala Phe Asn Trp Ser Leu Glu Ser
            180                 185                 190

Tyr Val Leu Ser Gln Gln Val Leu Ala Ile Asp Lys Gln Ile Gln Ser
        195                 200                 205

Glu Leu Ser Glu Glu Leu Tyr Glu Leu Asn Ser Ser Asp Ala Pro
210                 215                 220

Pro Phe Arg Arg Asp Phe Ser Gln Arg Tyr Tyr Glu Lys Leu Lys Glu
225                 230                 235                 240

Lys Leu Asn Gln Met Val Glu Lys Cys Phe Glu Leu Ser Val Ile Arg
                245                 250                 255

Val Ala Ser Val Trp Tyr Phe Ser Trp Leu Lys Ala Glu Lys Pro Asn
            260                 265                 270

Leu Phe Asn Leu Leu Lys Asn
        275
```

```
<210> SEQ ID NO 20
<211> LENGTH: 807
<212> TYPE: DNA
<213> ORGANISM: Unknown
<220> FEATURE:
<223> OTHER INFORMATION: Obsidian pool

<400> SEQUENCE: 20
atgttttggg cacatcaaaa agtcaacgag catgccattg atttattacc cgagccactc     60
cgcagttttt atgaacaaaa taaggaatac atagttaagg agtcggtcgc ccctgatctc    120
aggcgtgcag aaaacaagga agaaggttat tatcactata tggatctcga taaatatggt    180
gaatatccgt tcaagaattt gccagaaaac tacgacgacg cagtaaaaag gtttggttac    240
gatactgttc tcaagaacgg aattgtgccg tggaaggtaa aatggttgac agacagtttg    300
agtcaagcta tggagagaaa ggatgtgcca caggtcttaa gactttcagc cgaccttggt    360
cattatgttg ctgacatgca tgttccattt cattcgacag aaaattatga tggacagctg    420
acaggcaaca taggaataca cttcagatgg gaaagcggca ttccagaaca ttttggaaca    480
aattacaact atgagggaat agagcccgct gtttacttca gcatcctga taaaaaggca    540
tttgagatac tgactatgag ttacaagttg attctaccct ctctcaaggc tgatagtctt    600
gcaaagttg gattgaatgg aaagagactt tataaagttg agagaagaa cggtaaaaaa    660
gtttacgttt attcaaacga gtattatgag aagttcaaca aaaaccttgg tggtattgta    720
gaatcgcaga tgaggctggc aatccatgat gttgcaagct actggtatac tgcatgggta    780
aatgccggta aaccaaagtt ttggtaa                                        807
```

```
<210> SEQ ID NO 21
<211> LENGTH: 268
<212> TYPE: PRT
<213> ORGANISM: Unknown
<220> FEATURE:
<223> OTHER INFORMATION: Obsidian pool

<400> SEQUENCE: 21

Met Phe Trp Ala His Gln Lys Val Asn Glu His Ala Ile Asp Leu Leu
1               5                   10                  15

Pro Glu Pro Leu Arg Ser Phe Tyr Glu Gln Asn Lys Glu Tyr Ile Val
```

```
                20                  25                  30
Lys Glu Ser Val Ala Pro Asp Leu Arg Arg Ala Glu Asn Lys Glu Glu
            35                  40                  45

Gly Tyr Tyr His Tyr Met Asp Leu Asp Lys Tyr Gly Glu Tyr Pro Phe
        50                  55                  60

Lys Asn Leu Pro Glu Asn Tyr Asp Asp Ala Val Lys Arg Phe Gly Tyr
 65                  70                  75                  80

Asp Thr Val Leu Lys Asn Gly Ile Val Pro Trp Lys Val Lys Trp Leu
                85                  90                  95

Thr Asp Ser Leu Ser Gln Ala Met Glu Arg Lys Asp Val Pro Gln Val
            100                 105                 110

Leu Arg Leu Ser Ala Asp Leu Gly His Tyr Val Ala Asp Met His Val
        115                 120                 125

Pro Phe His Ser Thr Glu Asn Tyr Asp Gly Gln Leu Thr Gly Asn Ile
        130                 135                 140

Gly Ile His Phe Arg Trp Glu Ser Gly Ile Pro Glu His Phe Gly Thr
145                 150                 155                 160

Asn Tyr Asn Tyr Glu Gly Ile Glu Pro Ala Val Tyr Phe Lys His Pro
                165                 170                 175

Asp Lys Lys Ala Phe Glu Ile Leu Thr Met Ser Tyr Lys Leu Ile Leu
            180                 185                 190

Pro Ser Leu Lys Ala Asp Ser Leu Ala Lys Val Gly Leu Asn Gly Lys
        195                 200                 205

Arg Leu Tyr Lys Val Glu Arg Glu Asp Gly Lys Lys Val Tyr Val Tyr
        210                 215                 220

Ser Asn Glu Tyr Tyr Glu Lys Phe Asn Lys Asn Leu Gly Gly Ile Val
225                 230                 235                 240

Glu Ser Gln Met Arg Leu Ala Ile His Asp Val Ala Ser Tyr Trp Tyr
                245                 250                 255

Thr Ala Trp Val Asn Ala Gly Lys Pro Lys Phe Trp
            260                 265

<210> SEQ ID NO 22
<211> LENGTH: 972
<212> TYPE: DNA
<213> ORGANISM: Vitis vinifera

<400> SEQUENCE: 22
atggcttggt ctggggtctt gttgattgtg agggcacttg ttcttctgca attgattcct      60
ggaattctga gttggggaaa ggaaggacac tatgcagttt gtaaaatagc tgaggggttc     120
ctttctgaag atgcattagg agcagtgaaa gcattgcttc cagattatgc tgaaggtgat     180
ctggctgcgg tttgctcctg ggctgatgag attcgtcaca acttccattg gcgatggagt     240 ggcccttta c attatgtaga tacgccagat tacaggtgta actatgaata ctgcagagac     300
tgccatgact tcagaggaca caaagatata tgtgtaactg agcaatttta caattacaca     360
aagcaactca cttctggtta tcacaattca ggttcagaaa taagatacaa tttgacagag     420
gcactcatgt tcttatcaca ttttattggg gatgtccatc agcccctaca tgttggtttt     480
actggagatg aaggtgggaa cacaataata gtccgttggt accggaggaa gactaatttg     540
catcatatat gggataacat gatcattgat tccgccctga agacatatta caattcagat     600
cttgcaatca tgatacaagc cattcaaaga aatattacgg gtgattggtc ctttgatatc     660
tcatcatgga aaaattgtgc atctgatgat acggcttgtc caaacctgta tgcttctgaa     720
```

```
agcattagtt tagcttgcaa gtttgcttac agaaatgcca caccaggaag cactctagga      780
gatgattact tcctgtctcg gctaccaatt gtggagaaga ggctagccca aggtgggatc      840
cgcctggctg ccacccttaa ccgtatcttt gcttctcaac caaaaatctc tctcaagcat      900
gaagataaaa gggtagagaa aacaactcca gtggattata tagagtggag cccactgcaa      960
caattttcat aa                                                          972
```

```
<210> SEQ ID NO 23
<211> LENGTH: 323
<212> TYPE: PRT
<213> ORGANISM: Vitis vinifera

<400> SEQUENCE: 23
```

Met Ala Trp Ser Gly Val Leu Leu Ile Val Arg Ala Leu Val Leu Leu
1               5                   10                  15

Gln Leu Ile Pro Gly Ile Leu Ser Trp Gly Lys Glu Gly His Tyr Ala
            20                  25                  30

Val Cys Lys Ile Ala Glu Gly Phe Leu Ser Glu Asp Ala Leu Gly Ala
        35                  40                  45

Val Lys Ala Leu Leu Pro Asp Tyr Ala Glu Gly Asp Leu Ala Ala Val
    50                  55                  60

Cys Ser Trp Ala Asp Glu Ile Arg His Asn Phe His Trp Arg Trp Ser
65                  70                  75                  80

Gly Pro Leu His Tyr Val Asp Thr Pro Asp Tyr Arg Cys Asn Tyr Glu
                85                  90                  95

Tyr Cys Arg Asp Cys His Asp Phe Arg Gly His Lys Asp Ile Cys Val
            100                 105                 110

Thr Gly Ala Ile Tyr Asn Tyr Thr Lys Gln Leu Thr Ser Gly Tyr His
        115                 120                 125

Asn Ser Gly Ser Glu Ile Arg Tyr Asn Leu Thr Glu Ala Leu Met Phe
130                 135                 140

Leu Ser His Phe Ile Gly Asp Val His Gln Pro Leu His Val Gly Phe
145                 150                 155                 160

Thr Gly Asp Glu Gly Gly Asn Thr Ile Ile Val Arg Trp Tyr Arg Arg
                165                 170                 175

Lys Thr Asn Leu His His Ile Trp Asp Asn Met Ile Ile Asp Ser Ala
            180                 185                 190

Leu Lys Thr Tyr Tyr Asn Ser Asp Leu Ala Ile Met Ile Gln Ala Ile
        195                 200                 205

Gln Arg Asn Ile Thr Gly Asp Trp Ser Phe Asp Ile Ser Ser Trp Lys
    210                 215                 220

Asn Cys Ala Ser Asp Asp Thr Ala Cys Pro Asn Leu Tyr Ala Ser Glu
225                 230                 235                 240

Ser Ile Ser Leu Ala Cys Lys Phe Ala Tyr Arg Asn Ala Thr Pro Gly
                245                 250                 255

Ser Thr Leu Gly Asp Asp Tyr Phe Leu Ser Arg Leu Pro Ile Val Glu
            260                 265                 270

Lys Arg Leu Ala Gln Gly Gly Ile Arg Leu Ala Ala Thr Leu Asn Arg
        275                 280                 285

Ile Phe Ala Ser Gln Pro Lys Ile Ser Leu Lys His Glu Asp Lys Arg
    290                 295                 300

Val Glu Lys Thr Thr Pro Val Asp Tyr Ile Glu Trp Ser Pro Leu Gln
305                 310                 315                 320

Gln Phe Ser

```
<210> SEQ ID NO 24
<211> LENGTH: 891
<212> TYPE: DNA
<213> ORGANISM: Solanum sp.

<400> SEQUENCE: 24
atgggtgggt tgagctcaa atggtttgta ggagtagctg ttgttctgat gatggttcaa      60
aatattcttg gttggggaa agagggacac tatattatct gcaaaattgc tgaggaatat     120
ctaacagaag atgctttagc tgcagtcaaa gcattactcc agatcaagc cgaaggtgat     180
cttgcagctg tctgctcctg gcctgatgag gttcggcgcc actaccacta ccgctggagc     240
tctccattac attatgtaga tacacctgat tcttgtgca attacaaata ttgccgagac     300
tgccatgacg ggcatgggct caaggacagg tgtgttacgg agcaatata caactactca     360
atgcaacttt cgcaggata ttatgatttg aattcagaaa atacaacttt gactgaagca     420
cttatgttct tgtctcattt tgttggtgac gtacatcagc ctctccatgt tggtttcact     480
ggagatcttg gtggaaacag tataattgtt cgttggtaca ggaggaagac taatttgcac     540
catgtatggg ataacatgat tattgaatct gcgttgaaga catactacaa atctgatata     600
atgttaatga cacaagttct tctgaaaaac atcactcatg aatggtccga tgatgttcca     660
tcttgggaag attgcaagga gatggtttgt cctgacccat atgcttctga agtatccgt     720
ttggcctgca aatttgccta cagaaatgca accccgggaa gcactttaac agacgattac     780
ttcctctctc gtcttcctgt tgtggagaag aggttggcac aaggtggggt ccgcttggcc     840
gaagttctca cagaattttt cactaaaaaa ccatcagatg ctgcacaatg a             891

<210> SEQ ID NO 25
<211> LENGTH: 296
<212> TYPE: PRT
<213> ORGANISM: Solanum tuberosum

<400> SEQUENCE: 25

Met Gly Gly Phe Glu Leu Lys Trp Phe Val Gly Val Ala Val Val Leu
1               5                   10                  15
Met Met Val Gln Asn Ile Leu Gly Trp Gly Lys Glu Gly His Tyr Ile
                20                  25                  30
Ile Cys Lys Ile Ala Glu Glu Tyr Leu Thr Glu Asp Ala Leu Ala Ala
            35                  40                  45
Val Lys Ala Leu Leu Pro Asp Gln Ala Glu Gly Asp Leu Ala Ala Val
        50                  55                  60
Cys Ser Trp Pro Asp Glu Val Arg Arg His Tyr His Tyr Arg Trp Ser
65                  70                  75                  80
Ser Pro Leu His Tyr Val Asp Thr Pro Asp Phe Leu Cys Asn Tyr Lys
                85                  90                  95
Tyr Cys Arg Asp Cys His Asp Gly His Gly Leu Lys Asp Arg Cys Val
            100                 105                 110
Thr Gly Ala Ile Tyr Asn Tyr Ser Met Gln Leu Ser Gln Gly Tyr Tyr
        115                 120                 125
Asp Leu Asn Ser Glu Lys Tyr Asn Leu Thr Glu Ala Leu Met Phe Leu
    130                 135                 140
Ser His Phe Val Gly Asp Val His Gln Pro Leu His Val Gly Phe Thr
145                 150                 155                 160
Gly Asp Leu Gly Gly Asn Ser Ile Ile Val Arg Trp Tyr Arg Arg Lys
                165                 170                 175
```

```
Thr Asn Leu His His Val Trp Asp Asn Met Ile Ile Glu Ser Ala Leu
            180                 185                 190

Lys Thr Tyr Tyr Lys Ser Asp Ile Met Leu Met Thr Gln Val Leu Leu
        195                 200                 205

Lys Asn Ile Thr His Glu Trp Ser Asp Asp Val Pro Ser Trp Glu Asp
    210                 215                 220

Cys Lys Glu Met Val Cys Pro Asp Pro Tyr Ala Ser Glu Ser Ile Arg
225                 230                 235                 240

Leu Ala Cys Lys Phe Ala Tyr Arg Asn Ala Thr Pro Gly Ser Thr Leu
                245                 250                 255

Thr Asp Asp Tyr Phe Leu Ser Arg Leu Pro Val Val Glu Lys Arg Leu
            260                 265                 270

Ala Gln Gly Gly Val Arg Leu Ala Glu Val Leu Asn Arg Ile Phe Thr
        275                 280                 285

Lys Lys Pro Ser Asp Ala Ala Gln
    290                 295

<210> SEQ ID NO 26
<211> LENGTH: 885
<212> TYPE: DNA
<213> ORGANISM: Medicago sp.

<400> SEQUENCE: 26
atgatcacgc tcttagttcc gttgctgcta tcactcgcgt tgccaaatgt tctggcttgg      60
ggaaaagatg gtcactatgc aatttgtaaa atttcacagg agtatcttag tgaagatgct     120
ctatttgcag tcaaacaatt acttccagat tctgctcaag ctgatcttgc ttcagtttgc     180
tcttggcctg atgagattcg ccataattac cattatcgtt ggagtagtcc tttacattat     240
attgatacac cagatttcaa atgtaactat caatattgca gagactgtca tgattcttat     300
ggacataagc atagatgcgt tactggagca atatacaatt atacaatgca attaaaatta     360
gctaacgccg atgcttcatc tgaattaaaa tataacttga cagaggcact tatgttcttg     420
tcacattttg ttggagatgt tcatcagccc ctacatgttg gttttactgg agacctaggt     480
ggaaactcaa taacagttcg ttggtacagg aggaaaacaa atcttcatca cgtatgggat     540
aacatgatta ttgagtctgc tctgaaaaag ttctatggtt cagatctttc aactatgata     600
caggctattc aaaggaatat tagtgatatt tggtcaaatg atgtatctat ttgggaacat     660
tgtgcacaca accacacagc atgtccagac cggtatgctt ctgagagtat tagcttggca     720
tgcaagtttg cgtataagaa tgctacaccg ggaagcactt tggaagatga ctacttcctt     780
tctcggttgc ctattgtgga aaaaggctg gctcaaggtg gtgtgcgact gcagctatc     840 ctcaaccaca ttttcactcc gaagaccaga atagctcaag cttaa                    885

<210> SEQ ID NO 27
<211> LENGTH: 294
<212> TYPE: PRT
<213> ORGANISM: Medicago sp.

<400> SEQUENCE: 27

Met Ile Thr Leu Leu Val Pro Leu Leu Leu Ser Leu Ala Leu Pro Asn
1               5                  10                  15

Val Leu Ala Trp Gly Lys Asp Gly His Tyr Ala Ile Cys Lys Ile Ser
            20                  25                  30

Gln Glu Tyr Leu Ser Glu Asp Ala Leu Phe Ala Val Lys Gln Leu Leu
        35                  40                  45
```

Pro Asp Ser Ala Gln Ala Asp Leu Ala Ser Val Cys Ser Trp Pro Asp
    50                  55                  60

Glu Ile Arg His Asn Tyr His Tyr Arg Trp Ser Pro Leu His Tyr
65                  70                  75                  80

Ile Asp Thr Pro Asp Phe Lys Cys Asn Tyr Gln Tyr Cys Arg Asp Cys
                85                  90                  95

His Asp Ser Tyr Gly His Lys His Arg Cys Val Thr Gly Ala Ile Tyr
            100                 105                 110

Asn Tyr Thr Met Gln Leu Lys Leu Ala Asn Ala Asp Ala Ser Ser Glu
        115                 120                 125

Leu Lys Tyr Asn Leu Thr Glu Ala Leu Met Phe Leu Ser His Phe Val
    130                 135                 140

Gly Asp Val His Gln Pro Leu His Val Gly Phe Thr Gly Asp Leu Gly
145                 150                 155                 160

Gly Asn Ser Ile Thr Val Arg Trp Tyr Arg Arg Lys Thr Asn Leu His
                165                 170                 175

His Val Trp Asp Asn Met Ile Ile Glu Ser Ala Leu Lys Lys Phe Tyr
            180                 185                 190

Gly Ser Asp Leu Ser Thr Met Ile Gln Ala Ile Gln Arg Asn Ile Ser
        195                 200                 205

Asp Ile Trp Ser Asn Asp Val Ser Ile Trp Glu His Cys Ala His Asn
    210                 215                 220

His Thr Ala Cys Pro Asp Arg Tyr Ala Ser Glu Ser Ile Ser Leu Ala
225                 230                 235                 240

Cys Lys Phe Ala Tyr Lys Asn Ala Thr Pro Gly Ser Thr Leu Glu Asp
                245                 250                 255

Asp Tyr Phe Leu Ser Arg Leu Pro Ile Val Glu Lys Arg Leu Ala Gln
            260                 265                 270

Gly Gly Val Arg Leu Ala Ala Ile Leu Asn His Ile Phe Thr Pro Lys
        275                 280                 285

Thr Arg Ile Ala Gln Ala
    290

<210> SEQ ID NO 28
<211> LENGTH: 271
<212> TYPE: PRT
<213> ORGANISM: Artificial Sequence
<220> FEATURE:
<223> OTHER INFORMATION: Synthetic construct

<400> SEQUENCE: 28

Trp Gly Lys Glu Gly His Tyr Ala Val Cys Lys Ile Ala Glu Gly Phe
1               5                   10                  15

Leu Ser Glu Asp Ala Leu Gly Ala Val Lys Gly Leu Leu Pro Asp Tyr
            20                  25                  30

Ala Asp Gly Asp Leu Ala Ala Val Cys Ser Trp Ala Asp Glu Ile Arg
        35                  40                  45

His Asn Phe His Trp Arg Trp Ser Gly Pro Leu His Tyr Val Asp Thr
    50                  55                  60

Pro Asp Tyr Arg Cys Asn Tyr Glu Tyr Cys Arg Asp Cys His Asp Phe
65                  70                  75                  80

Arg Gly His Lys Asp Ile Cys Val Thr Gly Ala Ile Tyr Asn Tyr Thr
                85                  90                  95

Lys Gln Leu Thr Ser Gly Tyr His Asn Ser Gly Ser Glu Ile Arg Tyr
            100                 105                 110

```
Asn Leu Thr Glu Ala Leu Met Phe Leu Ser Asp Phe Ile Gly Asp Val
            115                 120                 125

His Gln Pro Leu His Val Gly Phe Thr Gly Asp Glu Gly Gly Asn Thr
        130                 135                 140

Ile Ile Val Arg Trp Tyr Arg Arg Lys Thr Asn Leu His His Ile Trp
145                 150                 155                 160

Asp Asp Met Ile Ile Asp Ser Ala Leu Lys Thr Tyr Tyr Asn Ser Asp
                165                 170                 175

Ile Ala Ile Met Ile Gln Ala Ile Gln Arg Asn Ile Thr Gly Asp Trp
                180                 185                 190

Ser Phe Asp Ile Ser Ser Trp Lys Asn Cys Ala Ser Asp Asp Thr Ala
            195                 200                 205

Cys Pro Asn Leu Tyr Ala Ser Glu Gly Ile Ser Leu Ala Cys Lys Phe
        210                 215                 220

Ala Tyr Arg Asn Ala Thr Pro Gly Ser Thr Leu Gly Asp Asp Tyr Phe
225                 230                 235                 240

Leu Ser Arg Leu Pro Ile Val Glu Lys Arg Leu Ala Pro Ser Gly Ile
                245                 250                 255

Arg Leu Ala Ala Thr Leu Asn Arg Ile Phe Ala Ser Gln Gly Lys
                260                 265                 270
```

<210> SEQ ID NO 29
<211> LENGTH: 271
<212> TYPE: PRT
<213> ORGANISM: Vitis vinifera

<400> SEQUENCE: 29

```
Trp Gly Lys Glu Gly His Tyr Ala Val Cys Lys Ile Ala Glu Gly Phe
1               5                   10                  15

Leu Ser Glu Asp Ala Leu Gly Ala Val Lys Ala Leu Leu Pro Asp Tyr
            20                  25                  30

Ala Glu Gly Asp Leu Ala Ala Val Cys Ser Trp Ala Asp Glu Ile Arg
        35                  40                  45

His Asn Phe His Trp Arg Trp Ser Gly Pro Leu His Tyr Val Asp Thr
    50                  55                  60

Pro Asp Tyr Arg Cys Asn Tyr Glu Tyr Cys Arg Asp Cys His Asp Phe
65                  70                  75                  80

Arg Gly His Lys Asp Ile Cys Val Thr Gly Ala Ile Tyr Asn Tyr Thr
                85                  90                  95

Lys Gln Leu Thr Ser Gly Tyr His Asn Ser Gly Ser Glu Ile Arg Tyr
            100                 105                 110

Asn Leu Thr Glu Ala Leu Met Phe Leu Ser His Phe Ile Gly Asp Val
            115                 120                 125

His Gln Pro Leu His Val Gly Phe Thr Gly Asp Glu Gly Gly Asn Thr
        130                 135                 140

Ile Ile Val Arg Trp Tyr Arg Arg Lys Thr Asn Leu His His Ile Trp
145                 150                 155                 160

Asp Asn Met Ile Ile Asp Ser Ala Leu Lys Thr Tyr Tyr Asn Ser Asp
                165                 170                 175

Leu Ala Ile Met Ile Gln Ala Ile Gln Arg Asn Ile Thr Gly Asp Trp
                180                 185                 190

Ser Phe Asp Ile Ser Ser Trp Lys Asn Cys Ala Ser Asp Asp Thr Ala
            195                 200                 205

Cys Pro Asn Leu Tyr Ala Ser Glu Ser Ile Ser Leu Ala Cys Lys Phe
```

```
              210                 215                 220
Ala Tyr Arg Asn Ala Thr Pro Gly Ser Thr Leu Gly Asp Asp Tyr Phe
225                 230                 235                 240

Leu Ser Arg Leu Pro Ile Val Glu Lys Arg Leu Ala Gln Gly Gly Ile
                245                 250                 255

Arg Leu Ala Ala Thr Leu Asn Arg Ile Phe Ala Ser Gln Pro Lys
            260                 265                 270

<210> SEQ ID NO 30
<211> LENGTH: 828
<212> TYPE: DNA
<213> ORGANISM: Artificial Sequence
<220> FEATURE:
<223> OTHER INFORMATION: Synthetic construct: Codon Optimized Mature
      Core Mimulus DNA Encodes SEQ ID NO:14

<400> SEQUENCE: 30
tggagtaagg agggacatag catgacatgt aagatagccc aggacttgtt gggtcccgaa      60
gccaaacacg ccgtgcaaat gttgttgcct gaaaatgtga acggcgacct aagcgccttg     120
tcggtgtggc cggaccaagt gagacactgg tacaaataca gatggacctc ccctttgcac     180
ttcattgaca cccccgatca ggcttgcaac tttaactacc agagagactg ccatgacccg     240
cacggtgtaa aaggcatgtg cgttgccggt gccattcaaa atttcacgaa ccaattgtcg     300
cactacagac acgcacgtc ggacagacgt tacaacatga cggaggcctt gttgttttg      360 gcccacttta tgggcgatat tcatcagccg ttgcacgtgg gcttcacgtc agacgaaggc     420
ggcaacacga ttgacttgag atggtttcgc cacaagagca cttgcatca cgtatgggat     480 cgagaaatta tcctaactgc cgctgcggac tactacggaa aggacatcga cctactccag     540
gaggatatca aaggcaattt tactgacggc atctggtcgg gcgatttggc tcgtggagaa     600
gaatgttcgg acatttttttc gtgtgtgaac aagtacgctg ccgaatccat aaacatggct     660
tgtaaatggg gctacaagga tgtgaaatcg ggtgacacgc tctcggacga ctatttcaac     720
agtcgtctcc cgatcgtaat gaaaagaatc gctcaaggag gcgttcgctt agcaatgatt     780
ctcaacagag tattcggtga tagcaaagag gacagcttga ttgccacg                  828

<210> SEQ ID NO 31
<211> LENGTH: 933
<212> TYPE: DNA
<213> ORGANISM: Artificial Sequence
<220> FEATURE:
<223> OTHER INFORMATION: Synthetic construct: Blue Sky Report Mimulus
      DNA Encodes SEQ ID NO:11

<400> SEQUENCE: 31
accatgaagt tcttggtcaa cgtagcactg gttttttatgg tagtctatat cagctacatt      60
tacgcgtgga gtaaggaggg acatagcatg acatgtaaga tagcccagga cttgttgggt    120
cccgaagcca aacacgccgt gcaaatgttg ttgcctgaaa atgtgaacgg cgacctaagc    180
gccttgtcgg tgtggccgga ccaagtgaga cactggtaca atacagatg gacctcccct    240 ttgcacttca ttgacacccc cgatcaggct gcaacttta actaccagag agactgccat    300
gacccgcacg gtgtaaaagg catgtgcgtt gccggtgcca ttcaaaattt cacgaaccaa    360
ttgtcgcact acagacacgg cacgtcggac agacgttaca acatgacgga ggccttgttg    420
tttttggccc actttatggg cgatattcat cagccgttgc acgtgggctt cacgtcagac    480
gaaggcggca acacgattga cttgagatgg tttcgccaca agagcaactt gcatcacgta    540
```

```
tgggatcgag aaattatcct aactgccgct gcggactact acggaaagga catcgaccta    600
ctccaggagg atatcaaagg caattttact gacggcatct ggtcgggcga tttggcctcg    660
tggagagaat gttcggacat tttttcgtgt gtgaacaagt acgctgccga atccataaac    720
atggcttgta aatggggcta caaggatgtg aaatcgggtg acacgctctc ggacgactat    780
ttcaacagtc gtctcccgat cgtaatgaaa agaatcgctc aaggaggcgt tcgcttagca    840
atgattctca acagagtatt cggtgatagc aaagaggaca gcttgattgc cacgggctcg    900
caccatcacc accatcacca ccacggttga taa                                 933
```

<210> SEQ ID NO 32
<211> LENGTH: 897
<212> TYPE: DNA
<213> ORGANISM: Artificial Sequence
<220> FEATURE:
<223> OTHER INFORMATION: Synthetic construct: Codon Optimized Vitis DNA
      Encodes Residues XXX YYY of SEQ ID NO:23

<400> SEQUENCE: 32

```
tggggcaaag aaggccacta cgccgtgtgt aagattgcgg agggcttttt gtcggaagac    60
gcattgggag cggtcaaagc cttgttgccg gactacgcgg aaggcgactt ggcagccgta    120
tgtagctggg ccgacgagat cagacacaac tttcactgga gatggtcggg cccactgcat    180
tacgtcgaca cgccggatta cagatgcaac tacgagtact gccgcgactg tcacgacttc    240
agaggccaca agacatttg cgtcacgggc gcgatataca actacacgaa acaattgacg    300
tcgggctacc acaacagtgg ctccgagatt cgatacaacc tcacggaggc cttgatgttc    360
ctctcgcatt tcattggcga cgtgcaccaa ccgctgcatg tgggctttac gggcgatgaa    420
ggcggaaata cgatcattgt ccgttggtac cgcagaaaga ccaacctcca ccacatatgg    480
gacaacatga tcatcgactc ggcgttgaag acctactaca cagcgaccct ggccataatg    540
atccaggcga ttcaaagaaa catcaccggc gattggtcct ttgacatcag cagctggaag    600
aactgtgcca gtgacgacac tgcttgtccg aacctatacg cgtcggagag catctcgttg    660
gcctgtaaat ttgcctacag aaatgccacc cccggttcga cgctgggcga cgactacttc    720
ttgtcgcgat tgccgattgt tgaaaaacgc ctcgcccaag gcggtattag attggccgcc    780
accttgaacc gtattttgc ctcgcaaccg aaaatctcgc tgaaacacga agacaagaga    840
gtcgagaaga cgacgccggt agactacatc gagtggtcgc cattgcaaca gttcagc     897
```

<210> SEQ ID NO 33
<211> LENGTH: 1002
<212> TYPE: DNA
<213> ORGANISM: Artificial Sequence
<220> FEATURE:
<223> OTHER INFORMATION: Synthetic construct: Blue Sky Report Vitis DNA
      Encodes SEQ ID NO:17

<400> SEQUENCE: 33

```
accatgaagt tcttggtgaa cgtggcgctg gtgttcatgg tcgtgtacat ctcctacatt    60
tacgcgtggg gcaaagaagg ccactacgcc gtgtgtaaga ttgcggaggg ctttttgtcg    120
gaagacgcat tgggagcggt caaagccttg ttgccggact acgcggaagg cgacttggca    180
gccgtatgta gctgggccga cgagatcaga cacaactttc actggagatg gtcgggccca    240
ctgcattacg tcgacacgcc ggattacaga tgcaactacg agtactgccg cgactgtcac    300
gacttcagag gccacaaaga catttgcgtc acgggcgcga tatacaacta cacgaaacaa    360
ttgacgtcgg gctaccacaa cagtggctcc gagattcgat acaacctcac ggaggccttg    420
```

```
atgttcctct cgcatttcat tggcgacgtg caccaaccgc tgcatgtggg ctttacgggc    480
gatgaaggcg gaaatacgat cattgtccgt tggtaccgca gaaagaccaa cctccaccac    540
atatgggaca acatgatcat cgactcggcg ttgaagacct actacaacag cgacctggcc    600
ataatgatcc aggcgattca aagaaacatc accggcgatt ggtcctttga catcagcagc    660
tggaagaact gtgccagtga cgacactgct tgtccgaacc tatacgcgtc ggagagcatc    720
tcgttggcct gtaaatttgc ctacagaaat gccaccccg gttcgacgct gggcgacgac     780
tacttcttgt cgcgattgcc gattgttgaa aaacgcctcg cccaaggcgg tattagattg    840
gccgccacct tgaaccgtat ttttgcctcg caaccgaaaa tctcgctgaa acacgaagac    900
aagagagtcg agaagacgac gccggtagac tacatcgagt ggtcgccatt gcaacagttc    960
agcggaagcc accaccatca ccaccatcat cacggctgat aa                      1002
```